(12) United States Patent
Roche et al.

(10) Patent No.: US 8,765,728 B2
(45) Date of Patent: Jul. 1, 2014

(54) [1,5]-DIAZOCIN DERIVATIVES

(75) Inventors: Didier Roche, Ecully (FR); Fabrice Chimienti, Grenoble (FR); Martin Ohsten, Ruy Montceau (FR)

(73) Assignee: MelliTech (FR)

( * ) Notice: Subject to any disclaimer, the term of this patent is extended or adjusted under 35 U.S.C. 154(b) by 63 days.

(21) Appl. No.: 13/509,805

(22) PCT Filed: Nov. 16, 2010

(86) PCT No.: PCT/EP2010/067601
§ 371 (c)(1),
(2), (4) Date: May 15, 2012

(87) PCT Pub. No.: WO2011/058193
PCT Pub. Date: May 19, 2011

(65) Prior Publication Data
US 2012/0225892 A1    Sep. 6, 2012

Related U.S. Application Data

(60) Provisional application No. 61/261,382, filed on Nov. 16, 2009.

(51) Int. Cl.
| | |
|---|---|
| C07D 245/06 | (2006.01) |
| A61K 31/395 | (2006.01) |
| C07D 245/04 | (2006.01) |
| C07D 403/14 | (2006.01) |
| C07D 407/06 | (2006.01) |
| C07D 471/04 | (2006.01) |
| C07D 403/06 | (2006.01) |
| C07D 413/06 | (2006.01) |

(52) U.S. Cl.
CPC ........... *C07D 245/06* (2013.01); *C07D 245/04* (2013.01); *C07D 403/14* (2013.01); *C07D 407/06* (2013.01); *C07D 471/04* (2013.01); *C07D 403/06* (2013.01); *C07D 413/06* (2013.01)
USPC .......................................... 514/183; 540/460

(58) Field of Classification Search
USPC .......................................... 540/460; 514/183
See application file for complete search history.

(56) References Cited

U.S. PATENT DOCUMENTS

| | | | |
|---|---|---|---|
| 5,532,237 A | 7/1996 | Gallant et al. | |
| 5,624,941 A | 4/1997 | Barth et al. | |
| 6,028,084 A | 2/2000 | Barth et al. | |
| 6,335,345 B1 | 1/2002 | Fukami et al. | |
| 8,148,391 B2 * | 4/2012 | Ahmed et al. | 514/275 |

FOREIGN PATENT DOCUMENTS

| | | | |
|---|---|---|---|
| GB | 1272081 A | 4/1972 | |
| WO | 9640631 A1 | 12/1996 | |
| WO | 9728149 A1 | 8/1997 | |
| WO | 9804528 A2 | 2/1998 | |
| WO | 9841519 A1 | 9/1998 | |
| WO | 9901423 A1 | 1/1999 | |
| WO | 9902499 A1 | 1/1999 | |
| WO | 9964002 A1 | 12/1999 | |
| WO | 0010968 A2 | 3/2000 | |
| WO | 0039088 A1 | 7/2000 | |
| WO | 0042026 A1 | 7/2000 | |
| WO | 0058293 A3 | 10/2000 | |
| WO | 0058360 A2 | 10/2000 | |
| WO | 0059887 A1 | 10/2000 | |
| WO | 0069810 A1 | 11/2000 | |
| WO | 0074679 A1 | 12/2000 | |
| WO | 0114376 A1 | 3/2001 | |
| WO | 0123420 A1 | 4/2001 | |
| WO | 0170337 A1 | 9/2001 | |
| WO | 0170708 A1 | 9/2001 | |
| WO | 02062764 A1 | 8/2002 | |
| WO | 02068388 A2 | 9/2002 | |
| WO | 02076949 A1 | 10/2002 | |
| WO | 02083128 A1 | 10/2002 | |
| WO | 03000025 A2 | 1/2003 | |
| WO | 03000180 A2 | 1/2003 | |
| WO | 03000181 A2 | 1/2003 | |
| WO | 03002530 A2 | 1/2003 | |

(Continued)

OTHER PUBLICATIONS

Ahren, Bo, "Islet G Protein-Coupled Receptors as Potential Targets for Treatment of Type 2 Diabetes", Nature Reviews, May 2009, pp. 369-385, vol. 8.

(Continued)

*Primary Examiner* — Bruck Kifle
(74) *Attorney, Agent, or Firm* — Banner & Witcoff, Ltd.

(57) ABSTRACT

The present invention relates to compounds of formula (I) compositions, in particular pharmaceutical compositions, and medicaments comprising at least one compound of formula (I). The invention also relates to the use of such a compound for manufacturing a medicament. In particular the medicament and the pharmaceutical composition are intended to treat diseases linked with insulin regulation problems, such as diabetes. This invention aims also to methods for treating or preventing such diseases.

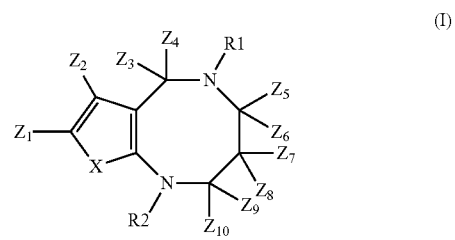

20 Claims, No Drawings

(56) References Cited

FOREIGN PATENT DOCUMENTS

| | | | |
|---|---|---|---|
| WO | 03002531 A2 | 1/2003 |
| WO | 03002553 A2 | 1/2003 |
| WO | 03002593 A2 | 1/2003 |
| WO | 03004496 A1 | 1/2003 |
| WO | 03004498 A1 | 1/2003 |
| WO | 03007887 A2 | 1/2003 |
| WO | 03009847 A1 | 2/2003 |
| WO | 03057244 A2 | 7/2003 |
| WO | 03057730 A1 | 7/2003 |
| WO | 03070881 A2 | 8/2003 |
| WO | 03080585 A1 | 10/2003 |
| WO | 03099227 A2 | 12/2003 |
| WO | 03099836 A1 | 12/2003 |
| WO | 2004000869 A1 | 12/2003 |
| WO | 2004038405 A2 | 5/2004 |
| WO | 2004038421 A2 | 5/2004 |
| WO | 2004043957 A1 | 5/2004 |
| WO | 2004072031 A2 | 8/2004 |
| WO | 2004072650 A1 | 8/2004 |
| WO | 2005025570 A1 | 3/2005 |
| WO | 2005044801 A1 | 5/2005 |
| WO | 2005072769 A1 | 8/2005 |
| WO | 2005091944 A2 | 10/2005 |
| WO | 2005123132 A2 | 12/2005 |
| WO | 2006002350 A1 | 1/2006 |
| WO | 2006044531 A2 | 4/2006 |
| WO | 2006052566 A2 | 5/2006 |
| WO | 2006076231 A2 | 7/2006 |
| WO | 2006124544 A2 | 11/2006 |
| WO | 2007075847 A2 | 7/2007 |
| WO | 2007082381 A1 | 7/2007 |
| WO | 2007115968 A2 | 10/2007 |
| WO | 2007118185 A2 | 10/2007 |
| WO | 2007122482 A1 | 11/2007 |
| WO | 2007134613 A1 | 11/2007 |
| WO | 2008118948 A1 | 10/2008 |
| WO | 2008121563 A2 | 10/2008 |
| WO | 2008145749 A1 | 12/2008 |
| WO | 2009019600 A2 | 2/2009 |
| WO | 2009023180 A1 | 2/2009 |
| WO | 2009058662 A2 | 5/2009 |
| WO | 2009058734 A1 | 5/2009 |

OTHER PUBLICATIONS

Baxter, et al., "Thyroid Hormone Mimetics: Potential Applications in Atherosclerosis, Obesity and Type 2 Diabetes", Nature Reviews, Apr. 2009, pp. 308-320, vol. 8.

Chaki, et al., "Recent Advances in Feeding Suppressing Agents: Potential Therapeutic Strategy for the Treatment of Obesity", Expert Opin. Ther. Patents, 2001, pp. 1677-1692, vol. 11.

Girard, J., "The Incretins: From the Concept to Their Use in the Treatment of Type 2 Diabetes. Part A: Incretins: Concept and Physiological Fuctions", Diabetes & Metabolism, Sep. 1, 2008, pp. 550-559, vol. 34.

Heneberg, P., "Use of Protein Tyrosine Phosphatase Inhibitors as Promising Targeted Therapeutic Drugs", Current Medicinal Chemistry, 2009, pp. 706-733, vol. 16.

Klapars, et al., "Synthesis of Medium Ring Nitrogen Heterocycles Via a Tandem Copper-Catalyzed C-N Bond Formation Ring-Expansion Process", J. Am. Chem. Soc., 2004, pp. 3529-3533, vol. 126.

Merglen, et al., "Glucose Sensitivity and Metabolism-Secretion Coupling Studied During Two-Year Continuous Culture in INS-1E Insulinoma Cells", Endocrinology, 2004, pp. 667-677.

Nathan, et al., "Impaired Fasting Glucose and Impaired Glucose Tolerance", Diabetes Care, Mar. 2007, pp. 753-759, vol. 30.

Pal, Manojit, "Recent Advances in Glucokinase Activators for the Treatment of Type 2 Diabetes", Drug Discovery Today, Aug., 2009, pp. 784-792, vol. 14.

Somsak, et al., "New Inhibitors of Glycogen Phosphorylase as Potential Antidiabetic Agents", Current Medicinal Chemistry, 2008, pp. 2933-2983, vol. 15.

Spanswick et al., "Emerging Antiobesity Drugs", Expert Opin. Emerging Drugs, 2003, pp. 217-237, vol. 8.

Speake, et al., "Recent Advances in the Development of Melanocortin-4 Receptor Agonists", Expert Opin. Ther. Patents, 2002, pp. 1631-1638, vol. 12.

Vvideman, et al., "Mining Incretin Hormone Pathways for Novel Therapies", Trends in Endocrinology and Metabolism, 2009, pp. 280-286.

Derieg et al., Journal of Organic Chemistry, 34, 179-183 (1969).

* cited by examiner

[1,5]-DIAZOCIN DERIVATIVES

RELATED APPLICATION DATA

This application is a National Stage Application under 35 U.S.C. 371 of co-pending PCT application PCT/EP2010/067601 designating the United States and filed Nov. 16, 2010; which claims the benefit of EP patent application number 09176111.4 and filed Nov. 16, 2009 and U.S. provisional application No. 61/261,382 and filed Nov. 16, 2009, each of which are hereby incorporated by reference in their entireties.

FIELD OF THE INVENTION

The present invention relates to compounds having a [1,5]-diazocin, in particular a 4-oxo-[1,5]-diazocin, type of structure, to compositions and/or medicaments comprising at least one compound of this type, and their use as a constituent in a medicament, in particular for the treatment of diabetes, more particularly of non-insulin dependent diabetes mellitus (type II diabetes), insulin dependent diabetes mellitus (type I diabetes), and/or of hypertension, pre-diabetes, metabolic syndrome and obesity.

The chemical structure of formula I compounds may provide the substances with the capability of modulating, in particular enhancing or potentiating, the secretion of insulin. This may provide, for example, a self-regulatory treatment system for non-insulin dependent diabetes mellitus (type II diabetes), insulin dependent diabetes mellitus (type I diabetes), hypertension, pre-diabetes, the metabolic syndrome, obesity and/or related metabolic diseases.

BACKGROUND OF THE INVENTION

Diabetes Classification, Diagnosis and Prevalence

Many diseases, conditions and disorders are linked with insulin regulation problems. Examples of such diseases, conditions and disorders are listed below.

Diabetes is a chronic disease that occurs when the pancreas does not produce enough insulin, or alternatively, when the body cannot effectively use the insulin it produces. Insulin is a hormone that regulates blood sugar. Hyperglycaemia, or raised blood sugar, is a common effect of uncontrolled diabetes and over time leads to serious damage to many of the body's systems, especially nerves and/or blood vessels. People are diagnosed with diabetes if they show a fasting plasma glucose (FPG) level FPG≥126 mg/dl (7.0 mmol/l) or a Random plasma glucose≥200 mg/dl (11.1 mmol/l) plus symptoms (reference: American Diabetes Association Standards of Medical Care in Diabetes Diabetes Care, Vol. 32, Supp 1, January 2009).

Type 1 diabetes (previously known as insulin-dependent or childhood-onset) is characterized by a lack of insulin production. Without daily administration of insulin, type 1 diabetes is rapidly fatal. Symptoms include excessive excretion of urine (polyuria), thirst (polydipsia), constant hunger, weight loss, vision changes and fatigue. These symptoms may occur suddenly.

Type 2 diabetes (formerly called non-insulin-dependent or adult-onset) results from the body's ineffective use of insulin. Type 2 diabetes comprises 90% of people with diabetes around the world, and is largely the result of excess body weight and physical inactivity. Symptoms may be similar to those of type 1 diabetes, but are often less marked. As a result, the disease may be diagnosed several years after onset, once complications have already arisen. Until recently, this type of diabetes was seen only in adults but it is now also occurring in obese children.

Gestational diabetes is hyperglycaemia which is first recognized during pregnancy. Symptoms of gestational diabetes are similar to Type 2 diabetes. Gestational diabetes is most often diagnosed through prenatal screening, rather than reported symptoms.

Impaired Glucose Tolerance (IGT) and Impaired Fasting Glycaemia (IFG) are intermediate conditions in the transition between normality and diabetes. People with IGT or IFG are at high risk of progressing to Type 2 diabetes, although this is not inevitable.

Hyperglycemia not sufficient to meet the diagnostic criteria for diabetes is categorized as either impaired fasting glucose (IFG) or impaired glucose tolerance (IGT), depending on whether it is identified through the FPG (fasting plasma glucose) or the OGTT (oral glucose tolerance test):

IFG=FPG 100 mg/dl (5.6 mmol/l) to 125 mg/dl (6.9 mmol/l)

IGT=2-h plasma glucose 140 mg/dl (7.8 mmol/l) to 199 mg/dl (11.0 mmol/l)

IFG and IGT have been officially termed "pre-diabetes." Both categories of pre-diabetes are risk factors for future diabetes and for cardiovascular disease (CVD) (Nathan D M, Davidson M B, DeFronzo R A, Heine R J, Henry R R, Pratley R, Zinman B: Impaired fasting glucose and impaired glucose tolerance: implications for care. Diabetes Care 30:753-759, 2007).

Non-insulin dependent diabetes mellitus (type 2 diabetes) develops especially in subjects with insulin resistance and a cluster of cardiovascular risk factor's such as obesity, hypertension and dyslipidemia, a syndrome which first recently has been recognized and is named "the metabolic syndrome" or "syndrome X". In accordance with the WHO (World Health Organization) definition, a patient has metabolic syndrome if he shows:

Impaired fasting blood glucose (the American Diabetes Association considers the cutoff to be 100 mg/dL)

Impaired glucose tolerance (blood glucose above 140 mg/dL two hours after a 75 g glucose challenge)

AND any two or more of the following conditions:

increased blood pressure (≥140/90 mmHg) or taking blood pressure medication increased plasma triglyceride (≥1.7 mmol/l)

low HDL cholesterol (<0.9 mmol/l for men; <1.0 mmol/l for women)

central adipositas (waist/hip ratio for men: >0.90 and for women>0.85) and/or Body Mass Index>30 kg/m$^2$)

micro albuminuria (urine albumin excretion: ≥20 μg min$^{-1}$ or albumin:creatinine ratio≥30 mg/g).

In accordance with the IDF consensus worldwide definition of the metabolic syndrome (2006), a patient has metabolic syndrome if are present the following conditions:

Central obesity (defined as waist circumference with ethnicity specific values)

AND any two or more of the following conditions:

Raised triglycerides: >150 mg/dL (1.7 mmol/L), or specific treatment for this lipid abnormality.

Reduced HDL cholesterol: <40 mg/dL (1.03 mmol/L) in males, <50 mg/dL (1.29 mmol/L) in females, or specific treatment for this lipid abnormality Raised blood pressure: systolic BP>130 or diastolic BP>85 mm Hg, or treatment of previously diagnosed hypertension.

Raised fasting plasma glucose: (FPG)>100 mg/dL (5.6 mmol/L), or previously diagnosed type 2 diabetes. If FPG>5.6 mmol/L or 100 mg/dL, OGTT (oral glucose tolerance test) is strongly recommended but is not necessary to define presence of the syndrome.

If BMI is >30 kg/m², central obesity can be assumed and waist circumference does not need to be measured.

Hypertension is more prevalent in patients with type 2 diabetes than in the non-diabetic population. It is estimated that the prevalence of arterial hypertension (blood pressure greater than 160/95 mmHg) in patients with type 2 diabetes is in the range of 40-50%. In type 2 diabetes, hypertension is often present as part of the metabolic syndrome of insulin resistance also including central obesity and dyslipidemia. Management of hypertension includes lifestyle advice (dietary advice, reduce salt intake (<6 g/day), increase aerobic exercise, the reduction of other risks of cardiovascular disease and other complications of diabetes (e.g. smoking cessation, weight reduction, improve glycaemic control, management of diabetic nephropathy (including microalbuminuria), management of hyperlipidaemia), and rigorous control of blood pressure.

Improving glycaemic control, via an improvement of insulin secretion, may be an efficient mean to delay or prevent all or part of the diseases, conditions and metabolic disorders described in this description.

The WHO estimates that more than 180 million people worldwide have diabetes. This number is likely to more than double by 2030. In 2005, an estimated 1.1 million people died from diabetes. Almost 80% of diabetes deaths occur in low and middle-income countries. Almost half of diabetes deaths occur in people under the age of 70 years; 55% of diabetes deaths are in women. WHO projects that diabetes-related deaths will increase by more than 50% in the next 10 years without urgent action. Most notably, diabetes deaths are projected to increase by over 80% in upper-middle income countries between 2006 and 2015. Diabetes and its complications impose significant economic consequences on individuals, families, health systems and countries. Without urgent action, diabetes-related deaths will increase by more than 50% in the next 10 years.

Diabetes has become one of the major causes of premature illness and death in most countries, mainly through the increased risk of cardiovascular disease (CVD). Cardiovascular disease is responsible for between 50% and 80% of deaths in people with diabetes.

Diabetes is a leading cause of blindness, amputation and kidney failure. These complications account for much of the social and financial burden of diabetes.

Although diabetes is sometimes considered a condition of developed nations, the loss of life from premature death among persons with diabetes is greatest in developing countries.

The burden of premature death from diabetes is similar to that of HIV/AIDS, yet the problem is largely unrecognized.

To help prevent type 2 diabetes and its complications, it is recommended:
  to achieve and maintain healthy body weight,
  to be physically active—at least 30 minutes of regular, moderate-intensity activity on most days. More activity is required for weight control,
  to accomplish early diagnosis through relatively inexpensive blood testing, and
  to follow treatment of diabetes involving lowering blood glucose and the levels of other known risk factors that damage to blood vessels.

Therapy for Diabetes and Related Metabolic Conditions

The ADA (American Diabetes Association) and the European Association for the Study of Diabetes published a consensus statement on the approach to management of hyperglycemia in individuals with type 2 diabetes (Nathan D M et al. Management of hyperglycemia in type 2 diabetes: a consensus algorithm for the initiation and adjustment of therapy: a consensus statement from the American Diabetes Association and the European Association for the Study of Diabetes. Diabetes Care 29:1963-1972, 2006) and recently published an update (Nathan D M et al. Medical management of hyperglycemia in type 2 diabetes: a consensus algorithm for the initiation and adjustment of therapy: a consensus statement of the American Diabetes Association and the European Association for the Study of Diabetes. Diabetes Care 32:193-203, 2009). Highlights of this approach are: intervention at the time of diagnosis with metformin in combination with lifestyle changes and continuing timely augmentation of therapy with additional agents (including early initiation of insulin therapy) as a means of achieving and maintaining recommended levels of glycemic control (i.e., A1C (glycated homoglobin)<7% for most patients). The overall objective is to achieve and maintain glycemic control and to change interventions when therapeutic goals are not being met. The algorithm took into account the evidence for A1C-lowering of the individual interventions, their additive effects, and their expense. The precise drugs used and their exact sequence may not be as important as achieving and maintaining glycemic targets safely. Medications not included in the consensus algorithm, owing to less glucose-lowering effectiveness, limited clinical data, and/or relative expense, still may be appropriate choices in individual patients to achieve glycemic goals. Initiation of insulin at time of diagnosis is recommended for individuals presenting with weight loss or other severe hyperglycemic symptoms or signs. A non-exhaustive list of currently approved diabetes medication (revised March 2007 NDEP-54-S) can be seen on www.ndep.nih.gov/media/Drug_tables_supplement.pdf.

It has become increasingly evident that the treatment should aim at simultaneously normalizing blood glucose, blood pressure, lipids and body weight to reduce the morbidity and mortality. Diet treatment, exercise and avoiding smoking are the first treatment modalities that should be started. However, it will often be necessary to add pharmacological therapy but until today no single drug that simultaneously attacks hyperglycaemia, hypertension and dyslipidemia is available for patients with metabolic syndrome, pre-diabetes or diabetes. Instead, these patients may be treated with a combination of several different drugs in addition to other action e.g., diet. This type or treatment is difficult to adjust and administer to the patient and such treatment may result in many unwanted adverse effects which in themselves may need medical treatment.

Consequently there is a long felt need for a new and combined medicament for the treatment of pre-diabetes or metabolic syndrome thereby also preventing an increase in the number of persons developing the non-insulin dependent diabetes mellitus.

Existing oral antidiabetic medicaments to be used in such treatment include the classic insulinotropic agents sulphonylureas. They act primarily by stimulating the sulphonylurea-receptor on the insulin producing beta-cells via closure of the K+ATP-sensitive channels. However if such an action also affects the myocytes in the heart, an increased risk of cardiac arrhythmias might be present. Also, it is well known in the art that sulphonylureas can cause severe and life-threatening hypoglycemia, due to their continuous action as long as they are present in the blood.

Several attempts to develop new antidiabetic agents and drugs for the treatment or prophylactic treatment of diabetes, pre-diabetes or the metabolic syndrome not having the adverse effects mentioned above, e.g. hypoglycemia and potential harmful actions on the heart functions have been made over the years. To date, no well defined, chemical stable, non-toxic, reliable and non-adverse or few adverse effects alternative to the sulphonylureas as potent insulin-secretagogues for the treatment of non-insulin dependent diabetes mellitus, pre-diabetes or the metabolic syndrome is available today. Recently marketed incretin-based therapies (GLP1 (glucagon-like peptide 1) agonists/analogs, and DPP-IV (dipeptidyl-peptidase-4) inhibitors) show insufficient clinical data to be validated as safe therapies.

In summary there is a need for drugs which are not, or which are less, leading to undesirable effect(s), which are more efficient, which are easier to administer, which allow fewer takes per day, which exhibit a wider scope of action, which are easier and/or cheaper to synthesise, which exhibit a longer storage ability and/or which are easier to formulate.

Thus, in summary, there is a need for improved or alternative drugs for treating or preventing all or part of the diseases and conditions listed above, in particular for a self-regulatory treatment of diabetes, hypertension, pre-diabetes and/or metabolic syndrome in mammals, and preferably in humans.

In order to prevent sequelae or to delay the developing of a number of the above-mentioned metabolic disorders in mammals, and in particular in humans, there is also a need for new drugs and in particular new insulin-secretagogues, more particularly avoiding or decreasing all or part of the above mentioned problems.

The present invention aims to satisfy all or part of these problems and/or needs.

SUMMARY OF THE INVENTION

An object of the invention is [1,5]-diazocin compounds of the following structure:

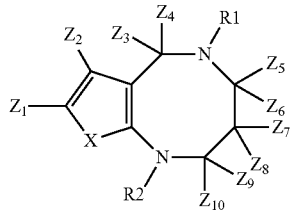

formula I their stereoisomeric forms, mixtures of stereoisomeric forms, and pharmaceutically acceptable salts or esters forms thereof, wherein the constituent members are defined infra.

Following another aspect, an object of the present invention is compositions comprising at least one compound of formula I. In particular pharmaceutical compositions or medicaments comprising a therapeutically effective amount of at least one compound of formula (I) or a pharmaceutically acceptable salt or ester form thereof with at least one pharmaceutically acceptable excipient.

Another object of the present invention is to provide methods for the treatment, prevention or amelioration of one or more symptoms of disease, disease, condition and/or disorder related to the activity of modulating the insulin regulation, in particular at least one among disease, condition and/or disorder listed in the instant description.

Still another object of the invention is the use of at least one compound of formula I for the preparation of a medicament, in particular intended for the prevention and/or the treatment of at least one disease, condition and/or disorder listed in the instant description.

These and other objects, features and advantages of the invention will be disclosed in the following detailed description.

DETAILED DESCRIPTION OF THE INVENTION

A first object of the invention is [1,5]-diazocin, in particular 4-oxo-[1,5]-diazocin, compounds of formula I:

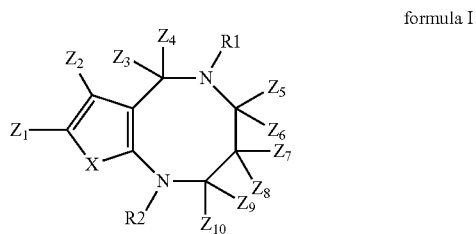

formula I wherein $R^1$ and $R^2$ represent independently H, alkyl, alkene, alkyne, heterocycle or carbocycle, optionally bearing at least one halogen atom and/or at least one function chosen from alcohol, amine, sulfone, ether, ketone, amide and ester, in particular $R^1$ and/or $R^2$ are linked to the N atom through a sulfonamide, an amine or an amide bond, X represents —O—, —S—, —C($Z^{11}$)=C($Z^{12}$)—, —N=C($Z^{13}$)— or —C($Z^{13}$)=N—, —N($Z^{14}$)—, $Z^1$ and $Z^2$ represent independently H, halogen atom, in particular F, Cl or Br, alkyl, alkoxy, alkene, alkyne, carbocycle, heterocycle, optionally substituted, in particular bearing at least one halogen atom, and/or at least one function chosen from alcohol, ether, ketone, amide and ester, $Z^3$, $Z^4$, $Z^7$, $Z^8$, $Z^9$, $Z^{10}$, $Z^{11}$, $Z^{12}$, $Z^{13}$ and $Z^{14}$ represent independently H, halogen atom, alkyl, cycloalkyl, alkene, cycloalkene, alkyne, aryl, alkylaryl, arylalkyl, optionally bearing at least one halogen atom and/or at least one function chosen from alcohol, ether, amine, amide, ketone and ester, or some of these species form together a carbocycle or an heterocycle, or $Z^2$ and $Z^1$, $Z^1$ and $Z^{11}$, $Z^1$ and $Z^{14}$, $Z^1$ and $Z^{13}$ and/or $Z^{11}$ and $Z^{12}$ form together a carbocycle or an heterocycle, for example a cycloalkyl, a cycloalkene, an heterocycloalkyl, as a cycloalkylenedioxy, an aryl or an heteroaryl cycle, optionally bearing at least one halogen atom and/or at least one function chosen from alcohol, ether, amine, amide, ketone and ester and $Z^5$ and $Z^6$ are each H or together they represent =O or =S, their stereoisomeric forms, mixtures of stereoisomeric forms, and their pharmaceutically acceptable salt and ester thereof, solvates thereof and hydrates thereof.

In —C($Z^{11}$)=C($Z^{12}$)—, —N=C($Z^{13}$)— or —C($Z^{13}$)=N—, the left part corresponds to position 9 and the right part to position 10, for example C($Z^{11}$) is at position 9 and C($Z^{12}$) at position 10.

In particular $R^1$ represents H, alkyl, alkene, alkyne, cycloalkyl, cycloalkene, aryl, alkylaryl or arylalkyl, optionally bearing at least one halogen atom and/or at least one function chosen from alcohol, ether, ketone and ester, more particularly $R^1$ represents alkyl, alkene or cycloalkyl, optionally bearing at least one halogen atom and/or at least one function chosen from alcohol, ether, ketone and ester, among the alkyl bearing an ether function can be cited alkylalkoxy, such as methoxymethyl, methoxyethyl, etc.

$R^1$ may be linked to the N atom through sulfonamide, amine or amide bond, in particular through amine or amide bond.

More particularly, $R^1$ represents H, methyl, ethyl, n-propyl, i-propyl, cyclopropyl, cyclopropylmethyl, cyclobutyl, cyclopentyl, methyl-but-2-enyl, allyl, pent-2-ynyl, 3,3-dimethyl-2-oxobutyl, 2-methoxyethyl, ethylacetyl, phenyl or benzyl.

$R^1$ may represent alkylsulfone or arylsulfone, optionally substituted, in particular $R^1$ is mesyl or tosyl.

In particular $R^1$ and $R^2$ do not each represent H.

$R^2$ may represent H, alkyl, alkene, alkyne, cycloalkyl, cycloalkene, aryl, arylkyl or alkylaryl, optionally bearing at least one alcohol, ketone, ether, ester or acid function and/or substituted, in particular with halogen atom(s). $R^2$ may be linked to the N atom through sulfonamide, amine or amide bond, in particular through amine or amide bond.

In particular $R^2$ is an alkylaryl, for example in which the alkyl chain is linear, and more particularly on which the aryl is at the end of the alkyl chain. The alkylaryl is optionally bearing at least one alcohol, ketone, ether, ester or acid function, in particular at least, or only, on the alkyl chain.

More particularly $R^2$ is chosen from benzyl, phenylethyl, in particular 2-phenylethyl and phenylpropyl, in particular 3-phenylpropyl, optionally substituted and/or bearing at least one alcohol, ketone, ether, ester or acid function.

$R^2$ may be an optionally substituted phenylethyl or phenylpropyl, optionally bearing at least one alcohol, ketone, ether, ester or acid function, more particularly at least or only on the ethyl or propyl chain. $R^2$ may be a phenylethyl bearing a ketone, a hydroxy or an ether function on the carbon bearing the phenyl group.

In particular $R^2$ is an unsubstituted or substituted 2-hydroxy-2-phenylethyl, in particular (R)-2-hydroxy-2-phenylethyl or (S)-2-hydroxy-2-phenylethyl. More particularly, $R^2$ is chosen from 2-hydroxy-2-phenylethyl, (2-methoxyphenyl)-2-hydroxy-ethyl, (3-methoxyphenyl)-2-hydroxy-ethyl, (4-methoxyphenyl)-2-hydroxy-ethyl, (2,5-dimethoxyphenyl)-2-hydroxy-ethyl, (2-chlorophenyl)-2-hydroxy-ethyl, (3-chlorophenyl)-2-hydroxy-ethyl, (4-chlorophenyl)-2-hydroxy-ethyl, (2-fluorophenyl)-2-hydroxy-ethyl, (3-fluorophenyl)-2-hydroxy-ethyl, (4-fluorophenyl)-2-hydroxy-ethyl, (3,4-difluorophenyl)-2-hydroxy-ethyl, (2,3-dihydrobenzo[b][1,4]dioxin-6-yl)-2-hydroxy-ethyl, (2-hydroxy-2-(4-(pyrrolidin-1-yl)phenyl)ethyl, 2-hydroxy-2-(4-(trifluoromethoxy)-phenylethyl.

In particular $R^2$ is an unsubstituted or substituted 2-oxo-2-phenylethyl. More particularly, $R^2$ is chosen from 2-oxo-2-phenylethyl, (2-methoxyphenyl)-2-oxo-ethyl, (3-methoxyphenyl)-2-oxo-ethyl, (4-methoxyphenyl)-2-oxo-ethyl, (2,5-di methoxyphenyl)-2-oxo-ethyl, (2-chlorophenyl)-2-oxo-ethyl, (3-chlorophenyl)-2-oxo-ethyl, (4-chlorophenyl)-2-oxo-ethyl, (2-fluorophenyl)-2-oxo-ethyl, (3-fluorophenyl)-2-oxo-ethyl, (4-fluorophenyl)-2-oxo-ethyl, (3,4-difluorophenyl)-2-oxo-ethyl, (2,3-dihydrobenzo[b][1,4]dioxin-6-yl)-2-oxo-ethyl, (2-oxo-2-(4-(pyrrolidin-1-yl)phenyl)ethyl, 2-oxo-2-(4-(trifluoromethoxy)-phenylethyl.

In particular $R^2$ is an unsubstituted or substituted 2,3-dihydroxypropyl, for example $R^2$ is 3-methoxy-2-hydroxypropyl, 3-(benzyloxy)-2-hydroxypropyl, 3-(allyloxy)-2-hydroxypropyl, 3-tert-butoxy-2-hydroxypropyl, 3-phenoxy-2-hydroxypropyl, 3-(4-methoxyphenoxy)-2-hydroxypropyl, 2-hydroxy-3-(4-fluorophenoxy)-propyl, 3-furan-2-yl-methoxy-2-hydroxypropyl. $R^2$ may be unsubstituted or substituted (R)-2,3-dihydroxypropyl or (S)-2,3-dihydroxypropyl.

In particular $R^2$ is an unsubstituted or substituted 2-hydroxypropyl, 2-hydroxy-3-phenylpropyl, 2-hydroxy-2-methylpropyl, 2-hydroxy-3,3,3-trifluoropropyl, 2-hydroxy-3,3-dimethylbutyl, 2-hydroxypentyl.

$R^2$ may be an alkyl bearing at least one carboxylic acid, in particular on the end of the chain, such as acetic acid, propionic acid, propanedioic acid, such as 1,3-propanedioic acid.

$R^2$ may be —CO-alkyl, —CO-alkene, —CO-carbocycle, —CO-heterocycle, optionally substituted and/or bearing at least one alcohol, ketone, ether, ester or acid function. Among the possible substitutions of $R^2$ the following can be cited alkyl, such as methyl or ethyl, alkoxy, such as methoxy, halogen atoms, such as fluoro, chloro, bromo, and alkylenedioxy, such as —OCH$_2$O— and —OCH$_2$CH$_2$O—.

$R^2$ may thus represent acetyl, cyclobutylcarbonyl, benzoyl, furancarbonyl, nicotinoyl, picolinoyl, phenylacetyl, isoxazole-5-carbonyl, isoxazole-4-carbonyl, isoxazole-3-carbonyl, 1,3-oxazol-4-carbonyl, 1H-pyrazole-5-carbonyl, pyrazin-2-carbonyl, in particular 4-fluorobenzoyl, 1-nicotinoyl, 5-phenyl-1,3-oxazol-4-carbonyl, 5-methyl-isoxazole-3-carbonyle, 1,3-dimethyl-1H-pyrazole-5-carbonyl, 3,5-dimethyl-isoxazole-4-carbonyl, 2-methoxyacetyl, 2-phenoxyacetyl, 1-furan-2-carbonyl or (4-fluorophenyl)-acetyl.

$R^2$ may represent alkylsulfone or arylsulfone, optionally substituted, in particular $R^2$ is mesyl or tosyl.

Following another embodiment, $R^1$ and/or $R^2$ do not represent an alkylsulfone, in particular a mesyl group.

Following another embodiment, $R^1$ and/or $R^2$ do not represent an arylsulfone, in particular a tosyl group.

In particular $Z^3$, $Z^4$, $Z^7$, $Z^8$, $Z^9$ and $Z^{10}$ represent H.

Following an embodiment, $Z^3$ and $Z^4$ represent independently H, alkyl, cycloalkyl, alkene, cycloalkene, alkyne, optionally bearing at least one halogen atom and/or at least one function chosen from alcohol, ether, amine, amide, ketone and ester, or some of these species form together a carbocycle or an heterocycle.

In particular $Z^3$ and $Z^4$ represent each an alkyl, more particularly they represent the same alkyl, i.e. as a gem dialkyl.

In particular $Z^3$ and $Z^4$ taken together represent a cycloalkyl, i.e. a spiro function, more particularly they represent a cyclopropyl, a cyclobutyl, a cyclopentyl, a cyclohexyl, a cycloheptyl or a cycloheptyl.

In particular, $Z^3$ and $Z^4$ may represent each an aryl, an arylalkyl or an alkylaryl.

More particularly, $Z^3$ and $Z^4$ do not represent a group comprising, or consisting of, an aryl, in particular such as phenyl, benzyl, substituted phenyl and substituted benzyl. More particularly, $Z^3$ and/or $Z^4$ do not represent an halogen atom.

In particular X is —C($Z^{11}$)=C($Z^{12}$)—, —N=C($Z^{13}$)— or —C($Z^{13}$)=N—. More particularly X is —C($Z^{13}$)=N— or —C($Z^{11}$)=C($Z^{12}$)—.

$Z^{11}$ and $Z^{12}$ may represent H.

$Z^{13}$ may represent H.

In particular $Z^1$ and $Z^{11}$ form together —OCH$_2$CH$_2$O—, and more particularly $Z^2$ and $Z^{12}$ represent each an H atom.

$Z^1$ and $Z^2$ may represent independently H, halogen atom, in particular chosen from bromine, chlorine and fluorine, alkoxy and alkenyloxy, optionally substituted by one or more halogen atom, more particularly fluorine, and even more particularly methoxy, ethoxy, propoxy, fluoromethoxy, difluoromethoxy, trifluoromethoxy, allyloxy, or $Z^1$ and $Z^2$ form together an heterocycloalkyl, in particular bearing two O atoms within the cycle, more particularly chosen from —OCH$_2$O— or —OCH$_2$CH$_2$O—.

More particularly $Z^1$ and $Z^2$ represent H, $Z^2$ is H or difluoromethoxy and $Z^1$ is chosen from halogen atom, in particular chosen from bromine, chlorine and fluorine, methoxy and difluoromethoxy, or $Z^2$ is methoxy and $Z^1$ is allyloxy.

Following an embodiment, the invention has for subject matter a compound corresponding to formula II:

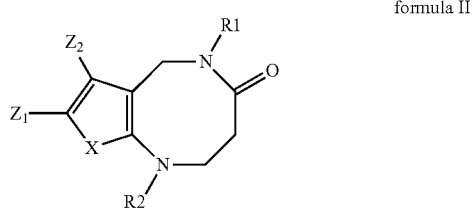

formula II wherein X, $R^1$, $R^2$, $Z^1$ and $Z^2$ are as defined above.

In a particular embodiment the 4-oxo-[1,5]-diazocin corresponds to formula II:

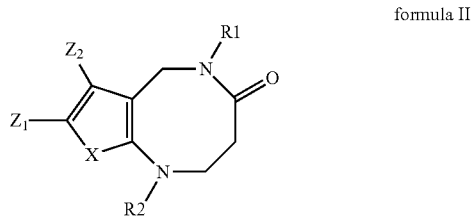

formula II wherein
X is —CH=CH—,
$Z^2$ is H or alkoxy, in particular haloalkoxy and methoxy,
$R^1$ is cycloalkyl, in particular cyclopropyl or cyclopentyl,
$Z^1$ is halogen, in particular F or Cl, alkyl or alkoxy, optionally substituted, in particular with halogen, such as methoxy and difluoromethoxy, and
$R^2$ is an alkyl bearing at least one free alcohol function, in particular chosen from 3-benzyloxy-2-hydroxypropyl, 2-hydroxy-3,3-dimethylbutyl, 4-chlorophenyl-2-hydroxyethyl, in particular (R)-4-chlorophenyl-2-hydroxyethyl, 4-trifluoromethoxyphenyl-2-hydroxyethyl and 3-fluorophenyl-2-hydroxyethyl, a heterocyclecarbonyl forming an amide bond with the N atom, in particular isoxazole-5-carbonyl, pyrazin-2-carbonyl, 3-methyl-isoxazol-5-carbonyl or a carbocyclecarbonyl forming an amide bond with the N atom, in particular cyclobutylcarbonyl.

In a more particular embodiment the 4-oxo-[1,5]-diazocin corresponds to formula II wherein:
X is —CH=CH—,
$Z^2$ is H,
$R^1$ is alkyl, such as ethyl, or cycloalkyl, in particular cyclopropyl and cyclopentyl,
$Z^1$ is halogen, in particular F or Cl, or methoxy, and
$R^2$ is an alkyl bearing at least one free alcohol function, in particular chosen from 3-benzyloxy-2-hydroxypropyl, 3-benzyloxy-(R)-2-hydroxypropyl, 2-hydroxy-3,3-dimethylbutyl, 4-chlorophenyl-2-hydroxyethyl, in particular (R)-4-chlorophenyl-2-hydroxyethyl, 4-trifluoromethoxyphenyl-2-hydroxyethyl and 3-fluorophenyl-2-hydroxyethyl.

In a more particular embodiment the 4-oxo-[1,5]-diazocin corresponds to formula II wherein:
X is —CH=CH—,
$Z^2$ is alkoxy, in particular allyloxy,
$R^1$ is alkyl, such as ethyl and cyclopropylmethyl,
$Z^1$ is halogen, in particular F or Cl, or methoxy, and
$R^2$ is an alkyl bearing at least one free alcohol function, in particular chosen from 3-benzyloxy-2-hydroxypropyl, 2-hydroxy-3,3-dimethylbutyl, 4-chlorophenyl-2-hydroxyethyl, in particular (R)-4-chlorophenyl-2-hydroxyethyl, 4-trifluoromethoxyphenyl-2-hydroxyethyl and 3-fluorophenyl-2-hydroxyethyl, and a heterocyclecarbonyl forming an amide bond with the N atom, in particular isoxazole-5-carbonyl, pyrazin-2-carbonyl, 3-methyl-isoxazol-5-carbonyl, in particular isoxazole-5-carbonyl.

In a more particular embodiment the 4-oxo-[1,5]-diazocin corresponds to formula II wherein:
X is —CH=CH—,
$Z^2$ is H,
$R^1$ is cycloalkyl, in particular cyclopropyl,
$Z^1$ is difluoromethoxy,
$R^2$ is a heterocyclecarbonyl forming an amide bond with the N atom, in particular isoxazole-5-carbonyl, pyrazin-2-carbonyl, 3-methyl-isoxazol-5-carbonyl.

In a more particular embodiment the 4-oxo-[1,5]-diazocin corresponds to formula II wherein:
X is —CH=CH—,
$Z^2$ is difluoromethoxy,
$R^1$ is cycloalkyl, in particular cyclopropyl,
$Z^1$ is methoxy, and
$R^2$ is a heterocyclecarbonyl forming an amide bond with the N atom, in particular isoxazole-5-carbonyl, pyrazin-2-carbonyl, 3-methyl-isoxazol-5-carbonyl.

In a more particular embodiment the 4-oxo-[1,5]-diazocin corresponds to formula II wherein:
X is —CH=CH—,
$Z^2$ is H,
$R^1$ is an alkene, in particular methyl-but-2-enyl, an alkyne, in particular pent-2-ynyl, an aryl, an arylalkyl or an alkylaryl, in particular an alkylaryl, such as a benzyl group,
$Z^1$ is H or alkoxy, in particular methoxy, and
$R^2$ is a heterocyclecarbonyl forming an amide bond with the N atom, in particular isoxazole-5-carbonyl, pyrazin-2-carbonyl, 3-methyl-isoxazol-5-carbonyl, more particularly isoxazole-5-carbonyl.

In a more particular embodiment the 4-oxo-[1,5]-diazocin corresponds to formula II wherein:
X is —CH=CH—,
$Z^2$ is H,
$R^1$ is cycloalkyl, in particular cyclopropyl,
$Z^1$ is halogen, in particular chlorine, and
$R^2$ is a heterocyclecarbonyl forming an amide bond with the N atom, in particular isoxazole-5-carbonyl, pyrazin-2-carbonyl, 3-methyl-isoxazol-5-carbonyl.

In a more particular embodiment the 4-oxo-[1,5]-diazocin corresponds to formula II wherein:
X is —CH=CH—,
$R^1$ is alkyl, such as ethyl, or cycloalkyl, in particular cyclopropyl and cyclopentyl,
$Z^1$ and $Z^2$ represent H, and
$R^2$ represents unsubstituted or substituted 2-hydroxyalkyl, in particular 2-hydroxypropyl.

In a more particular embodiment the 4-oxo-[1,5]-diazocin corresponds to formula II wherein:
X is —CH=CH—,
$R^1$ is alkyl, in particular bearing one ester function, such as ethylacetate,
$Z^1$ and $Z^2$ represent H, and
$R^2$ represents H.

In a particular embodiment the 4-oxo-[1,5]-diazocin corresponds to formula II wherein:

X is —CH=CH—

$R^1$ is alkyl, for example ethyl or cyclopropylmethyl, or cycloalkyl, in particular cyclopropyl, $Z^1$ and $Z^2$ form together a carbocycle or an heterocycle, in particular —OCH$_2$O— or —OCH$_2$CH$_2$O—, and $R^2$ is a heterocyclecarbonyl forming an amide bond with the N atom, in particular isoxazole-5-carbonyl, pyrazin-2-carbonyl, 3-methyl-isoxazol-5-carbonyl, or an unsubstituted or substituted hydroxyalkyl, in particular 2-hydroxypropyl, such as 2-hydroxy-3-phenylpropyl, 2-hydroxy-3-tertbutoxy, 2-hydroxy-3-allyloxy, 2-hydroxy-2-methylpropyl, 2-hydroxy-3,3,3-trifluoropropyl, 2-hydroxy-3,3-dimethylbutyl or 2-hydroxypentyl.

In a more particular embodiment the 4-oxo-[1,5]-diazocin corresponds to formula II wherein:

X is —CH=CH—, $R^1$ is alkyl or cycloalkyl, in particular cyclopropyl, $Z^1$ and $Z^2$ form together a carbocycle or an heterocycle, in particular —OCH$_2$O— or —OCH$_2$CH$_2$O—, and $R^2$ is a heterocyclecarbonyl forming an amide bond with the N atom, in particular isoxazole-5-carbonyl, pyrazin-2-carbonyl, 3-methyl-isoxazol-5-carbonyl.

In a more particular embodiment the 4-oxo-[1,5]-diazocin corresponds to formula II wherein:

X is —CH=CH—, $R^1$ is alkyl or cycloalkyl, in particular cyclopropyl and cyclopentyl, $Z^1$ and $Z^2$ form together a carbocycle or an heterocycle, in particular —OCH$_2$O— or —OCH$_2$CH$_2$O—, and $R^2$ is H.

In a more particular embodiment the 4-oxo-[1,5]-diazocin corresponds to formula II wherein:

X is —CH=CH—, $R^1$ is alkyl or cycloalkyl, in particular cyclopropyl, $Z^1$ and $Z^2$ form together a carbocycle or an heterocycle, in particular —OCH$_2$O— or —OCH$_2$CH$_2$O—, and $R^2$ is an unsubstituted or substituted 2-hydroxypropyl, such as 2-hydroxy-3-phenylpropyl, 2-hydroxy-2-methylpropyl, 2-hydroxy-3,3,3-trifluoropropyl, 2-hydroxyl-3,3-dimethylbutyl or 2-hydroxypentyl.

In another embodiment the 4-oxo-[1,5]-diazocin corresponds to formula II wherein:

X is —CH=N—, $Z^1$ and $Z^2$ represent H, $R^1$ is alkyl or cycloalkyl, in particular cyclopropyl, and $R^2$ is an alkyl bearing a ketone function, in particular forming an amide bond, more particularly 2-(4-fluorophenyl)-acetyl.

The compound of formula (I) can be chosen from:

5-cyclopropyl-8-methoxy-2,3,5,6-tetrahydrobenzo[b][1,5]diazocin-4(1H)-one, 5-cyclopropyl-1-(2-hydroxy-3-phenoxypropyl)-8-methoxy-2,3,5,6-tetrahydrobenzo[b][1,5]diazocin-4(1H)-one, 1-(4-chlorophenethyl)-5-cyclopropyl-8-methoxy-2,3,5,6-tetrahydrobenzo[b][1,5]diazocin-4(1H)-one, 5-cyclopropyl-8-methoxy-1-(5-methylisoxazole-3-carbonyl)-2,3,5,6-tetrahydrobenzo[b][1,5]diazocin-4(1H)-one, 5-cyclopropyl-1-(2-(4-fluorophenyl)-2-oxoethyl)-8-methoxy-2,3,5,6-tetrahydrobenzo[b][1,5]diazocin-4(1H)-one, 5-cyclopropyl-1-(2-(4-fluorophenyl)-2-hydroxyethyl)-8-methoxy-2,3,5,6-tetrahydrobenzo[b][1,5]diazocin-4(1H)-one, 8-bromo-5-cyclopropyl-2,3,5,6-tetrahydrobenzo[b][1,5]diazocin-4(1H)-one, 5-cyclopropyl-8-fluoro-2,3,5,6-tetrahydrobenzo[b][1,5]diazocin-4(1H)-one, 5-cyclopropyl-2,3,5,6-tetrahydropyrido[2,3-b][1,5]diazocin-4(1H)-one, 8-fluoro-2,3,5,6-tetrahydrobenzo[b][1,5]diazocin-4(1H)-one, 5-cyclopropyl-8-methoxy-1-(2-oxo-2-phenylethyl)-2,3,5,6-tetrahydrobenzo[b][1,5]diazocin-4(1H)-one, 5-cyclopropyl-1-(2-(2,5-di methoxyphenyl)-2-oxoethyl)-8-methoxy-2,3,5,6-tetrahydrobenzo[b][1,5]diazocin-4(1H)-one, 5-cyclopropyl-8-methoxy-1-(2-(2-methoxyphenyl)-2-oxoethyl)-2,3,5,6-tetrahydrobenzo[b][1,5]diazocin-4(1H)-one, 1-(2-(4-chlorophenyl)-2-oxoethyl)-5-cyclopropyl-8-methoxy-2,3,5,6-tetrahydrobenzo[b][1,5]diazocin-4(1H)-one, 5-cyclopropyl-1-(2-(2,3-dihydrobenzo[b][1,4]dioxin-6-yl)-2-oxoethyl)-8-methoxy-2,3,5,6-tetrahydrobenzo[b][1,5]diazocin-4(1H)-one, 5-cyclopropyl-8-methoxy-1-(2-oxo-2-(4-(pyrrolidin-1-yl)phenyl)ethyl)-2,3,5,6-tetrahydrobenzo[b][1,5]diazocin-4(1H)-one, 5-cyclopropyl-1-(2-hydroxy-2-phenylethyl)-8-methoxy-2,3,5,6-tetrahydrobenzo[b][1,5]diazocin-4(1H)-one, (R)-1-(3-(benzyloxy)-2-hydroxypropyl)-5-cyclopropyl-8-methoxy-2,3,5,6-tetrahydrobenzo[b][1,5]diazocin-4(1H)-one, (R)-1-(3-(benzyloxy)-2-hydroxypropyl)-5-cyclopropyl-8-fluoro-2,3,5,6-tetrahydrobenzo[b][1,5]diazocin-4(1H)-one, 5-cyclopropyl-8-methoxy-1-(2-(3-methoxyphenyl)-2-oxoethyl)-2,3,5,6-tetrahydrobenzo[b][1,5]diazocin-4(1H)-one, 5-cyclopropyl-8-methoxy-1-(2-(4-methoxyphenyl)-2-oxoethyl)-2,3,5,6-tetrahydrobenzo[b][1,5]diazocin-4(1H)-one, 5-cyclopropyl-1-(2-(3-fluorophenyl)-2-oxoethyl)-8-methoxy-2,3,5,6-tetrahydrobenzo[b][1,5]diazocin-4(1H)-one, 5-cyclopropyl-8-methoxy-1-(2-oxo-2-(4-(trifluoromethoxy)phenyl)ethyl)-2,3,5,6-tetrahydrobenzo[b][1,5]diazocin-4(1H)-one, 5-cyclopropyl-1-(2-(3,4-difluorophenyl)-2-oxoethyl)-8-methoxy-2,3,5,6-tetrahydrobenzo[b][1,5]diazocin-4(1H)-one, 5-cyclopropyl-1-(2-(2,5-dimethoxyphenyl)-2-hydroxyethyl)-8-methoxy-2,3,5,6-tetrahydrobenzo[b][1,5]diazocin-4(1H)-one, 5-cyclopropyl-1-(2-hydroxy-2-(2-methoxyphenyl)ethyl)-8-methoxy-2,3,5,6-tetrahydrobenzo[b][1,5]diazocin-4(1H)-one, 1-(2-(4-chlorophenyl)-2-hydroxyethyl)-5-cyclopropyl-8-methoxy-2,3,5,6-tetrahydrobenzo[b][1,5]diazocin-4(1H)-one, 5-cyclopropyl-1-(2-hydroxy-2-(4-(pyrrolidin-1-yl)phenyl)ethyl)-8-methoxy-2,3,5,6-tetrahydrobenzo[b][1,5]diazocin-4(1H)-one, 5-cyclopropyl-1-(2-(2,3-dihydrobenzo[b][1,4]dioxin-6-yl)-2-hydroxyethyl)-8-methoxy-2,3,5,6-tetrahydrobenzo[b][1,5]diazocin-4(1H)-one 5-cyclopropyl-1-(2-hydroxy-2-(3-methoxyphenyl)ethyl)-8-methoxy-2,3,5,6-tetrahydrobenzo[b][1,5]diazocin-4(1H)-one, 5-cyclopropyl-1-(2-(3-fluorophenyl)-2-hydroxyethyl)-8-methoxy-2,3,5,6-tetrahydrobenzo[b][1,5]diazocin-4(1H)-one, 5-cyclopropyl-1-(2-hydroxy-2-(4-methoxyphenyl)ethyl)-8-methoxy-2,3,5,6-tetrahydrobenzo[b][1,5]diazocin-4(1H)-one, 5-cyclopropyl-1-(2-hydroxy-2-(4-(trifluoromethoxy)phenyl)ethyl)-8-methoxy-2,3,5,6-tetrahydrobenzo[b][1,5]diazocin-4(1H)-one, 5-cyclopropyl-1-(2-(3,4-difluorophenyl)-2-hydroxyethyl)-8-methoxy-2,3,5,6-tetrahydrobenzo[b][1,5]diazocin-4(1H)-one, 5-cyclopropyl-8-fluoro-1-(2-oxo-2-phenylethyl)-2,3,5,6-tetrahydrobenzo[b][1,5]diazocin-4(1H)-one, 5-cyclopropyl-8-fluoro-1-(2-(2-methoxyphenyl)-2-oxoethyl)-2,3,5,6-tetrahydrobenzo[b][1,5]diazocin-4(1H)-one, 5-cyclopropyl-8-fluoro-1-(2-(3-methoxyphenyl)-2-oxoethyl)-2,3,5,6-tetrahydrobenzo[b][1,5]diazocin-4(1H)-one, 5-cyclopropyl-8-fluoro-1-(2-(4-methoxyphenyl)-2-oxoethyl)-2,3,5,6-tetrahydrobenzo[b][1,5]diazocin-4(1H)-one, 5-cyclopropyl-1-(2-(2,5-dimethoxyphenyl)-2-oxoethyl)-8-fluoro-2,3,5,6-tetrahydrobenzo[b][1,5]diazocin-4(1H)-one, 5-cyclopropyl-8-fluoro-1-(2-(4-fluorophenyl)-2-oxoethyl)-2,3,5,6-tetrahydrobenzo[b][1,5]diazocin-4(1H)-one, 5-cyclopropyl-8-fluoro-1-(2-(3-fluorophenyl)-2-oxoethyl)-2,3,5,6-tetrahydrobenzo[b][1,5]diazocin-4(1H)-one, 5-cyclopropyl-8-fluoro-1-(2-oxo-2-(4-(trifluoromethoxy)phenyl)ethyl)-2,3,5,6-tetrahydrobenzo[b][1,5]diazocin-4(1H)-one, 5-cyclopropyl-1-(2-(3,4-difluorophenyl)-2-oxoethyl)-8-fluoro-2,3,5,6-tetrahydrobenzo[b][1,5]diazocin-4(1H)-one, 1-(2-(4-chlorophenyl)-2-oxoethyl)-5-cyclopropyl-8-fluoro-2,3,5,6-tetrahydrobenzo[b][1,5]diazocin-4(1H)-one, 5-cyclopropyl-1-(2-(2,5-dimethoxyphenyl)-2-hydroxyethyl)-8-fluoro-2,3,5,6-tetrahydrobenzo[b][1,5]diazocin-4(1H)-one, 5-cyclopropyl-8-fluoro-1-(2-(4-fluorophenyl)-2-hydroxyethyl)-2,3,5,6-tetrahydrobenzo[b][1,5]diazocin-4(1H)-one, 5-cyclopropyl-8-fluoro-1-(2-(3-fluorophenyl)-2-hydroxyethyl)-2,3,5,6-tetrahydrobenzo[b][1,5]diazocin-4(1H)-one, 5-cyclopropyl-8-fluoro-1-(2-hydroxy-2-(4-(trifluoromethoxy)phenyl)ethyl)-2,3,5,6-tetrahydrobenzo[b][1,5]diazocin-4(1H)-one, 5-cyclopropyl-1-(2-(3,4-difluorophenyl)-2-hydroxyethyl)-8-fluoro-2,3,5,6-tetrahydrobenzo[b][1,5]diazocin-4(1H)-one, 1-(2-(4-chlorophenyl)-2-hydroxyethyl)-5-cyclopropyl-8-fluoro-2,3,5,6-tetrahydrobenzo[b][1,5]diazocin-4(1H)-one, 5-cyclopropyl-1-(2-hydroxy-3-(4-methoxyphenoxy)propyl)-8-methoxy-2,3,5,6-tetrahydrobenzo[b][1,5]diazocin-4(1H)-one, 5-cyclopropyl-8-fluoro-1-(2-hydroxy-3-phenoxypropyl)-2,3,5,6-tetrahydrobenzo[b][1,5]diazocin-4(1H)-one, 5-cyclopropyl-8-fluoro-1-(2-hydroxy-3-(4-methoxyphenoxy)propyl)-2,3,5,6-tetrahydrobenzo[b][1,5]diazocin-4(1H)-one, 8-methoxy-2,3,5,6-tetrahydrobenzo[b][1,5]diazocin-4(1H)-one, 5-cyclopropyl-1-(2-(2,3-dihydrobenzo[b][1,4]dioxin-6-yl)-2-oxoethyl)-8-fluoro-2,3,5,6-tetrahydrobenzo[b][1,5]diazocin-4(1H)-one, 5-cyclopropyl-8-fluoro-1-(2-oxo-2-(4-(pyrrolidin-1-yl)phenyl)ethyl)-2,3,5,6-tetrahydrobenzo[b][1,5]diazocin-4(1H)-one, 5-cyclopropyl-8-fluoro-1-(2-hydroxy-2-(2-methoxyphenyl)ethyl)-2,3,5,6-tetrahydrobenzo[b][1,5]diazocin-4(1H)-one, 5-cyclopropyl-8-fluoro-1-(2-hydroxy-2-(3-methoxyphenyl)ethyl)-2,3,5,6-tetrahydrobenzo[b][1,5]diazocin-4(1H)-one, 5-cyclopropyl-8-fluoro-1-(2-hydroxy-2-(4-methoxyphenyl)ethyl)-2,3,5,6-tetrahydrobenzo[b][1,5]diazocin-4(1H)-one, 5-cyclopropyl-1-(2-(2,3-dihydrobenzo[b][1,4]dioxin-6-yl)-2-hydroxyethyl)-8-fluoro-2,3,5,6-tetrahydrobenzo[b][1,5]diazocin-4(1H)-one, 5-cyclopropyl-8-fluoro-1-(2-hydroxy-2-phenylethyl)-2,3,5,6-tetrahydrobenzo[b][1,5]diazocin-4(1H)-one, 5-cyclopropyl-2,3,5,6-tetrahydropyrido[3,4-b][1,5]diazocin-4(1H)-one, 2-(7-(allyloxy)-5-cyclopentyl-8-methoxy-4-oxo-3,4,5,6-tetrahydrobenzo[b][1,5]diazocin-1(2H)-yl)acetic acid, 5-cyclopropyl-8-fluoro-1-(2-hydroxy-2-(4-(pyrrolidin-1-yl)phenyl)ethyl)-2,3,5,6-tetrahydrobenzo[b][1,5]diazocin-4(1H)-one, 5-cyclopropyl-8-fluoro-1-(3-(4-fluorophenoxy)-2-hydroxypropyl)-2,3,5,6-tetrahydrobenzo[b][1,5]diazocin-4(1H)-one, (S)-1-(3-(benzyloxy)-2-hydroxypropyl)-5-cyclopropyl-8-fluoro-2,3,5,6-tetrahydrobenzo[b][1,5]diazocin-4(1H)-one, (S)-1-(3-(benzyloxy)-2-hydroxypropyl)-5-cyclopropyl-8-methoxy-2,3,5,6-tetrahydrobenzo[b][1,5]diazocin-4(1H)-one, (R)-5-cyclopropyl-1-(2,3-dihydroxypropyl)-8-methoxy-2,3,5,6-tetrahydrobenzo[b][1,5]diazocin-4(1H)-one, 5-cyclopropyl-8-fluoro-1-(4-fluorobenzoyl)-2,3,5,6-tetrahydrobenzo[b][1,5]diazocin-4(1H)-one, 5-cyclopropyl-8-fluoro-1-nicotinoyl-2,3,5,6-tetrahydrobenzo[b][1,5]diazocin-4(1H)-one, 5-cyclopropyl-8-fluoro-1-(2-(4-fluorophenyl)acetyl)-2,3,5,6-tetrahydrobenzo[b][1,5]diazocin-4(1H)-one, 1-benzyl-5-cyclopropyl-8-fluoro-2,3,5,6-tetrahydrobenzo[b][1,5]diazocin-4(1H)-one, 5-cyclopropyl-8-fluoro-1-phenethyl-2,3,5,6-tetrahydrobenzo[b][1,5]diazocin-4(1H)-one, 5-cyclopropyl-8-fluoro-1-(3-phenylpropyl)-2,3,5,6-tetrahydrobenzo[b][1,5]diazocin-4(1H)-one, 5-cyclopropyl-1-(4-fluorobenzoyl)-2,3,5,6-tetrahydropyrido[2,3-b][1,5]diazocin-4(1H)-one, 5-cyclopropyl-1-(2-(4-fluorophenyl)acetyl)-2,3,5,6-tetrahydropyrido[2,3-b][1,5]diazocin-4(1H)-one, 5-cyclopropyl-1-nicotinoyl-2,3,5,6-tetrahydropyrido[2,3-b][1,5]diazocin-4(1H)-one 8-chloro-5-cyclopropyl-2,3,5,6-tetrahydrobenzo[b][1,5]diazocin-4(1H)-one, (R)-1-(3-(benzyloxy)-2-hydroxypropyl)-8-chloro-5-cyclopropyl-2,3,5,6-tetrahydrobenzo[b][1,5]diazocin-4(1H)-one, 11-cyclopropyl-2,3,8,9,11,12-hexahydro[1,4]dioxino[2,3-h][1,5]benzodiazocin-10(7H)-one, 8-chloro-5-cyclopropyl-1-(2-hydroxy-3-phenoxypropyl)-2,3,5,6-tetrahydrobenzo[b][1,5]diazocin-4(1H)-one, 8-chloro-1-(2-(4-chlorophenyl)-2-oxoethyl)-5-cyclopropyl-2,3,5,6-tetrahydrobenzo[b][1,5]diazocin-4(1H)-one,
8-chloro-5-cyclopropyl-1-(2-(3-fluorophenyl)-2-oxoethyl)-2,3,5,6-tetrahydrobenzo[b][1,5]diazocin-4(1H)-one,
5-cyclopropyl-1-(isoxazole-5-carbonyl)-8-methoxy-2,3,5,6-tetrahydrobenzo[b][1,5]diazocin-4(1H)-one,
8-chloro-1-(2-(4-chlorophenyl)-2-hydroxyethyl)-5-cyclopropyl-2,3,5,6-tetrahydrobenzo[b][1,5]diazocin-4(1H)-one,
8-chloro-5-cyclopropyl-1-(2-(3-fluorophenyl)-2-hydroxyethyl)-2,3,5,6-tetrahydrobenzo[b][1,5]diazocin-4(1H)-one,
7-[(2R)-3-(benzyloxy)-2-hydroxypropyl]-11-cyclopropyl-2,3,8,9,11,12-hexahydro[1,4]dioxino[2,3-h][1,5]benzodiazocin-10(7H)-one,
(R)-1-(3-(4-chlorophenoxy)-2-hydroxypropyl)-5-cyclopropyl-8-methoxy-2,3,5,6-tetrahydrobenzo[b][1,5]diazocin-4(1H)-one,
(S)-1-(3-(4-chlorophenoxy)-2-hydroxypropyl)-5-cyclopropyl-8-methoxy-2,3,5,6-tetrahydrobenzo[b][1,5]diazocin-4(1H)-one,
11-cyclopropyl-7-(isoxazol-5-ylcarbonyl)-2,3,8,9,11,12-hexahydro[1,4]dioxino[2,3-h][1,5]benzodiazocin-10(7H)-one,
11-cyclopropyl-7-[(5-phenyl-1,3-oxazol-4-yl)carbonyl]-2,3,8,9,11,12-hexahydro[1,4]dioxino[2,3-h][1,5]benzodiazocin-10(7H)-one,
11-cyclopropyl-7-[2-(3-fluorophenyl)-2-oxoethyl]-2,3,8,9,11,12-hexahydro[1,4]dioxino[2,3-h][1,5]benzodiazocin-10(7H)-one,
7-[2-(4-chlorophenyl)-2-oxoethyl]-11-cyclopropyl-2,3,8,9,11,12-hexahydro[1,4]dioxino[2,3-h][1,5]benzodiazocin-10(7H)-one,
11-cyclopropyl-7-(2-hydroxy-3-phenoxypropyl)-2,3,8,9,11,12-hexahydro[1,4]dioxino[2,3-h][1,5]benzodiazocin-10(7H)-one,
11-cyclopropyl-7-[2-(3-fluorophenyl)-2-hydroxyethyl]-2,3,8,9,11,12-hexahydro[1,4]dioxino[2,3-h][1,5]benzodiazocin-10(7H)-one,
7-[2-(4-chlorophenyl)-2-hydroxyethyl]-11-cyclopropyl-2,3,8,9,11,12-hexahydro[1,4]dioxino[2,3-h][1,5]benzodiazocin-10(7H)-one,
5-cyclopropyl-8-methoxy-1-(5-phenyloxazole-4-carbonyl)-2,3,5,6-tetrahydrobenzo[b][1,5]diazocin-4(1H)-one,
5-cyclopropyl-1-(1,3-dimethyl-1H-pyrazole-5-carbonyl)-8-methoxy-2,3,5,6-tetrahydrobenzo[b][1,5]diazocin-4(1H)-one,
5-cyclopropyl-1-(3,5-dimethylisoxazole-4-carbonyl)-8-methoxy-2,3,5,6-tetrahydrobenzo[b][1,5]diazocin-4(1H)-one,
5-cyclopropyl-8-methoxy-1-(pyrazine-2-carbonyl)-2,3,5,6-tetrahydrobenzo[b][1,5]diazocin-4(1H)-one,
5-cyclopropyl-1-(isoxazole-5-carbonyl)-2,3,5,6-tetrahydropyrido[2,3-b][1,5]diazocin-4(1H)-one,
5-cyclopropyl-1-(5-phenyloxazole-4-carbonyl)-2,3,5,6-tetrahydropyrido[2,3-b][1,5]diazocin-4(1H)-one,
5-cyclopropyl-1-(5-methylisoxazole-3-carbonyl)-2,3,5,6-tetrahydropyrido[2,3-b][1,5]diazocin-4(1H)-one,
5-cyclopropyl-1-(1,3-dimethyl-1H-pyrazole-5-carbonyl)-2,3,5,6-tetrahydropyrido[2,3-b][1,5]diazocin-4(1H)-one,
5-cyclopropyl-1-(3,5-dimethylisoxazole-4-carbonyl)-2,3,5,6-tetrahydropyrido[2,3-b][1,5]diazocin-4(1H)-one,
5-cyclopropyl-1-(pyrazine-2-carbonyl)-2,3,5,6-tetrahydropyrido[2,3-b][1,5]diazocin-4(1H)-one,
5-cyclopropyl-8-(difluoromethoxy)-2,3,5,6-tetrahydrobenzo[b][1,5]diazocin-4(1H)-one,
(R)-5-cyclopropyl-1-(3-(3-fluorophenoxy)-2-hydroxypropyl)-8-methoxy-2,3,5,6-tetrahydrobenzo[b][1,5]diazocin-4(1H)-one,
(S)-5-cyclopropyl-1-(3-(3-fluorophenoxy)-2-hydroxypropyl)-8-methoxy-2,3,5,6-tetrahydrobenzo[b][1,5]diazocin-4(1H)-one,
5-cyclopropyl-8-(difluoromethoxy)-1-(isoxazole-5-carbonyl)-2,3,5,6-tetrahydrobenzo[b][1,5]diazocin-4(1H)-one,
5-cyclopropyl-8-(difluoromethoxy)-1-(5-phenyloxazole-4-carbonyl)-2,3,5,6-tetrahydrobenzo[b][1,5]diazocin-4(1H)-one,
5-cyclopropyl-8-(difluoromethoxy)-1-(5-methylisoxazole-3-carbonyl)-2,3,5,6-tetrahydrobenzo[b][1,5]diazocin-4(1H)-one,
5-cyclopropyl-8-(difluoromethoxy)-1-(1,3-dimethyl-1H-pyrazole-5-carbonyl)-2,3,5,6-tetrahydrobenzo[b][1,5]diazocin-4(1H)-one,
5-cyclopropyl-8-(difluoromethoxy)-1-(3,5-di methylisoxazole-4-carbonyl)-2,3,5,6-tetrahydrobenzo[b][1,5]diazocin-4(1H)-one,
5-cyclopropyl-8-(difluoromethoxy)-1-(pyrazine-2-carbonyl)-2,3,5,6-tetrahydrobenzo[b][1,5]diazocin-4(1H)-one,
(R)-5-cyclopropyl-8-(difluoromethoxy)-1-(3-(3-fluorophenoxy)-2-hydroxypropyl)-2,3,5,6-tetrahydrobenzo[b][1,5]diazocin-4(1H)-one,
(S)-5-cyclopropyl-8-(difluoromethoxy)-1-(3-(3-fluorophenoxy)-2-hydroxypropyl)-2,3,5,6-tetrahydrobenzo[b][1,5]diazocin-4(1H)-one,
(R)-1-(3-(4-chlorophenoxy)-2-hydroxypropyl)-5-cyclopropyl-8-(difluoromethoxy)-2,3,5,6-tetrahydrobenzo[b][1,5]diazocin-4(1H)-one,
(S)-1-(3-(4-chlorophenoxy)-2-hydroxypropyl)-5-cyclopropyl-8-(difluoromethoxy)-2,3,5,6-tetrahydrobenzo[b][1,5]diazocin-4(1H)-one,
5-cyclopropyl-8-fluoro-1-(2-methoxyacetyl)-2,3,5,6-tetrahydrobenzo[b][1,5]diazocin-4(1H)-one,
5-cyclopropyl-8-fluoro-1-(2-phenoxyacetyl)-2,3,5,6-tetrahydrobenzo[b][1,5]diazocin-4(1H)-one,
5-cyclopropyl-8-fluoro-1-(furan-2-carbonyl)-2,3,5,6-tetrahydrobenzo[b][1,5]diazocin-4(1H)-one,
5-cyclopropyl-8-(difluoromethoxy)-2,3,5,6-tetrahydrobenzo[b][1,5]diazocin-4(1H)-one,
11-cyclopropyl-7-((1-methyl-1H-imidazol-4-yl)sulfonyl)-2,3,8,9,11,12-hexahydro-[1,4]dioxino[2',3':3,4]benzo[1,2-b][1,5]diazocin-10(7H)-one,
(R)-7-(3-(4-chlorophenoxy)-2-hydroxypropyl)-11-cyclopropyl-2,3,8,9,11,12-hexahydro-[1,4]dioxino[2',3':3,4]benzo[1,2-b][1,5]diazocin-10(7H)-one,
5-cyclopropyl-7-(difluoromethoxy)-8-methoxy-2,3,5,6-tetrahydrobenzo[b][1,5]diazocin-4(1H)-one,
11-cyclopropyl-7-(pyrazine-2-carbonyl)-2,3,8,9,11,12-hexahydro-[1,4]dioxino[2',3':3,4]benzo[1,2-b][1,5]diazocin-10(7H)-one,
5-cyclopropyl-7-(difluoromethoxy)-8-methoxy-1-(pyrazine-2-carbonyl)-2,3,5,6-tetrahydrobenzo[b][1,5]diazocin-4(1H)-one,
5-cyclopropyl-8-fluoro-1-(pyrazine-2-carbonyl)-2,3,5,6-tetrahydrobenzo[b][1,5]diazocin-4(1H)-one,
8-chloro-5-cyclopropyl-1-picolinoyl-2,3,5,6-tetrahydrobenzo[b][1,5]diazocin-4(1H)-one, 11-cyclopropyl-7-picolinoyl-2,3,8,9,11,12-hexahydro-[1,4]dioxino[2',3':3,4]benzo[1,2-b][1,5]diazocin-10(7H)-one,
8-chloro-5-cyclopropyl-1-(pyrazine-2-carbonyl)-2,3,5,6-tetrahydrobenzo[b][1,5]diazocin-4(1H)-one,
(R)-1-(3-(4-chlorophenoxy)-2-hydroxypropyl)-5-cyclopropyl-7-(difluoromethoxy)-8-methoxy-2,3,5,6-tetrahydrobenzo[b][1,5]diazocin-4(1H)-one,
(R)-8-chloro-1-(3-(4-chlorophenoxy)-2-hydroxypropyl)-5-cyclopropyl-2,3,5,6-tetrahydrobenzo[b][1,5]diazocin-4(1H)-one,
(R)-5-cyclopropyl-8-fluoro-1-(2-hydroxy-3-(4-(methylsulfonyl)phenoxy)propyl)-2,3,5,6-tetrahydrobenzo[b][1,5]diazocin-4(1H)-one,
(R)-8-chloro-5-cyclopropyl-1-(2-hydroxy-3-(4-(methylsulfonyl)phenoxy)propyl)-2,3,5,6-tetrahydrobenzo[b][1,5]diazocin-4(1H)-one,
11-cyclopropyl-7-(3-methylisoxazole-5-carbonyl)-2,3,8,9,11,12-hexahydro-[1,4]dioxino[2',3':3,4]benzo[1,2-b][1,5]diazocin-10(7H)-one,
8-chloro-5-cyclopropyl-1-(3-methylisoxazole-5-carbonyl)-2,3,5,6-tetrahydrobenzo[b][1,5]diazocin-4(1H)-one,
5-cyclopropyl-7-(difluoromethoxy)-8-methoxy-1-(3-methylisoxazole-5-carbonyl)-2,3,5,6-tetrahydrobenzo[b][1,5]diazocin-4(1H)-one,
5-cyclopropyl-8-methoxy-1-(3-methylisoxazole-5-carbonyl)-2,3,5,6-tetrahydrobenzo[b][1,5]diazocin-4(1H)-one,
5-cyclopropyl-8-(difluoromethoxy)-1-(3-methylisoxazole-5-carbonyl)-2,3,5,6-tetrahydrobenzo[b][1,5]diazocin-4(1H)-one,
8-chloro-5-cyclopropyl-1-(2-(4-(difluoromethoxy)phenyl)-2-oxoethyl)-2,3,5,6-tetrahydrobenzo[b][1,5]diazocin-4(1H)-one,
11-cyclopropyl-7-(2-(4-(difluoromethoxy)phenyl)-2-oxoethyl)-2,3,8,9,11,12-hexahydro-[1,4]dioxino[2',3':3,4]benzo[1,2-b][1,5]diazocin-10(7H)-one,
1-(4-chlorophenyl)-2-(5-cyclopropyl-8-fluoro-3,4,5,6-tetrahydrobenzo[b][1,5]diazocin-1(2H)-yl)ethanol,
(S)-11-cyclopropyl-7-(2-hydroxypropyl)-2,3,8,9,11,12-hexahydro-[1,4]dioxino[2',3':3,4]benzo[1,2-b][1,5]diazocin-10(7H)-one,
(S)-8-chloro-5-cyclopropyl-1-(2-hydroxypropyl)-2,3,5,6-tetrahydrobenzo[b][1,5]diazocin-4(1H)-one,
8-chloro-5-cyclopropyl-1-(2-(4-(difluoromethoxy)phenyl)-2-hydroxyethyl)-2,3,5,6-tetrahydrobenzo[b][1,5]diazocin-4(1H)-one,
11-cyclopropyl-7-(2-(4-(difluoromethoxy)phenyl)-2-hydroxyethyl)-2,3,8,9,11,12-hexahydro-[1,4]dioxino[2',3':3,4]benzo[1,2-b][1,5]diazocin-10(7H)-one,
5-(cyclopropylmethyl)-1-(2-(4-fluorophenyl)acetyl)-2,3,5,6-tetrahydropyrido[2,3-b][1,5]diazocin-4(1H)-one,
5-(cyclopropylmethyl)-1-(3-methylisoxazole-5-carbonyl)-2,3,5,6-tetrahydropyrido[2,3-b][1,5]diazocin-4(1H)-one,
5-(cyclopropylmethyl)-1-(pyrazine-2-carbonyl)-2,3,5,6-tetrahydropyrido[2,3-b][1,5]diazocin-4(1H)-one,
5-(cyclopropylmethyl)-1-nicotinoyl-2,3,5,6-tetrahydropyrido[2,3-b][1,5]diazocin-4(1H)-one,
5-benzyl-1-(2-hydroxy-3-phenoxypropyl)-2,3,5,6-tetrahydrobenzo[b][1,5]diazocin-4(1H)-one,
5-benzyl-1-(2,3-dihydroxypropyl)-2,3,5,6-tetrahydrobenzo[b][1,5]diazocin-4(1H)-one,
1-(3-tert-butoxy-2-hydroxypropyl)-5-(cyclopropylmethyl)-2,3,5,6-tetrahydrobenzo[b][1,5]diazocin-4(1H)-one,
5-benzyl-1-(2-hydroxypropyl)-2,3,5,6-tetrahydrobenzo[b][1,5]diazocin-4(1H)-one,
5-benzyl-1-(2-hydroxypentyl)-2,3,5,6-tetrahydrobenzo[b][1,5]diazocin-4(1H)-one,
1-(2-hydroxypropyl)-5-(3-methylbut-2-enyl)-2,3,5,6-tetrahydrobenzo[b][1,5]diazocin-4(1H)-one,
1-(2-hydroxypropyl)-5-(pent-2-ynyl)-2,3,5,6-tetrahydrobenzo[b][1,5]diazocin-4(1H)-one,
5-(cyclopropylmethyl)-1-(2-hydroxypropyl)-2,3,5,6-tetrahydrobenzo[b][1,5]diazocin-4(1H)-one,
5-(3,3-dimethyl-2-oxobutyl)-1-(2-hydroxypropyl)-2,3,5,6-tetrahydrobenzo[b][1,5]diazocin-4(1H)-one,
1-(2-hydroxypropyl)-5-(2-methoxyethyl)-2,3,5,6-tetrahydrobenzo[b][1,5]diazocin-4(1H)-one,
5-allyl-1-(2-hydroxypropyl)-2,3,5,6-tetrahydrobenzo[b][1,5]diazocin-4(1H)-one
1-(2-hydroxypropyl)-5-methyl-2,3,5,6-tetrahydrobenzo[b][1,5]diazocin-4(1H)-one
ethyl 2-(1-(2-hydroxypropyl)-4-oxo-1,2,3,4-tetrahydrobenzo[b][1,5]diazocin-5(6H)-yl)acetate,
5-(cyclopropylmethyl)-1-(2-hydroxy-3-phenoxypropyl)-2,3,5,6-tetrahydrobenzo[b][1,5]diazocin-4(1H)-one,
1-(2-hydroxy-3-phenoxypropyl)-5-(2-methoxyethyl)-2,3,5,6-tetrahydrobenzo[b][1,5]diazocin-4(1H)-one,
1-(2-hydroxypentyl)-5-(3-methylbut-2-enyl)-2,3,5,6-tetrahydrobenzo[b][1,5]diazocin-4(1H)-one,
5-(cyclopropylmethyl)-1-(2-hydroxypentyl)-2,3,5,6-tetrahydrobenzo[b][1,5]diazocin-4(1H)-one,
5-(3,3-dimethyl-2-oxobutyl)-1-(2-hydroxypentyl)-2,3,5,6-tetrahydrobenzo[b][1,5]diazocin-4(1H)-one,
1-(2-hydroxypentyl)-5-(2-methoxyethyl)-2,3,5,6-tetrahydrobenzo[b][1,5]diazocin-4(1H)-one,
1-(2-hydroxypentyl)-5-methyl-2,3,5,6-tetrahydrobenzo[b][1,5]diazocin-4(1H)-one
ethyl 2-(1-(2-hydroxypentyl)-4-oxo-1,2,3,4-tetrahydrobenzo[b][1,5]diazocin-5(6H)-yl)acetate,
5-benzyl-1-(2-hydroxy-3-methoxypropyl)-2,3,5,6-tetrahydrobenzo[b][1,5]diazocin-4(1H)-one,
5-benzyl-1-(3,3,3-trifluoro-2-hydroxypropyl)-2,3,5,6-tetrahydrobenzo[b][1,5]diazocin-4(1H)-one,
5-(cyclopropylmethyl)-1-(2-hydroxy-3-(4-methoxyphenoxy)propyl)-2,3,5,6-tetrahydrobenzo[b][1,5]diazocin-4(1H)-one,
1-(2-hydroxy-3-(4-methoxyphenoxy)propyl)-5-(3-methylbut-2-enyl)-2,3,5,6-tetrahydrobenzo[b][1,5]diazocin-4(1H)-one,
1-(2-hydroxy-3-(4-methoxyphenoxy)propyl)-5-(2-methoxyethyl)-2,3,5,6-tetrahydrobenzo[b][1,5]diazocin-4(1H)-one,
1-(2-hydroxy-3-(4-methoxyphenoxy)propyl)-5-methyl-2,3,5,6-tetrahydrobenzo[b][1,5]diazocin-4(1H)-one,
ethyl 2-(1-(2-hydroxy-3-(4-methoxyphenoxy)propyl)-4-oxo-1,2,3,4-tetrahydrobenzo[b][1,5]diazocin-5(6H)-yl)acetate,
5-benzyl-1-(2-hydroxy-3-(4-methoxyphenoxy)propyl)-2,3,5,6-tetrahydrobenzo[b][1,5]diazocin-4(1H)-one,
5-(3,3-dimethyl-2-oxobutyl)-1-(2-hydroxy-3-(4-methoxyphenoxy)propyl)-2,3,5,6-tetrahydrobenzo[b][1,5]diazocin-4(1H)-one,
1-(3-tert-butoxy-2-hydroxypropyl)-5-(3-methylbut-2-enyl)-2,3,5,6-tetrahydrobenzo[b][1,5]diazocin-4(1H)-one,
5-(cyclopropylmethyl)-1-(2-hydroxy-3-methoxypropyl)-2,3,5,6-tetrahydrobenzo[b][1,5]diazocin-4(1H)-one,
1-(2-hydroxy-3-methoxypropyl)-5-(3-methylbut-2-enyl)-2,3,5,6-tetrahydrobenzo[b][1,5]diazocin-4(1H)-one, 5-allyl-1-(3-tert-butoxy-2-hydroxypropyl)-2,3,5,6-tetrahydrobenzo[b][1,5]diazocin-4(1H)-one,
5-(3,3-dimethyl-2-oxobutyl)-1-(2-hydroxy-3-methoxypropyl)-2,3,5,6-tetrahydrobenzo[b][1,5]diazocin-4(1H)-one,
5-(cyclopropylmethyl)-1-(2-hydroxy-3-phenylpropyl)-2,3,5,6-tetrahydrobenzo[b][1,5]diazocin-4(1H)-one,
1-(2-hydroxy-3-phenylpropyl)-5-(3-methylbut-2-enyl)-2,3,5,6-tetrahydrobenzo[b][1,5]diazocin-4(1H)-one,
1-(2-hydroxy-3-phenylpropyl)-5-(2-methoxyethyl)-2,3,5,6-tetrahydrobenzo[b][1,5]diazocin-4(1H)-one,
1-(2-hydroxy-3-phenylpropyl)-5-methyl-2,3,5,6-tetrahydrobenzo[b][1,5]diazocin-4(1H)-one,
5-benzyl-1-(2-hydroxy-3-phenylpropyl)-2,3,5,6-tetrahydrobenzo[b][1,5]diazocin-4(1H)-one,
1-(2-hydroxy-2-methylpropyl)-5-(2-methoxyethyl)-2,3,5,6-tetrahydrobenzo[b][1,5]diazocin-4(1H)-one,
1-(2-hydroxy-2-methylpropyl)-5-methyl-2,3,5,6-tetrahydrobenzo[b][1,5]diazocin-4(1H)-one,
1-(3-tert-butoxy-2-hydroxypropyl)-5-methyl-2,3,5,6-tetrahydrobenzo[b][1,5]diazocin-4(1H)-one,
5-(cyclopropylmethyl)-1-(3,3,3-trifluoro-2-hydroxypropyl)-2,3,5,6-tetrahydrobenzo[b][1,5]diazocin-4(1H)-one,
5-(3-methylbut-2-enyl)-1-(3,3,3-trifluoro-2-hydroxypropyl)-2,3,5,6-tetrahydrobenzo[b][1,5]diazocin-4(1H)-one,
5-methyl-1-(3,3,3-trifluoro-2-hydroxypropyl)-2,3,5,6-tetrahydrobenzo[b][1,5]diazocin-4(1H)-one,
ethyl 2-(4-oxo-1-(3,3,3-trifluoro-2-hydroxypropyl)-1,2,3,4-tetrahydrobenzo[b][1,5]diazocin-5(6H)-yl)acetate,
ethyl 2-(1-(3-tert-butoxy-2-hydroxypropyl)-4-oxo-1,2,3,4-tetrahydrobenzo[b][1,5]diazocin-5(6H)-yl)acetate,
5-benzyl-1-(3-tert-butoxy-2-hydroxypropyl)-2,3,5,6-tetrahydrobenzo[b][1,5]diazocin-4(1H)-one,
1-(3-(furan-2-ylmethoxy)-2-hydroxypropyl)-5-(3-methylbut-2-enyl)-2,3,5,6-tetrahydrobenzo[b][1,5]diazocin-4(1H)-one,
1-(3-(furan-2-ylmethoxy)-2-hydroxypropyl)-5-methyl-2,3,5,6-tetrahydrobenzo[b][1,5]diazocin-4(1H)-one,
ethyl 2-(1-(3-(furan-2-ylmethoxy)-2-hydroxypropyl)-4-oxo-1,2,3,4-tetrahydrobenzo[b][1,5]diazocin-5(6H)-yl)acetate,
5-benzyl-1-(3-(furan-2-ylmethoxy)-2-hydroxypropyl)-2,3,5,6-tetrahydrobenzo[b][1,5]diazocin-4(1H)-one,
5-cyclopentyl-8-fluoro-1-(2-hydroxy-3,3-dimethylbutyl)-2,3,5,6-tetrahydrobenzo[b][1,5]diazocin-4(1H)-one,
ethyl 2-(4-oxo-1,2,3,4-tetrahydrobenzo[b][1,5]diazocin-5(6H)-yl)acetate,
1-(isoxazole-5-carbonyl)-8-methoxy-5-(3-methylbut-2-enyl)-2,3,5,6-tetrahydrobenzo[b][1,5]diazocin-4(1H)-one,
5-benzyl-1-(isoxazole-5-carbonyl)-2,3,5,6-tetrahydrobenzo[b][1,5]diazocin-4(1H)-one,
1-(isoxazole-5-carbonyl)-5-(pent-2-ynyl)-2,3,5,6-tetrahydrobenzo[b][1,5]diazocin-4(1H)-one,
9-(cyclopropylmethyl)-5-(isoxazol-5-ylcarbonyl)-6,7,9,10-tetrahydro[1,3]dioxolo[4,5-i][1,5]benzodiazocin-8(5H)-one,
1-(cyclobutanecarbonyl)-5-cyclopropyl-8-methoxy-2,3,5,6-tetrahydrobenzo[b][1,5]diazocin-4(1H)-one,
9-cyclopentyl-6,7,9,10-tetrahydro[1,3]dioxolo[4,5-i][1,5]benzodiazocin-8(5H)-one,
5-(3-tert-butoxy-2-hydroxypropyl)-9-cyclopropyl-6,7,9,10-tetrahydro[1,3]dioxolo[4,5-i][1,5]benzodiazocin-8(5H)-one,
5-ethyl-1-(2-hydroxypropyl)-2,3,5,6-tetrahydrobenzo[b][1,5]diazocin-4(1H)-one,
5-[3-(allyloxy)-2-hydroxypropyl]-9-ethyl-6,7,9,10-tetrahydro[1,3]dioxolo[4,5-i][1,5]benzodiazocin-8(5H)-one,
9-ethyl-5-(2-hydroxy-3-phenylpropyl)-6,7,9,10-tetrahydro[1,3]dioxolo[4,5-i][1,5]benzodiazocin-8(5H)-one,
5-ethyl-8-fluoro-1-(2-hydroxy-3,3-dimethylbutyl)-2,3,5,6-tetrahydrobenzo[b][1,5]diazocin-4(1H)-one,
7-(allyloxy)-5-ethyl-1-(2-hydroxy-3-phenoxypropyl)-8-methoxy-2,3,5,6-tetrahydrobenzo[b][1,5]diazocin-4(1H)-one,
5-cyclopentyl-8-fluoro-1-(2-hydroxy-3,3-dimethylbutyl)-2,3,5,6-tetrahydrobenzo[b][1,5]diazocin-4(1H)-one,
ethyl 2-(4-oxo-1,2,3,4-tetrahydrobenzo[b][1,5]diazocin-5(6H)-yl)acetate,
1-(isoxazole-5-carbonyl)-8-methoxy-5-(3-methylbut-2-enyl)-2,3,5,6-tetrahydrobenzo[b][1,5]diazocin-4(1H)-one,
5-benzyl-1-(isoxazole-5-carbonyl)-2,3,5,6-tetrahydrobenzo[b][1,5]diazocin-4(1H)-one,
1-(isoxazole-5-carbonyl)-5-(pent-2-ynyl)-2,3,5,6-tetrahydrobenzo[b][1,5]diazocin-4(1H)-one,
9-(cyclopropylmethyl)-5-(isoxazol-5-ylcarbonyl)-6,7,9,10-tetrahydro[1,3]dioxolo[4,5-i][1,5]benzodiazocin-8(5H)-one,
1-(cyclobutanecarbonyl)-5-cyclopropyl-8-methoxy-2,3,5,6-tetrahydrobenzo[b][1,5]diazocin-4(1H)-one,
9-cyclopentyl-6,7,9,10-tetrahydro[1,3]dioxolo[4,5-i][1,5]benzodiazocin-8(5H)-one,
5-(3-tert-butoxy-2-hydroxypropyl)-9-cyclopropyl-6,7,9,10-tetrahydro[1,3]dioxolo[4,5-i][1,5]benzodiazocin-8(5H)-one,
5-ethyl-1-(2-hydroxypropyl)-2,3,5,6-tetrahydrobenzo[b][1,5]diazocin-4(1H)-one,
5-[3-(allyloxy)-2-hydroxypropyl]-9-ethyl-6,7,9,10-tetrahydro[1,3]dioxolo[4,5-i][1,5]benzodiazocin-8(5H)-one,
9-ethyl-5-(2-hydroxy-3-phenylpropyl)-6,7,9,10-tetrahydro[1,3]dioxolo[4,5-i][1,5]benzodiazocin-8(5H)-one,
5-ethyl-8-fluoro-1-(2-hydroxy-3,3-dimethylbutyl)-2,3,5,6-tetrahydrobenzo[b][1,5]diazocin-4(1H)-one,
7-(allyloxy)-5-ethyl-1-(2-hydroxy-3-phenoxypropyl)-8-methoxy-2,3,5,6-tetrahydrobenzo[b][1,5]diazocin-4(1H)-one,
(R)-1-(3-(benzyloxy)-2-hydroxypropyl)-5-cyclopentyl-8-fluoro-2,3,5,6-tetrahydrobenzo[b][1,5]diazocin-4(1H)-one, and
7-(allyloxy)-5-(cyclopropylmethyl)-1-(isoxazole-5-carbonyl)-8-methoxy-2,3,5,6-tetrahydrobenzo[b][1,5]diazocin-4(1H)-one.

In particular, in formula I, when $Z^3$, $Z^4$, $Z^7$, $Z^8$, $Z^9$ and $Z^{10}$ represent H, $Z^5$ and $Z^6$ together represents =O, $R^1$ represents H, $R^2$ represents —COCF$_3$, X represents —CH=CH—, $Z^2$ represents H, then $Z^1$ does not represent

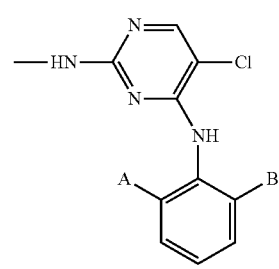

formula A wherein A is chosen from —CONHMe, —SO$_2$NHMe and B is H.

In particular, in formula I, when $Z^3$, $Z^4$, $Z^7$, $Z^8$, $Z^9$ and $Z^{10}$ represent H, $Z^5$ and $Z^6$ together represents =O, $R^1$ represents H, $R^2$ represents H, X represents —CH=CH—, $Z^2$ represents H, then $Z^1$ does not represent formula A wherein A is chosen from —CONHMe and —SO$_2$NHMe, and B is H.

In particular, in formula I, when $Z^3$, $Z^4$, $Z^7$, $Z^8$, $Z^9$ and $Z^{10}$ represent H, $Z^5$ and $Z^6$ together represents =O, $R^1$ represents H, $R^2$ represents —COCH$_3$ or —COCF$_3$, X represents —CH=CH—, $Z^2$ represents H, then $Z^1$ does not represent H, —NO$_2$ or —NH$_2$.

In particular, in formula I, when $Z^3$, $Z^4$, $Z^7$, $Z^8$, $Z^9$ and $Z^{10}$ represent H, $Z^5$ and $Z^6$ together represents =O, $R^1$ represents H, $R^2$ represents —COCH$_3$, X represents —CH=CH—, $Z^2$ represents H, then $Z^1$ does not represent formula A wherein A is chosen from —OCH$_2$CN, —OCH$_2$CH$_2$CN, —CH$_2$CH$_2$CN, —CONHMe, —SO$_2$NHMe and B is H.

In particular, in formula I, when $Z^3$, $Z^4$, $Z^7$, $Z^8$, $Z^9$ and $Z^{10}$ represent H, $Z^5$ and $Z^6$ together represents =O, $R^1$ represents H, $R^2$ represents —COCH$_3$, X represents —CH=CH—, $Z^2$ represents H, then $Z^1$ does not represent formula A wherein A is chosen from —CONHMe and —CONHEt, and B is F.

In particular, in formula I, when $Z^3$, $Z^4$, $Z^7$, $Z^8$, $Z^9$ and $Z^{10}$ represent H, $Z^5$ and $Z^6$ together represents =O, $R^1$ represents H, $R^2$ represents CH$_3$CO—, X represents —CH=CH—, $Z^2$ represents H, then $Z^1$ does not represent formula A wherein A is —OCH$_2$CN and B is Me.

In particular, in formula I, when $R^1$, $R^2$, $Z^2$, $Z^3$, $Z^4$, $Z^7$, $Z^8$, $Z^9$ and $Z^{10}$ represent H, $Z^5$ and $Z^6$ together represents =O, X represents —CH=CH—, then $Z^1$ does not represent H.

More particularly in formula I, when X is CH=CH and $Z^5$ and $Z^6$ together represents =O, then $Z^1$ does not represent —NH-heteroaryl-NH-heteroaryl, optionally one or two of the heteroaryl being substituted.

In particular, in formula I, when $R^2$, $Z^2$, $Z^3$, $Z^4$, $Z^7$, $Z^8$, $Z^9$ and $Z^{10}$ represent H, $Z^5$ and $Z^6$ together represent =O, $R^1$ represents H or Me, X represents —CH=N—, in particular N is at the position the closest to the [1,5]-diazocin cycle, then $Z^1$ does not represent —CH=CHCON(Me)-D wherein D is

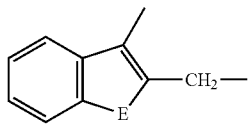

wherein E represents —O— or —S—. More particularly the conjugated double bond is E.

In particular, in formula I, when $R^2$, $Z^2$, $Z^3$, $Z^4$, $Z^7$, $Z^8$, $Z^9$ and $Z^{10}$ represent H, $Z^5$ and $Z^6$ together represents =O, $R^1$ represents H or Me, X represents —CH=N—, in particular N is at the closest position to the [1,5]-diazocin cycle, then $Z^1$ does not represent —CH=CHCON(Me)-CH$_2$-heterocycle, in particular heteroaryl, more particularly a bicyclyl heteroaryl, and even more particularly a 6+5 heteroaryl bicycle. More particularly the conjugated double bond is E.

In particular, in formula I, when $R^2$, $Z^2$, $Z^3$, $Z^4$, $Z^7$, $Z^8$, $Z^9$ and $Z^{10}$ represent H, $Z^5$ and $Z^6$ together represents =O, $R^1$ represents Me, X represents —CH=N—, In particular N is at the closest position to the [1,5]-diazocin cycle, then $Z^1$ does not represent —CH=CHCON(Me)-CH$_2$-aryl, in particular substituted aryl, more particularly substituted be nPrO— and MeO—, even more particularly as nPrO— in the meta position and MeO— in the neighbouring para position. More particularly the conjugated double bond is E.

In particular, in formula I, when $R^2$, $Z^2$, $Z^3$, $Z^4$, $Z^7$, $Z^8$, $Z^9$ and $Z^{10}$ represent H, $Z^5$ and $Z^6$ together represents =O, $R^1$ represents H or Me, X represents —CH=N—, in particular N is at the closest position to the [1,5]-diazocin cycle, then $Z^1$ does not represent H or Br.

In particular, in formula I, when $R^2$, $Z^2$, $Z^3$, $Z^4$, $Z^7$, $Z^8$, $Z^9$ and $Z^{10}$ represent H, $Z^5$ and $Z^6$ together represents =O, $R^1$ represents H or Me, X represents —CH=N—, in particular N is at the closest position to the [1,5]-diazocin cycle, then $Z^1$ does not represent —CH=CHCOOtBu or —CH=CHCOOH. More particularly the conjugated double bond is E.

In particular, in formula I, when $R^1$, $R^2$, $Z^2$, $Z^3$, $Z^4$, $Z^7$ $Z^8$ and $Z^{10}$ represent H, $Z^9$ represents phenyl, $Z^5$ and $Z^6$ together represents =O, X represents —CH=CH—, then $Z^1$ does not represent H.

In particular, in formula I, when $R^2$, $Z^2$, $Z^3$, $Z^4$, $Z^7$, $Z^8$, $Z^9$ and $Z^{10}$ represent H, $Z^5$ and $Z^6$ together represents =O, $R^1$ represents an alkyl bearing an alcohol function, such as —(CH$_2$)$_5$—OH, an alkyl, such as -tBu, or an alkylaryl, optionally bearing an alcohol, such as —CHMe-CHOHPh, more particularly such as —(R)CHMe-(S)CHOHPh, X represents —CH=CH—, then $Z^1$ does not represent H.

In particular, in formula I, when $R^2$, $Z^2$, $Z^3$, $Z^4$, $Z^7$, $Z^8$, $Z^9$ and $Z^{10}$ represent H, $Z^5$ and $Z^6$ together represents =O, $R^1$ represents benzyl, X represents —C(OMe)=CH—, then $Z^1$ does not represent methoxy, in particular the methoxy are neighbouring each other.

In particular, in formula I, when $Z^5$ and $Z^6$ together represents =O and X represents —CH=CH—, then at least one of the other groups is not H.

In particular, in formula I, when $Z^5$ and $Z^6$ together represents =O and X represents —CH=CH—, then $R^2$ is not CH$_3$CO— or CF$_3$CO—.

In particular, in formula I, when $Z^5$ and $Z^6$ together represents =O and X represents —CH=CH—, then $Z^1$ does not represent —NHalkyl, —NHcarbocycle or Nhheterocycle, such as 2-aminopyrimidine, optionally substituted, more particularly $Z^1$ does not represent 2,4-diamino-aminopyridine, optionally substituted, and even more particularly $Z^1$ does not represent 2,4-diamino-5-chloroaminopyridine, optionally substituted.

In particular, in formula I, when $Z^5$ and $Z^6$ together represents =O and X represents CH=N, then $Z^1$ is not —CH=CHCOalkyl, —CH=CHCONHCH$_2$-alkyl or —CH=CHCONHCH$_2$-heterocycle, optionally substituted.

In particular, in formula I, when $R^2$, $Z^2$, $Z^3$, $Z^4$, $Z^5$, $Z^6$, $Z^7$, $Z^8$, $Z^9$ and $Z^{10}$ represent H, $R^1$ represents H or an ester, such as —COOalkyl, in particular —COOtBu, X represents —CH=N—, in particular N is at the position the closest to the [1,5]-diazocin cycle, then $Z^1$ does not represent —CH=CHCON(Me)-D wherein D is

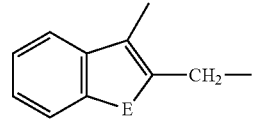

wherein E represents —O— or —S—. More particularly the conjugated double bond is E or trans.

In particular, in formula I, when $R^2$, $Z^2$, $Z^3$, $Z^4$, $Z^5$, $Z^6$, $Z^7$, $Z^8$, $Z^9$ and $Z^{10}$ represent H, $R^1$ represents H, COOH or COOAlkyl, in particular COOtBu, X represents —CH=N—, in particular N is at the closest position to the [1,5]-diazocin cycle, then $Z^1$ does not represent Br.

In particular, in formula I, when $R^2$, $Z^2$, $Z^3$, $Z^4$, $Z^5$, $Z^6$, $Z^7$, $Z^8$, $Z^9$ and $Z^{10}$ represent H, $R^1$ represents H, X represents —CH=N—, in particular N is at the closest position to the [1,5]-diazocin cycle, then $Z^1$ does not represent H.

In particular, in formula I, when $Z^2$, $Z^3$, $Z^4$, $Z^5$, $Z^6$, $Z^7$, $Z^8$, $Z^9$ and $Z^{10}$ represent H, $R^1$ represents Me, $R^2$ represents —$CH_2Ph$, X represents —CH=CH—, then $Z^1$ does not represent H, more particularly in the case of the methyl iodide salt.

In particular, in formula I, when $Z^2$, $Z^3$, $Z^4$, $Z^5$, $Z^6$, $Z^7$, $Z^8$, $Z^9$ and $Z^{10}$ represent H, $R^1$ represents Me, X represents —CH=CH—, $Z^1$ represents H, then $R^2$ does not represent —$COPhNH_2$, —CO-PhNHCOPhMe or —CO-PhNH-COPhCl in particular such as

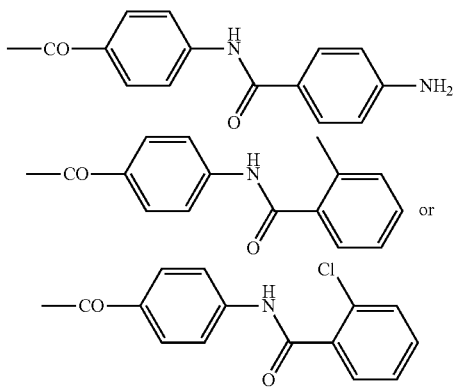

In particular, in formula I, when $Z^2$, $Z^3$, $Z^4$ $Z^5$, $Z^6$, $Z^7$, $Z^8$, $Z^9$ and $Z^{10}$ represent H, $R^1$ represent Me, $R^2$ represents H, X represents —$C(CF_3)$=N—, then $Z^1$ does not represent —$CF_3$.

In particular, in formula I, when $Z^2$, $Z^4$, $Z^5$, $Z^6$, $Z^7$, $Z^8$, $Z^9$ and $Z^{10}$ represent H, $Z^3$ represents an aryl, in particular Ph, $R^1$ represent H, $R^2$ represents H, an acyl, such as —$COCH_3$, or an alkyl, such as —$C_2H_5$, X represents —CH=CH—, then $Z^1$ does not represent H.

In particular, in formula I, when $Z^2$, $Z^3$, $Z^4$, $Z^5$, $Z^6$, $Z^7$, $Z^8$, $Z^9$ and $Z^{10}$ represent H, $R^1$ represents —$CH_2Ph$, $R^2$ represents H, an alkyl, in particular bearing an acid group, such as —$CH_2CH_2COOH$, or an —$SO_2aryl$, such as —$SO_2tolyl$, X represents —CH=CH—, then $Z^1$ does not represent H.

In particular, in formula I, when $Z^2$, $Z^3$, $Z^4$, $Z^5$, $Z^6$, $Z^7$, $Z^8$, $Z^9$ and $Z^{10}$ represent H, $R^1$ represents Ph, $R^2$ represents H or —$SO_2aryl$, such as —$SO_2tolyl$, X represents —CH=CH—, then $Z^1$ does not represent H.

In particular, in formula I, when $Z^2$, $Z^3$, $Z^4$, $Z^5$, $Z^6$, $Z^7$, $Z^8$, $Z^9$ and $Z^{10}$ represent H, $R^1$ represents Me, $R^2$ represents 3-chlorophenyl, X represents —CH=CH—, then $Z^1$ does not represent H.

In particular, in formula I, when $Z^2$, $Z^4$ $Z^5$, $Z^6$, $Z^7$, $Z^8$, $Z^9$ and $Z^{10}$ represent H, $Z^3$ represents Ph, $R^1$ represents H, $R^2$ represents H or methyl, X represents —CH=CH—, then $Z^1$ does not represent Cl.

In particular, in formula I, when $Z^2$, $Z^4$ $Z^5$, $Z^6$, $Z^7$, $Z^8$, $Z^9$ and $Z^{10}$ represent H, $Z^3$ represents Ph, $R^1$ represents H, $R^2$ represents H, X represents —CH=CH—, then $Z^1$ does not represent H or Cl.

In particular, in formula I, when $Z^2$, $Z^4$ $Z^5$, $Z^6$, $Z^7$, $Z^8$, $Z^9$ and $Z^{10}$ represent H, $Z^3$ represents Ph, $R^1$ represents H or Me, $R^2$ represents H, Me or —$SO_2alkylaryl$, such as —$SO_2tolyl$, X represents —CH=CH—, then $Z^1$ does not represent Cl.

In particular, in formula I, when $Z^2$, $Z^4$ $Z^5$, $Z^6$, $Z^7$, $Z^8$, $Z^9$ and $Z^{10}$ represent H, $Z^3$ represents Ph, $R^1$ represents H, $R^2$ represents Me, X represents —CH=CH—, then $Z^1$ does not represent H.

In particular, in formula I, when $Z^2$, $Z^3$, $Z^4$ $Z^5$, $Z^6$, $Z^7$, $Z^8$, $Z^9$ and $Z^{10}$ represent H, $R^1$ and $R^2$ represent H, X represents —CH=CH—, then $Z^1$ does not represent H.

In particular in formula I, when X represents —CH=CH— or —CH=N—, then $Z^3$ does not represent Ph.

In particular in the compound of Formula (I) when X represents —CH=CH—, $Z^1$, $Z^2$, $Z^3$, $Z^4$, $Z^5$, $Z^6$, $Z^7$, $Z^8$, $Z^9$, $Z^{10}$ represent each H, then $R^1$ and $R^2$ do not respectively represent H, H; Tosyl, Tosyl; benzyl, —$(CH_2)_2COOH$.

In particular in the compound of Formula (I) when X represents —CH=CCl—, $Z^1$, $Z^2$, $Z^5$, $Z^6$, $Z^7$, $Z^8$, $Z^9$, $Z^{10}$ represent each H, $Z^3$ and $Z^4$ represents H for one and Phenyl for the other, then $R^1$ and $R^2$ does not represent respectively Phenyl, H; Phenyl, Methyl; H, H; Methyl, H; H, Methyl; Methyl, Methyl; Tosyl, H; Tosyl, Methyl.

In particular in the compound of Formula (I) when X represents —CH=CH—, $Z^1$, $Z^2$, $Z^5$, $Z^6$, $Z^7$, $Z^8$, $Z^9$, $Z^{10}$ represent each H, and $Z^3$ and $Z^4$ represents H for one and Phenyl for the other, then $R^1$ and $R^2$ do not respectively represent H, H; H, Methyl.

In particular in the compound of Formula (I) when X represents —CH=CH—, $Z^1$, $Z^2$, $Z^5$, $Z^6$, $Z^7$, $Z^8$, $Z^9$, $Z^{10}$ represent each H, $Z^3$ and $Z^4$ represents H for one and metachlorophenyl for the other, then $R^1$ and $R^2$ do not respectively represent Tosyl, Acetate; Tosyl, Methyl.

In particular in the compound of Formula (I) when X represents —CH=CH—, $Z^1$, $Z^2$, $Z^3$, $Z^4$, $Z^7$, $Z^8$, $Z^9$, $Z^{10}$ represent each H, $Z^5$ and $Z^6$ represent together =O, then $R^1$ and $R^2$ do not respectively represent H, H; —$(CH_2)_5OH$, H; —CH(Me)CHOHPh, H; t-Bu, H.

In particular in the compound of Formula (I) when X represents —C(OMe)=CH—, $Z^1$ represents Methoxy, $Z^2$, $Z^3$, $Z^4$, $Z^7$, $Z^8$, $Z^9$, $Z^{10}$ represent each H, $Z^5$ and $Z^6$ represent together =O, and $Z^5$ and $Z^6$ are each H, then $R^1$ and $R^2$ do not respectively represent Benzyl, H.

In particular in the compound of Formula (I) when X represents —CH=CH—, $Z^1$ $Z^2$, $Z^3$, $Z^4$, $Z^7$, $Z^8$, $Z^9$, $Z^{10}$ represent each H, $Z^9$ and $Z^{10}$ represent H for one and phenyl for the other, $Z^5$ and $Z^6$ represent together =O, and $Z^5$ and $Z^6$ are each H, then $R^1$ and $R^2$ do not respectively represent H, H.

According to another aspect, an object of the invention is a composition comprising at least one compound as defined above.

In particular the invention concerns a medicament or a pharmaceutical composition comprising at least one compound of formula I or II as defined above, and optionally at least one pharmaceutically acceptable carrier or excipient.

The invention also concerns a compound of formula I or II as defined above for its use in therapy.

The invention also concerns the use of a compound of formula I as defined above for the preparation of a medicament.

The invention also concerns a compound of formula I or II as defined above for use for preventing and/or treating at least one disease, in particular as defined below. In particular, the medicament is intended to prevent and/or to treat at least one disease, condition and or disorder chosen from the group comprising or consisting of diabetes, hyperglycemia, low glucose tolerance, insulin resistance, obesity, lipid disorders, dyslipidemia, hyperlipidemia, hypertrigly-ceridemia, hypercholesterolemia, low HDL levels, high LDL levels, atherosclerosis and its sequelae, vascular restenosis, pancreatitis, abdominal obesity, neurodegenerative disease, retinopathy, nephropathy, neuropathy, Metabolic Syndrome, hypertension and other conditions and disorders where insulin resistance is a component, in a mammalian patient in need of such treatment.

The medicament is in particular intended to treat diabetes mellitus, especially of type 1 and/or of type 2.

According to another aspect, another object of the invention is a pharmaceutical composition comprising at least one compound of formula (I) and at least one pharmaceutically acceptable excipient.

In a particular embodiment, the present invention provides a pharmaceutical composition, further containing at least one additional compound, selected from the group consisting of physiologically acceptable excipients, auxiliaries, adjuvants, diluents, carriers and pharmaceutically active agents other than the compounds according to the invention.

In a particular embodiment, the present invention provides a set, or a kit, comprising separate packets comprising or consisting of:
a) a therapeutically effective amount of at least one compound according to the invention and,
b) a therapeutically effective amount at least one further pharmaceutically active agent other than the compound according to the invention.

Compounds of structural formula I may be used in combination with one or more other drugs in the treatment, prevention, suppression or amelioration of diseases, conditions or disorders for which compounds of structural formula I or the other drugs have utility.

Typically the combination of the drugs is safer or more effective than either drug alone, or the combination is safer or more effective than would it be expected based on the additive properties of the individual drugs. Such other drug(s) may be administered, by a route and in an amount commonly used contemporaneously or sequentially with a compound of structural formula I. When a compound of structural formula I is used contemporaneously with one or more other drugs, a combination product containing such other drug(s) and the compound of structural formula I is preferred. However, combination therapy also includes therapies in which the compound of structural formula I and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention include those that contain one or more other active ingredients, in addition to a compound of structural formula I.

Examples of other active ingredients that may be administered in combination with a compound of structural formula I, and either administered separately or in the same pharmaceutical composition, include, but are not limited to: dipeptidyl peptidase-IV (DP-IV) inhibitors; insulin sensitizing agents selected from the group consisting of PPAR-γ agonists, PPAR-α agonists, PPAR-α/γ dual agonists, PPAR pan-agonists and biguanides; PPAR-δ agonists; insulin and insulin mimetics; sulfonylureas and other insulin secretagogues; meglitinides; α-glucosidase inhibitors that inhibit carbohydrate digestion; GLP-1 (glucagon-like peptide 1), GLP-1 analogs and mimetics; amylin mimetics; GLP-1 receptor agonists and long-acting GLP-1 receptor agonists; GIP, GIP mimetics, and GIP receptor agonists; PACAP, PACAP mimetics, and PACAP receptor 3 agonists; cholesterol lowering agents; antiobesity compounds; ileal bile acid transporter inhibitors; anti-inflammatory agents, excluding glucocorticoids; glucocorticoids receptor ligands; protein tyrosine phosphatase 1B (PTP-1B) inhibitors or agents providing antisense modulation of PTP-1B expression; and antihypertensives including those acting on the angiotensin or renin systems; SGLT-1 (sodium-dependent glucose transporter 1) inhibitors; SGLT-2 (sodium-dependent glucose transporter 2) inhibitors or compounds reducing SGLT-2 gene expression; 11-Beta-HSD1 (11-beta hydroxysteroid dehydrogenase 1) inhibitors; AMPK (AMP-activated protein kinase) activators; tyrosine kinase inhibitors; glucagon and glucagon receptor antagonists; GPR (G-protein coupled receptors) modulators; FGF21 polypeptides or compounds; glucokinase activators; interteukin-1 receptor antagonists; FBPase (fructose 1,6-bisphosphatase) inhibitors; probucol and derivatives; unacylated ghrelin or any analog; antagonists of hepatic sympathetic activity; (S)-bethanechol; glutathione increasing compound; antioxidant; an [alpha]-adrenergic receptor antagonist; a [beta]-adrenergic receptor antagonist; a nonselective adrenergic receptor antagonist; a phosphodiesterase inhibitor; a cholineresterase antagonist; steviol, stevioside, and their derivatives; thyroid hormone mimetics; lipid lowering agents; compounds that activate insulin signalling pathway; vanadium compounds; Dopamine D2 receptor agonists; Colestimide (Mitsubishi-Tanabe); Bezafibrate+diflunisal/ CRx-401 (CombinatoRx); cortisol synthesis inhibitors; DM-71/bethanechol and N-acetyl cysteine (Diamedica); DM-83/combination of two generic compounds (Diamedica); compounds modulating islet regeneration factors; serum amyloid A protein inhibitors; compounds for mesenchymal stem cell therapy; insulin sensitizers via NF-kappaB pathway/TLR4 receptor; compounds modulating islet neogenesis associated proteins; MK 0893 (Merck); MK 0941 (Merck); anti-CD3 monoclonal antibodies; rhGAD65/recombinant human glutamic acid decarboxylase (Diamyd Therapeutics); Succinobucol/AGI 1067 (AtheroGenics) as an antioxidant/vascular cell adhesion molecule-1 modulating compound; compounds attenuating intestinal glucose absorption; gastrin analogs; glycogen phosphorylase inhibitors; GLUT2 transport (gut) inhibitors; UCP-2 (uncoupling protein 2) inhibitors or agents providing antisense modulation of UCP-2 expression; glucosylceramide synthase inhibitors.

In particular at least one compound of structural formula I may be combined with at least one, in particular at least two, other active compound, for example such as those disclosed above or below.

PPAR-γ agonists (thiazolidinediones) that can be combined with compounds of formula I include rosiglitazone (also named Avandia), pioglitazone (also named Actos), troglitazone (also named Rezulin), balaglitazone/DRF-2593 (Dr. Reddy's Laboratories/Rheoscience), mitoglitazone/ MDSC 0160 (Metabolic Solutions Development), netoglitazone/MCC-555 (Mitsubishi Tanabe/Perlegen), rivoglitazone/ CS-011 (Daiichi-Sankyo), englitazone.

Other PPAR agonists that can be combined with compounds of formula I include PPAR-α/γ agonists aleglitazar/ R1439 (Roche), muraglitazar (Bristol-Myers Squibb), tesaglitazar (Astra-Zeneca); PPAR pan-agonists such as indeglitazar and PLX204/PPM-204 (Plexxikon/Wyeth)); INT131/AMG131 (Amgen/InteKrin Therapeutics), MBX 2044 (Metabolex/Ortho-McNeil), Metaglidasen/MBX102/ JNJ-39659100 (Metabolex/Ortho-McNeil), ONO-5129 (Ono), KRP-297; PPARα agonists such as gemfibrozil, clofibrate, fenofibrate and bezafibrate; PPARδ such as those disclosed in WO97/28149.

Dipeptidyl peptidase-IV (DP-IV) inhibitors that can be combined with compounds of structural formula I include those disclosed in WO 03/004498, WO 03/004496; EP 1 258 476; WO 02/083128; WO 02/062764; WO 03/00025; WO 03/002530; WO 03/002531; WO 03/002553; WO 03/002593; WO 03/000180; and WO 03/000181. Specific DP-IV inhibitor compounds include isoleucine thiazolidid, NVP-DPP728, P32/98, LAF 237, PSN9301 (OSI Pharmaceuticals), Glactiv (Ono Pharmaceuticals), PHX1149 (Forest Labs/Phenomix), Alogliptin/SYR-322 (Takeda), AMG 222/ALS2-0426 (Amgen/Servier), Dutogliptin/PHX1149 (Phenomix/Forest Laboratories), KRP-204/N-5984 (Kyorin), KRP-104 (Kyorin/ActivX Biosciences), Linagliptin/BI-1356 (Boehringer Ingelheim), Melogliptin/GRC 8200 (Glenmark Pharmaceuticals), MP-513 (Mitsubishi Tanabe Pharma), PF 734200 (Pfizer), R1579 (Roche/Chugai), Saxagliptin/BMS-477118 (Bristol-Myers Squibb/AstraZeneca), SYR 472 (Takeda), TA-6666 (Mitsubishi Tanabe), Vildagliptin (Novartis).

Specific GLP-1 analogs/mimetics, GLP-1 receptor agonists and long-acting GLP-1 receptor agonists compounds include those described in WO 00/42026 and WO 00/59887, albiglutide/GSK716155 (GSK), AVE0010/ZP-10/lixisenatide (Zealand Pharma/Sanofi-Aventis), CJC-1134-PC/PC-DAC also named Exendin-4 (ConjuChem), Exenatide LAR (Amylin/Alkermes/Lilly), Liraglutide/N N2211 (Novo Nordisk), once-daily liraglutide (Novo Nordisk), LY 2189265 (Lilly), semaglutide/NN9535 (Novo Nordisk), Taspoglutide/R1583/BIM-51077 (Roche/Ipsen), oral GLP-1 analogues such as those developed by Diabetology.

GIP mimetics that can be combined with compounds of formula I include those disclosed in WO 00/58360.

For a review of incretin compounds (i.e. compounds modulating DP-IV and/or GLP-1 pathways) that can be combined with compounds of structural formula I, see "The incretins: From the concept to their use in the treatment of type 2 diabetes. Part A: Incretins: Concept and physiological functions—Diabetes & Metabolism 34 (2008) 550-559" and "Mining incretin hormone pathways for novel therapies—Trends Endocrinol Metab. 2009 August; 20(6):280-6".

Specific amylin mimetics compounds include pramlintide acetate (Symlin) and those described in WO 2003/057244 (Amylin Pharmaceuticals).

PACAP, PACAP mimetics, and PACAP receptor 3 agonists that can be combined with compounds of formula I include those disclosed in WO 01/23420.

Biguanides that can be combined with compounds of formula I include metformin (also named Glucophage), phenformin, Metformin gum/buccal (Generex/Fertin)

Insulin and insulin analogs/mimetics that can be combined with compounds of formula I include regular insulin, lente insulin, semilente insulin, ultralente insulin, insulin glargine, insulin aspart, NPH, Humalog, Novolog, Inhaled Technosphere insulin (Mannkind), Insulin intranasal (Bentley), Insulin intranasal (MDRNA), Oral HDV insulin (Diasome), Oral insulin spray (Generex), NN1250 insulin analog for injection (Novo Nordisk), NN5401 insulin analog for injection (Novo Nordisk), Actrapid (Novo Nordisk), Novomix (Novo Nordisk), Novorapid (Novo Nordisk), Levemir (Novo Nordisk), rapid-acting insulin for injection (Biodel), recombinant human hyaluroindase (rHuPH20)/insulin co-formulation for injection (Halozyme Therapeutics), Capsulin OAD (Diabetology), Capsulin IR (Diabetology), Combulin (insulin+insulin sensitizer, Diabetology).

Sulfonylureas that can be combined with compounds of formula I include tolbutamide (Orinase), acetohexamide (Dymelor), tolazamide (Tolinase), chlorpropamide (Diabinese), glipizide (Glucotrol), glyburide (Diabeta, Micronase, Glynase), glimepiride (Amaryl), or gliclazide (Diamicron).

Meglitinides that can be combined with compounds of formula I include the benzoic acid derivative repaglinide (Prandin, Novonorm), nateglinide (Starlix), Mitiglinide (Elixir Pharmaceuticals).

α-glucosidase inhibitors inhibiting carbohydrate digestion, which can be combined with compounds of formula I include miglitol (Glyset), acarbose (Precose/Glucobay), voglibose.

Cholesterol lowering agents that can be combined with compounds of formula I include HMG-CoA reductase inhibitors, sequestrants, nicotinyl alcohol, nicotinic acid and salts thereof, inhibitors of cholesterol absorption, acyl CoA:cholesterol acyltransferase inhibitors, and anti-oxidants.

Antiobesity compounds that can be combined with compounds of structural formula I include fenfluramine, dexfenfluramine, phentermine, sibutramine, orlistat, diethylpropion (Tenuate®), phendimetrazine (Prelu-2®, Bontril®), benzphetamine (Didrex®), sibutramine (Meridia®, Reductil®); rimonabant (Acomplia®), oxyntomodulin; fluoxetine hydrochloride (Prozac), Qnexa (topiramate and phentermine), Excalia (bupropion and zonisamide), Contrave (bupropion and naltrexone), Lorcaserin (developed by Arena), lipase inhibitors similar to xenical (Orlistat) or Cetilistat (also known as ATL-962), neuropeptide Y1 or Y5 antagonists, cannabinoid CB 1 receptor antagonists or inverse agonists, melanocortin receptor agonists, in particular, melanocortin-4 receptor agonists, ghrelin antagonists, and melanin-concentrating hormone (MCH) receptor antagonists. For a review of anti-obesity compounds that can be combined with compounds of structural formula I, see S. Chaki et al., "Recent advances in feeding suppressing agents: potential therapeutic strategy for the treatment of obesity," Expert Opin. Ther. Patents, 11: 1677-1692 (2001) and D. Spanswick and K. Lee, "Emerging antiobesity drugs," Expert Opin. Emerging Drugs, 8: 217-237 (2003).

Neuropeptide Y5 antagonists that can be combined with compounds of structural formula I include those disclosed in U.S. Pat. No. 6,335,345 and WO 01/14376; and specific compounds identified as GW59884A; GW569180A; LY366377; and COP-71683A.

Cannabinoid CB 1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. Nos. 5,532,237; and 5,292,736.

Melanocortin receptor agonists that can be combined with compounds of formula I include those disclosed in WO 03/009847; WO 02/068388; WO 99/64002; WO 00/74679; WO 01/70708; and WO 01/70337 as well as those disclosed in J. D. Speake et al., "Recent advances in the development of melanocortin-4 receptor agonists, Expert Opin. Ther. Patents, 12: 1631-1638 (2002).

Glucocorticoids receptor ligands that can be combined with compounds of formula I include those described in WO 2004/000869 (Abbott Laboratories) or liver-selective glucocorticoid receptor antagonists like compound A-348441 (Abbott Laboratories, Karo Bio).

Protein tyrosine phosphatase 1B (PTP-1B) inhibitors or agents providing antisense modulation of PTP-1B expression that can be combined with compounds of formula I include ISIS113715 (Isis Pharmaceuticals), JTT-551 (Japan Tobacco) and those described in WO 2006/044531, WO 03/099227 and WO 03/070881. For a review of protein tyrosine phosphatase inhibitors that can be combined with compounds of structural formula I, see "Use of Protein Tyrosine Phosphatase Inhibitors as Promising Targeted Therapeutic Drugs. Current Medicinal Chemistry, Volume 16, Number 6, February 2009, pp. 706-733(28)".

Antihypertensives that can be combined with compounds of formula I include those acting on the angiotensin or renin systems, such as angiotensin converting enzyme inhibitors, angiotensin II receptor antagonists or renin inhibitors, such as captopril, cilazapril, enalapril, fosinopril, lisinopril, quinapril, ramapril, zofenopril, candesartan, cilexetil, eprosartan, irbesartan, losartan, tasosartan, telmisartan, and valsartan.

SGLT-1 or SGLT-2 (sodium-dependent glucose transporter 1 or 2) inhibitors or compounds reducing SGLT-1 gene and/or SGLT-2 gene expression, that can be combined with compounds of formula I include AVE2268 (Sanofi-Aventis), compound 189075/sergliflozin (GSK), those described in WO 2003/099836 (BMS), ASP1941 and YM543 (Astellas), BI10773 (Boehringer Ingelheim), dapagliflozin/BMS512148 (AstraZeneca/Bristol-Myers Squibb), KGT-1681 (GSK/Kissei), remogliflozin etabonate/189075 (GSK/Kissei), TA-7284 (Mitsubishi Tanabe/Ortho McNeil), canagliflozin (Mitsubishi Tanabe Pharma/Johnson & Johnson), phlorizin and its synthetic derivative T-1095, antisense oligonucleotide ISIS 388626 (Isis Pharmaceuticals), 12-nucleotide antisense oligonucleotide ISIS-SGLT2RX (Isis Pharmaceuticals).

11-Beta-HSD1 (11-beta hydroxysteroid dehydrogenase 1) inhibitors that can be combined with compounds of formula I include compound INCB013739 (Incyte Corporation) and those described in WO 2006/002350 (Incyte Corporation), WO 2009/023180 (Schering Corporation), WO 2007/118185 (Abbott Laboratories), the compounds developed by Vitae Pharmaceuticals and Boeringher-Ingelheim.

AMPK (AMP-activated protein kinase) activators that can be combined with compounds of formula I include those described in WO/2004/043957 (Les Laboratoires Servier), WO 2009/019600 (DR. REDDY'S LABORATORIES LTD), Debio 0930 (Debiopharm).

Tyrosine kinase inhibitors that can be combined with compounds of formula I include those described in WO 2006/124544 (Novartis).

Glucagon receptor antagonists that can be combined with compounds of formula I include those described in WO 2009/058662, WO 98/04528, WO 99/01423, WO 00/39088, WO 00/69810, and compounds showing both glucagon receptor antagonism and GLP-1 agonism activity such as ZP2929 and those described in WO 2009/058734.

GPR (G-protein coupled receptor) modulators that can be combined with compounds of formula I include GPR19 modulators such as those described in WO 2006/076231 (Arena Pharmaceuticals, combination of a GPR19 agonist and a DP-IV inhibitor), GPR40 modulators such as those described in WO 2004/072650 (Bayer Healthcare Ag), GPR41 modulators such as those described in WO 2006/052566 (Arena Pharmaceuticals) and WO 2004/038421 (Bayer Healthcare Ag), GPR43 modulators such as those described in U.S. Pat. No. 7,303,889, WO 2003/057730 (Euroscreen SA) and WO 2004/038405 (Bayer Healthcare Ag), INCB19602 (Incyte) as a GPR109A receptor agonist/HM74a agonist, GPR119 agonist such as AR231453 (Arena Pharmaceuticals), GPR120 modulators such as those described in WO 2007/134613 (Rheoscience NS), G protein-coupled bile acid receptor 1 (GPBAR1; also known as TGR5) agonists. For a review of GPR modulators compounds that can be combined with compounds of structural formula I, see "Islet G protein-coupled receptors as potential targets for treatment of type 2 diabetes.—Nat Rev Drug Discov. 2009 May; 8(5): 369-85".

FGF21 polypeptides or compounds that can be combined with compounds of formula I include those described in WO 2005/091944 and WO 2005/072769 (Eli Lilly & Co), WO 2008/121563 (Ambrx Inc.).

Glucokinase activators that can be combined with compounds of formula I include AZD6370 (AstraZeneca) and those described in WO 0058293 (in particular compound R00281675 (Hoffman-La Roche)), WO 2007115968 (in particular compound R04389620 (trade name, Piragliatin) (Hoffman-La Roche)), WO 20040631 (in particular compound LY2121260 (Eli Lilly)), WO 2004072031 (in particular compound PSN-GK1(OSI)), WO 2005044801 (in particular compound GKA-50 (Astra-Zeneca)), WO 2007122482 (Pfizer), WO 2003080585 (Merck-Banyu), WO 200710434 (Takeda), WO 2007075847 (Takeda), WO 2005/123132 (Novo-Nordisk). For a review of glucokinase activators that can be combined with compounds of structural formula I, see "Recent advances in glucokinase activators for the treatment of type 2 diabetes—Drug Discov Today. 2009 August; 14(15-16):784-92".

Interteukin-1 receptor antagonists that can be combined with compounds of formula I include those described in EP 0661992 (Amgen Inc), the interleukin-1 inhibitor AMG-108 (Amgen), the anti-interleukin-1 beta antibody Canakinumab/ACZ885 (Novartis).

FBPase (fructose 1,6-bisphosphatase) inhibitors that can be combined with compounds of formula I include MB06322 (Metabasis Therapeutics), MB 07803 (Metabasis/Daiichi Sankyo).

Probucol and derivatives that can be combined with compounds of formula I include those described in WO 2008/118948 (Atherogenics Inc), and AGi-1067 (succinobucol, Atherogenics Inc).

Unacylated ghrelin or any analog that can be combined with compounds of formula I include those described in WO 2008/145749 (Alize Pharma SAS).

Antagonists of hepatic sympathetic activity that can be combined with compounds of formula I include those described in WO 2005/025570 (Diamedica Inc).

(S)-bethanechol that can be combined with compounds of formula I include compounds described in WO 2007/082381 (Diamedica Inc).

Glutathione increasing compounds that can be combined with compounds of formula I include N-acetylcysteine, a cysteine ester, L-2-oxothiazolidine-4-carboxolate (OTC), gamma glutamylcysteine and its ethyl ester, glytathtione ethyl ester, glutathione isopropyl ester, [alpha]-lipoic acid, oxathiazolidine-4-carboxylic acid, cysteine, methionine, bucillamine and S-adenosylmethionine.

Antioxidant compounds that can be combined with compounds of formula I include compounds vitamin E, vitamin C, an isoflavone, zinc, selenium, ebselen, and a carotenoid.

[alpha]-adrenergic receptor antagonists that can be combined with compounds of formula I include compounds prazosin, doxazocin, phenoxybenzamine, terazosin, phentolamine, rauwolscine, yohimine, tolazoline, tamsulosin, and terazosin;

[beta]-adrenergic receptor antagonists selected that can be combined with compounds of formula I include acebutolol, atenolol, betaxolol, bisoprolol, carteolol, esmolol, metoprolol, nadolol, penbutolol, pindolol, propanolol, timolol, dobutamine hydrochloride, alprenolol, bunolol, bupranolol, carazolol, epanolol, moloprolol, oxprenolol, pamatolol, talinolol, tiprenolol, tolamolol, and toliprolol;

Nonselective adrenergic receptor antagonists that can be combined with compounds of formula I include compounds carvedilol and labetolol.

Phosphodiesterase inhibitors that can be combined with compounds of formula I include anagrelide, tadalfil, dipyridamole, dyphylline, vardenafil, cilostazol, milrinone, theophylline, and caffeine.

Cholineresterase antagonists that can be combined with compounds of formula I include donepezil, tacrine, edrophonium, demecarium, pyridostigmine, zanapezil, phospholine, metrifonate, neostigmine, phenserine and galathamine.

Steviol, isosteviol, glucosilsteviol, gymnemic acid, steviolbioside, stevioside, Rebaudioside A, Rebaudioside B, Rebaudioside C, Rebaudioside D, Rebaudioside E, Dulcoside A and their derivatives can be combined with compounds of formula I.

Thyroid hormone mimetics that can be combined with compounds of formula I are described in "Thyroid hormone mimetics: potential applications in atherosclerosis, obesity and type 2 diabetes.—Nat Rev Drug Discov. 2009 April; 8(4):308-20."

Lipid lowering agents that can be combined with compounds of formula I include bile salt sequestering resins (e.g., cholestyramine, colestipol, and colesevelam hydrochloride), HMGCo A-reductase inhibitors (e.g., lovastatin, pravastatin, atorvastatin, simvastatin, and fluvastatin), nicotinic acid, fibric acid derivatives (e.g., clofibrate, gemfibrozil, fenofibrate, bezafibrate, and ciprofibrate), probucol, neomycin, dextrothyroxine, plant-stanol esters, cholesterol absorption inhibitors (e.g., ezetimibe), CETP inhibitors (e.g. torcetrapib, and JTT-705) MTP inhibitors (e.g., implitapide), inhibitors of bile acid transporters (apical sodium-dependent bile acid transporters), regulators of hepatic CYP7a, ACAT inhibitors (e.g. Avasimibe), estrogen replacement therapeutics (e.g., tamoxigen), synthetic HDL (e.g. ETC-216), anti-inflammatories (e.g., glucocorticoids), colesevelam hydrochloride (Welchol).

Compounds activating the insulin signalling pathway, which can be combined with compounds of formula I, include AJD101 (Daiichi Sankyo).

Vanadium compounds that can be combined with compounds of formula I include AKP-020 (Akesis).

Dopamine D2 receptor agonists that can be combined with compounds of formula I include bromocryptine (also named Cycloset, from VeroScience).

Cortisol synthesis inhibitors that can be combined with compounds of formula I include D10-902/2S,4R ketoconazole (DiObex).

Compounds modulating islet regeneration factors, which can be combined with compounds of formula I, include E1 INT (Transition Therapeutics).

Serum amyloid A protein inhibitors that can be combined with compounds of formula I include Eprodisate/NC-503 (Bellus Health).

Mesenchymal stem cell therapy that can be combined with compounds of formula I include ex vivo cultured adult human mesenchymal stem cells (Osiris).

Insulin sensitizers via NF-kappaB pathway/TLR4 receptor, which can be combined with compounds of formula I, include HE3286 (Hollis-Eden).

Compounds modulating the islet neogenesis associated proteins, which can be combined with compounds of formula I, include INGAP peptide (Kinexum).

Anti-CD3 monoclonal antibodies that can be combined with compounds of formula I include Otelixizumab/TRX4 (GSK, Tolerx) and teplizumab/MGA031/hOKT3gamma1 (Ala-Ala) (by Lilly/MacroGenics).

Compounds attenuating intestinal glucose absorption, which can be combined with compounds of formula I, include Tagatose (Spherix).

Gastrin analogs that can be combined with compounds of formula I include TT-223 (Lilly/Transition Therapeutics).

Glycogen phosphorylase inhibitors which can be combined with compounds of formula I include those described in "New Inhibitors of Glycogen Phosphorylase as Potential Antidiabetic Agents. Current Medicinal Chemistry, Volume 15, Number 28, December 2008, pp. 2933-2983(51)".

GLUT2 transport inhibitors which can be combined with compounds of formula I include flavonoids such as quercetin.

Glucosylceramide synthase inhibitors which can be combined with compounds of formula I, include N-[5-(Adamantan-1-yl-methoxy)-pentyl]-1-deoxynojirimycin, N-(5'-adamantane-1'-yl-methoxy)-pentyl-1-deoxynojirimycin and their derivatives, N-butyl-deoxygalactonojirimycin (OGB-1) and its derivatives, N-nonyl-deoxygalactonojirimycin (OGB-2) and its derivatives.

In another aspect of the invention, a pharmaceutical composition is disclosed which comprises a compound according to structural formula I, a compound selected from the group of active agent, as listed above, and a pharmaceutically acceptable carrier.

In another aspect, the present invention provides methods for treatment, prevention, inhibition or amelioration of one or more symptoms of diseases or disorders selected from non-insulin dependent diabetes mellitus (type II diabetes), insulin dependent diabetes mellitus (type I diabetes), hypertension, pre-diabetes, the metabolic syndrome, obesity and related metabolic diseases.

In another aspect of the invention, the invention provides a method of reducing the risk of developing a condition selected from the group consisting of non-insulin dependent diabetes mellitus (type II diabetes), insulin dependent diabetes mellitus (type I diabetes), hypertension, pre-diabetes, the metabolic syndrome, obesity and related metabolic diseases.

In another aspect of the invention, the invention provides a method of treating a condition selected from the group consisting of hyperglycemia, low glucose tolerance, insulin resistance, obesity, lipid disorders, dyslipidemia, hyperlipidemia, hypertrigly-ceridemia, hypercholesterolemia, low HDL levels, high LDL levels, atherosclerosis and its sequelae, vascular restenosis, pancreatitis, abdominal obesity, neurodegenerative disease, retinopathy, nephropathy, neuropathy, pre-diabetes, metabolic syndrome, hypertension and metabolic disorders where insulin resistance and/or insulin secretion defects are a component, in a mammalian patient in need of such treatment.

Said method may comprise administering to the patient an effective amount of at least one compound of formula I and at least one compound such as those listed above as other active ingredients which can be combined with formula I compounds; said compounds being administered to the patient in an amount that is effective to prevent or treat said disease or condition.

A further embodiment of the present invention is a process for the manufacture of said pharmaceutical compositions, characterized in that at least one compound of formula I and at least one compound selected from the group consisting of solid, liquid or semiliquid excipients, auxiliaries, adjuvants, diluents, carriers and pharmaceutically active agents other than the compounds according to the invention, are converted in a suitable dosage form.

The pharmaceutical compositions, medicaments or treatments may be administered by any means that achieve their intended purpose. For example, administration may be by oral, parenteral, topical, enteral, intravenous, intramuscular, inhalant, nasal, intraarticular, intraspinal, transtracheal, transocular, subcutaneous, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired. Parenteral administration is preferred. Oral administration is especially preferred.

Suitable dosage forms include, but are not limited to capsules, tablets, pellets, dragees, semi-solids, powders, granules, suppositories, ointments, creams, lotions, inhalants, injections, cataplasms, gels, tapes, eye drops, solution, syrups, aerosols, suspension, emulsion, which can be produced according to methods known in the art, for example as described below:

Tablets: mixing of active ingredient/s and auxiliaries, compression of said mixture into tablets (direct compression), optionally granulation of part of mixture before compression.

Capsules: mixing of active ingredient/s and auxiliaries to obtain a flowable powder, optionally granulating powder, filling powders/granulate into opened capsules, capping of capsules.

Semi-solids (ointments, gels, creams): dissolving/dispersing active ingredient/s in an aqueous or fatty carrier; subsequent mixing of aqueous/fatty phase with complementary fatty/aqueous phase, homogenization (creams only).

Suppositories (rectal and vaginal): dissolving/dispersing active ingredient/s in carrier material liquified by heat (rectal: carrier material normally a wax; vaginal: carrier normally a heated solution of a gelling agent), casting said mixture into suppository forms, annealing and withdrawal suppositories from the forms.

Aerosols: dispersing/dissolving active agent/s in a propellant, bottling said mixture into an atomizer.

In general, non-chemical routes for the production of pharmaceutical compositions and/or pharmaceutical preparations comprise processing steps on suitable mechanical means known in the art that transfer one or more compounds according to the invention into a dosage form suitable for administration to a patient in need of such a treatment. Usually, the transfer of one or more compounds according to the invention into such a dosage form comprises the addition of one or more compounds, selected from the group consisting of carriers, excipients, auxiliaries and pharmaceutical active ingredients other than the compounds according to the invention. Suitable processing steps include, but are not limited to combining, milling, mixing, granulating, dissolving, dispersing, homogenizing, casting and/or compressing the respective active and non-active ingredients. Mechanical means for performing said processing steps are known in the art, for example from Ullmann's Encyclopedia of Industrial Chemistry, $5^{th}$ Edition. In this respect, active ingredients are preferably at least one compound according to this invention and one or more additional compounds other than the compounds according to the invention, which show valuable pharmaceutical properties, preferably those pharmaceutical active agents other than the compounds according to the invention, which are disclosed herein.

Particularly suitable for oral use are tablets, pills, coated tablets, capsules, powders, granules, syrups, juices or drops, suitable for rectal use are suppositories, suitable for parenteral use are solutions, preferably oil-based or aqueous solutions, furthermore suspensions, emulsions or implants, and suitable for topical use are ointments, creams or powders. The novel compounds may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins.

Suitable excipients are organic or inorganic substances, which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose, sucrose, mannitol, sorbitol or starch (maize starch, wheat starch, rice starch, potato starch), cellulose preparations and/or calcium phosphates, for example tricalcium phosphate or calcium hydrogen phosphate, magnesium stearate, talc, gelatine, tragacanth, methyl cellulose, hydroxypropyl-methylcellulose, sodium carboxymethylcellulose, polyvinyl pyrrolidone and/or Vaseline.

If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings, which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices or to provide a dosage form affording the advantage of prolonged action, the tablet, dragee or pill can comprise an inner dosage and an outer dosage component me latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol, solutions of suitable cellulose preparations such as acetyl-cellulose phthalate, cellulose acetate or hydroxypropymethyl-cellulose phthalate, are used. Dye stuffs or pigments may be added to the tablets or dragee coatings, for example, for identification or in order to characterize combinations of active compound doses.

Suitable carrier substances are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc and petroleum jelly. In particular, tablets, coated tablets, capsules, syrups, suspensions, drops or suppositories are used for enteral administration, solutions, preferably oily or aqueous solutions, furthermore suspensions, emulsions or implants, are used for parenteral administration, and ointments, creams or powders are used for topical application. The novel compounds can also be lyophilized and the lyophilizates obtained can be used, for example, for the production of injection preparations.

The preparations indicated can be sterilized and/or can contain excipients such as lubricants, preservatives, stabilizers and/or wetting agents, emulsifiers, salts for affecting the osmotic pressure, buffer substances, colorants, flavourings and/or aromatizers. They can, if desired, also contain one or more further active compounds, e.g. one or more vitamins.

Other pharmaceutical preparations, which can be used orally include push-fit capsules made of gelatine, as well as soft, sealed capsules made of gelatine and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

The liquid forms in which the novel compositions of the present invention may be incorporated for administration orally include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethyl-cellulose, methylcellulose, polyvinyl-pyrrolidone or gelatine.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400).

Aqueous injection suspensions may contain substances, which increase the viscosity of the suspension, including, for example, sodium carboxymethyl cellulose, sorbitol, and/or dextran, optionally the suspension contains stabilizers.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers.

Possible pharmaceutical preparations, which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatine rectal capsules, which consist of a combination of the active compounds with a base. Possible base materials include, for example, liquid triglycerides, polyethylene glycols, or paraffin hydrocarbons.

For use in medicine, the compounds of the present invention will be in the form of pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic bases, e.g. quaternary ammonium salts.

The present invention includes within its scope prodrugs of the compounds of the present invention above. In general, such prodrugs will be functional derivatives of the compounds of the present invention, which are readily convertible in vivo into the required compound of the present invention. Conventional procedures for the selection and preparation of suitable prodrug derivatives are described, for example, in Design of Prodrugs, ed. H. Bundgaard, Elsevier, 1985.

The pharmaceutical preparations can be employed as medicaments in human and veterinary medicine. As used herein, the term "effective amount" amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. Said therapeutic effective amount of one or more of the compounds according to the invention is known to the skilled artisan or can be easily determined by standard methods known in the art.

The substances according to the invention are generally administered analogously to commercial preparations. Usually, suitable doses that are therapeutically effective lie in the range between 0.0005 mg and 1000 mg, preferably between 0.005 mg and 500 mg and especially between 0.5 and 100 mg per dose unit. The daily dose is preferably between about 0.001 and 10 mg/kg of body weight.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The host, or patient, may be from any mammalian species, e.g., primate sp., particularly human; rodents, including mice, rats and hamsters; rabbits; equines, bovines, canines, felines, etc. Animal models are of interest for experimental investigations, providing a model for treatment of human disease.

The specific dose for the individual patient depends, however, on the multitude of factors, for example on the efficacy of the specific compounds employed, on the age, body weight, general state of health, the sex, the kind of diet, on the time and route of administration, on the excretion rate, the kind of administration and the dosage form to be administered, the pharmaceutical combination and severity of the particular disorder to which the therapy relates. The specific therapeutic effective dose for the individual patient can readily be determined by routine experimentation, for example by the doctor or physician, which advises or attends the therapeutic treatment.

In the case of many disorders, the susceptibility of a particular cell to treatment with the subject compounds may be determined by in vitro testing. Typically a culture of the cell may be combined with a subject compound at varying concentrations for a period of time sufficient to allow the active agents to show a relevant reaction, usually between about one hour and one week. For in vitro testing, cultured cells from a biopsy sample may be used.

Definitions

The following terms and expressions contained herein are defined as follows:

As used herein, the term "alkyl" refers to a aliphatic hydrocarbon group which may be straight, or branched having 1 to 8 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons. A designation such as "$C_1$-$C_4$ alkyl" refers to an alkyl radical containing from 1 to 4 carbon atoms.

As used herein, the term "alkenyl" refers to a straight chain, or branched hydrocarbon chains of 2 to 8 carbon atoms having at least one carbon-carbon double bond. A designation "$C_2$-$C_8$ alkenyl" refers to an alkenyl radical containing from 2 to 8 carbon atoms. Examples of alkenyl groups include ethenyl, propenyl, isopropenyl, 2,4-pentadienyl, etc.

As used herein, the term "alkynyl" means an aliphatic hydrocarbon group containing a carbon-carbon triple bond and which may be straight or branched having 2 to 8 carbon atoms in the chain. Branched means that at least one lower alkyl group such as methyl, ethyl or propyl are attached to a linear alkynyl chain. Exemplary alkynyl groups include ethynyl, propynyl, n-butynyl, 2-butynyl, 3-methylbutynyl, n-pentynyl, heptynyl, octynyl.

As used herein, the term "alkylene" means a straight or branched bivalent hydrocarbon chain having from 1 to 8 carbon atoms. The preferred alkylene groups are the lower alkylene groups having from 1 to about 4 carbon atoms. Exemplary groups include methylene (—$CH_2$—), and ethylene (—$CH_2CH_2$—).

As used herein, the term "alkoxy" means an alkyl-O— group wherein the alkyl group is as herein described. Exemplary alkoxy groups include methoxy, ethoxy, n-propoxy, i-propoxy, n-butoxy and heptoxy.

As used herein, the term "alkylenoxy" means an alkylene-O— group, wherein the alkylene group is as herein defined.

As used herein, the term "alkylenedioxy" means an —O-alkyl-O— group wherein the alkyl group is as herein described. Exemplary alkyl groups include methyl, ethyl, n-propyl, i-propyl, n-butyl and heptyl.

As used herein, the terms "halogen atom" or "halogen" refers to fluorine, chlorine, bromine or iodine atom, preferably bromine, fluorine and chlorine atom.

As used herein, the term "halogenoalkyl" refers to an alkyl group substituted by one or more halogen atoms, wherein said alkyl group and halogen atoms are as defined above. Halogenoalkyl groups include notably perhalogenoalkyl groups, such as perfluoroalkyl groups of formula $C_nF_{2n+1}$—. Examples of halogenalkyl groups include trifluoromethyl ($CF_3$).

As used herein, the term "halogenoalkoxy" refers to an alkyl group substituted by one or more halogen atoms, wherein said alkoxy group and halogen atoms are as defined above.

As used herein, the terms "carbocycle", "carbocyclic" or "carbocyclyl" refer to a substituted or unsubstituted, stable monocyclic or bicyclic hydrocarbon ring system which is saturated, partially saturated or unsaturated, and contains from 3 to 10 ring carbon atoms. Accordingly the carbocyclic group may be aromatic or non-aromatic, and includes the cycloalkyl and aryl compounds defined herein. The bonds connecting the endocyclic carbon atoms of a carbocyclic group may be single, double, triple, or part of a fused aromatic moiety.

As used herein, the term "cycloalkyl" refers to a saturated or partially saturated mono- or bicyclic alkyl ring system containing 3 to 10 carbon atoms. A designation such as "$C_5$-$C_7$ cycloalkyl" refers to a cycloalkyl radical containing from 5 to 7 ring carbon atoms. Preferred cycloalkyl groups include those containing 5 or 6 ring carbon atoms. Examples of cycloalkyl groups include such groups as cyclopropyl, cyclobutyl, cyclopentyl, cyclohexyl, cycloheptyl, cyclooctyl, pinenyl, and adamantanyl.

As used herein, the term "cycloalkoxy" means a cycloalkyl-O— group wherein the cycloalkyl group is as herein described.

As used herein, the term "cycloalkylalkyl" means a cycloalkyl-alkyl-group wherein the cycloalkyl and alkyl groups are as herein described.

As used herein, the term "aryl" refers to a substituted or unsubstituted, mono- or bicyclic hydrocarbon aromatic ring system having 6 to 10 ring carbon atoms. Examples include phenyl and naphthyl. Preferred aryl groups include unsubstituted or substituted phenyl and naphthyl groups. Included within the definition of "aryl" are fused ring systems, including, for example, ring systems in which an aromatic ring is fused to a cycloalkyl ring. Examples of such fused ring systems include, for example, indane, indene, and tetrahydronaphthalene.

As used herein, the term "aryloxy" means an aryl-O— group wherein the aryl group is as herein described. Exemplary aryloxy groups include the phenyloxy group.

As used herein, the terms "heterocycle", "heterocyclic" or "heterocyclyl" refer to a substituted or unsubstituted carbocyclic group in which the ring portion includes at least one heteroatom such as O, N, or S. The nitrogen and sulfur heteroatoms may be optionally oxidized, and the nitrogen may be optionally substituted in non-aromatic rings. Heterocycles are intended to include heteroaryl and heterocycloalkyl groups.

As used herein, the term "heteroaryl" refers to an aromatic group containing 5 to 10 ring carbon atoms in which one or more ring carbon atoms are replaced by at least one hetero atom such as —O—, —N—, or —S—. Examples of heteroaryl groups include pyrrolyl, furanyl, thienyl, pyrazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl. Included within the definition of "heteroaryl" are fused ring systems, including, for example, ring systems in which an aromatic ring is fused to a heterocycloalkyl ring. Examples of such fused ring systems include, for example, phthalamide, phthalic anhydride, indoline, isoindoline, tetrahydroisoquinoline, chroman, isochroman, chromene, and isochromene.

As used herein, the term "heterocycloalkyl" means a non-aromatic saturated monocyclic, bi- or multicyclic ring system containing 3 to 14 carbon atoms, preferably 5 to 10 carbon atoms, in which one or more of the carbon atoms in the ring system is/are hetero element(s) other than carbon, for example nitrogen, oxygen or sulfur. Preferred ring sizes of rings of the ring system include 5 to 6 ring atoms. The heterocycloalkyl may be optionally substituted. The nitrogen or sulphur atom of the heterocycloalkyl may also be optionally oxidized to the corresponding N-oxide, S-oxide or S,S-dioxide. Exemplary monocyclic heterocycloalkyl rings include piperidyl, pyrrolidinyl, piperazinyl, morpholinyl, imidazolidinyl, pyrazolidinyl, thiomorpholinyl, thiazolidinyl, 1,3-dioxolanyl, 1,4-dioxanyl, tetrahydrofuranyl, tetrahydrothiophenyl, tetrahydrothiopyranyl.

As used herein, the term "arylalkyl" or "aralkyl" refers to an aryl group that is substituted with an alkyl group. Examples of arylalkyl groups include, but are not limited to, tolyl, phenylethyl, naphthylmethyl, etc.

As used herein, the term "alkylaryl" or "alkaryl" refers to an alkyl group that is substituted with an aryl group. Examples of alkylaryl groups include, but are not limited to, benzyl, diphenylmethyl, triphenylmethyl, diphenylethyl, etc.

As used herein, the terms "alkyl", "aryl", "heteroaryl", and the likes refers also to the corresponding "alkylene", "arylene", "heteroarylene", and the likes which are formed by the removal of two hydrogen atoms.

As used herein the term "dialkylaminoalkyl" means a $(Alk_1)(Alk_2)N$-alkyl- wherein $Alk_1$ and $Alk_2$ denote an alkyl group, said alkyl group being as defined herein.

As used herein "alkyl, cycloalkyl, alkene, cycloalkene, alkyne, aryl, alkyaryl, arylalkyl . . . bearing at least one function chosen from ether and ester" refers alkyl, cycloalkyl, alkene, cycloalkene, alkyne, aryl, alkylaryl, arylalkyl . . . bearing ether or ester as side chains, or to ether or ester being included in the main chain of either alkyl, cycloalkyl, alkene, cycloalkene, alkyne, aryl, alkylaryl, arylalkyl . . .

As used herein, the term "subject" refers to a warm blooded animal such as a mammal, preferably a human, or a human child, which is afflicted with, or has the potential to be afflicted with one or more diseases and conditions described herein.

As used herein, a "therapeutically effective amount" refers to an amount of a compound of the present invention effective to prevent or treat the symptoms of particular disorder. Such disorders include, but are not limited to, those pathological and neurological disorders associated with the aberrant activity of the receptors described herein, wherein the treatment or prevention comprises inhibiting, inducing, or enhancing the activity thereof by contacting the receptor with a compound of the present invention.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

All other terms used in the description of the present invention have their meanings as is well known in the art.

In another aspect, the present invention is directed to pharmaceutically acceptable salts of the compounds described above. As used herein, "pharmaceutically acceptable salts" includes salts of compounds of the present invention derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, para-toluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

In addition to pharmaceutically-acceptable salts, other salts are included in the invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent. Such solvates are within the scope of the present invention.

In another aspect, the present invention is directed to pharmaceutically acceptable esters of the compounds described above. As used herein, "pharmaceutically acceptable esters" includes esters of compounds of the present invention which are active and non-toxic. In particular one of the part of the ester is a compound of Formula I bearing at least a hydroxy or a carboxylic function while the other is an alkyl, an alkene, an alkyne or an carbocycle bearing a carboxylic acid or a hydroxy function to form the ester bond with the hydroxy or carboxylic function of the formula I compound.

It is recognized that compounds of the present invention may exist in various stereoisomeric forms. As such, the compounds of the present invention include both diastereomers and enantiomers. The compounds are normally prepared as racemates and can conveniently be used as such, but individual enantiomers can be isolated or synthesized by conventional techniques if so desired. Such racemates and individual enantiomers and mixtures thereof form part of the present invention.

It is well-known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. *Stereochemistry of Organic Compounds*; Wiley: New York, 1994, and Jacques, J., et al. *Enantiomers, Racemates, and Resolutions*; Wiley: New York, 1981, each incorporated by reference herein in their entireties.

Synthesis

The compounds of the present invention may be prepared in a number of methods well known to those skilled in the art, including, but not limited to those described below, or through modifications of these methods by applying standard techniques known to those skilled in the art of organic synthesis. All processes disclosed in association with the present invention are contemplated to be practiced on any scale, including milligram, gram, multigram, kilogram, multikilogram or commercial industrial scale.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from active starting materials or by deliberate chiral synthesis of target centers.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, John Wiley and Sons, 1991; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethylformamide; alcohols such as ethanol and methanol and ethers, such as diethyl ether and tetrahydrofuran.

The reactions can take place over a wide range of temperatures. In general, we find it convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary, after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, reprecipitation or the various chromatography techniques, notably column chromatography or preparative thin layer chromatography.

The process of preparation of a compound of formula (I) is another object of the present invention.

Representative schemes of the processes of the invention are summarized below. Unless otherwise indicated all substituents in the synthetic Schemes are as previously defined.

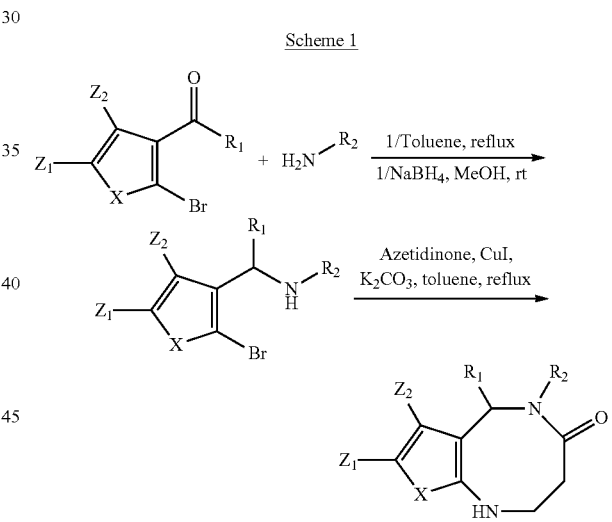

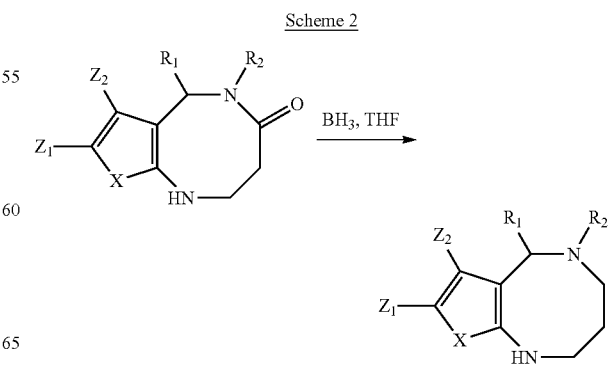

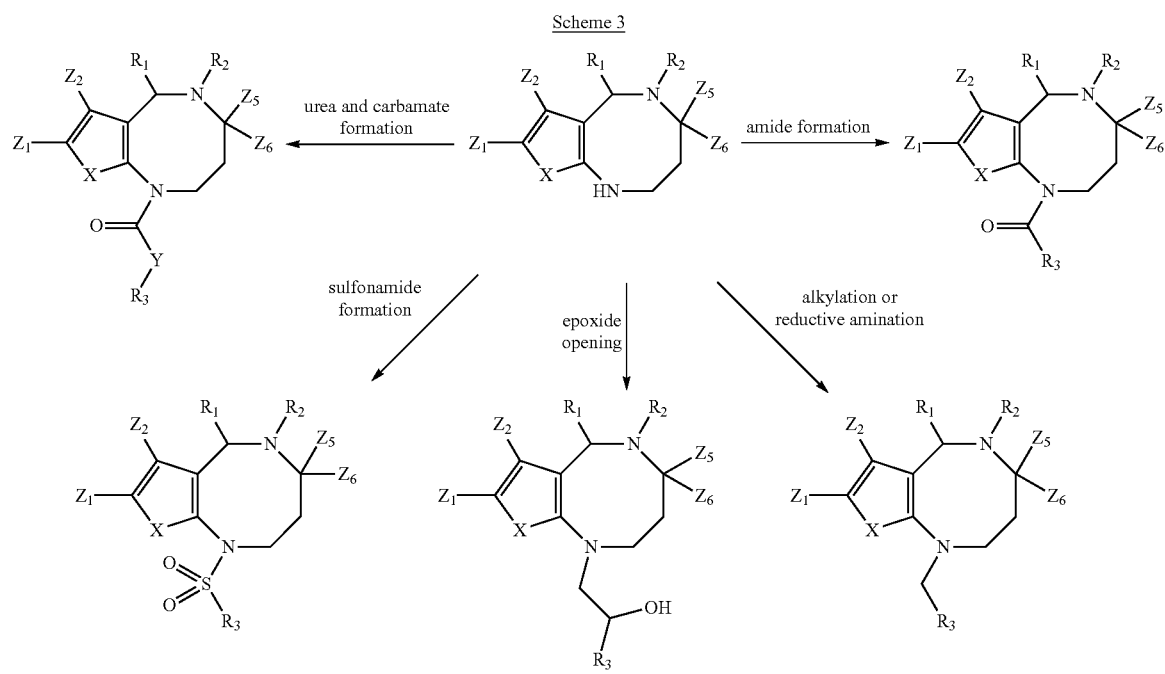
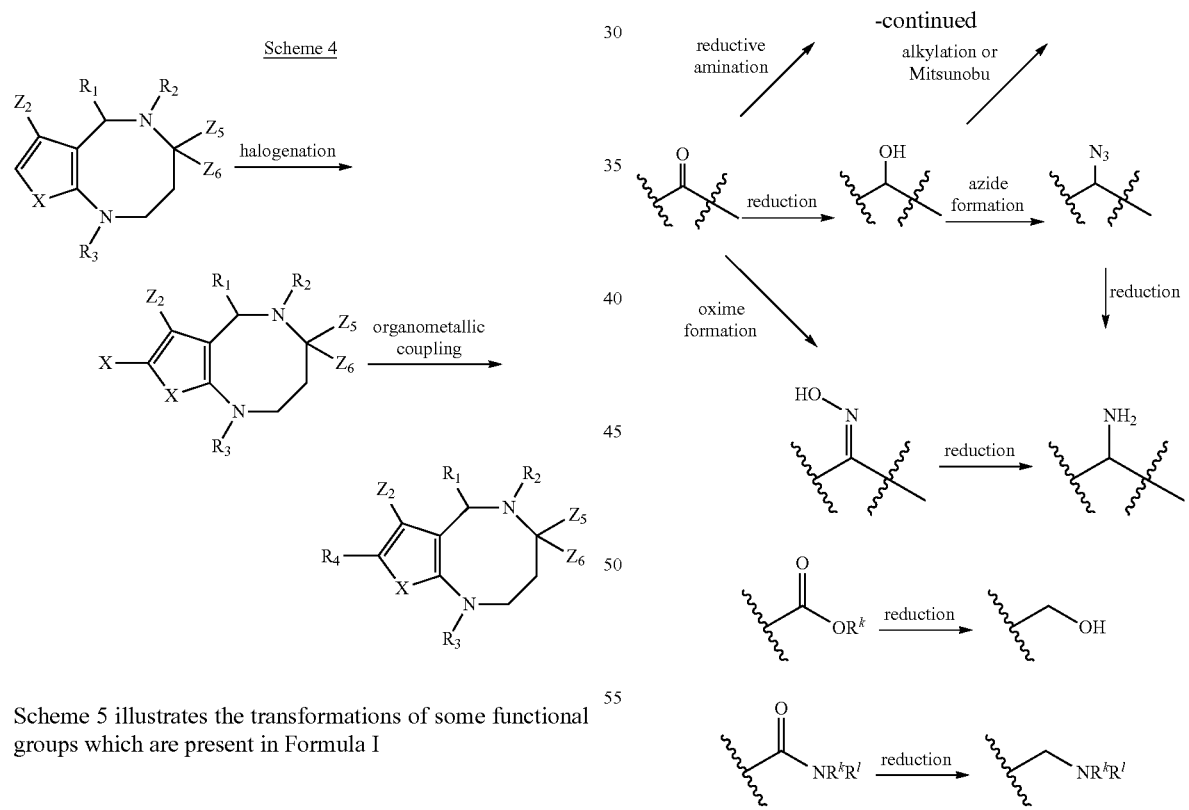
Scheme 5 illustrates the transformations of some functional groups which are present in Formula I
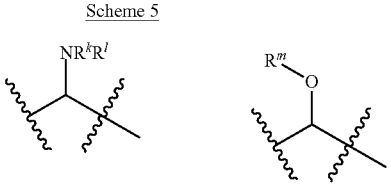
EXAMPLES
Other features of the invention will become apparent in the course of the following descriptions of exemplary embodiments. These examples are given for illustration of the invention and are not intended to be limiting thereof.

Example 1

Preparation of 5-cyclopropyl-8-methoxy-2,3,5,6-tetrahydrobenzo[b][1,5]diazocin-4(1H)-one N-(2-bromo-5-methoxybenzyl)cyclopropanamine

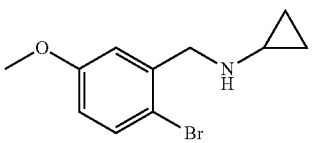

In a flask fitted with a Dean-Stark trap was introduced 2-bromo-5-methoxybenzaldehyde (5.68 g, 26.41 mmol), cyclopropylamine (3.02 g, 52.83 mmol) and toluene (70 ml). The reaction mixture was stirred at room temperature for 1 hour and then at reflux for 4 hours. The solution was then concentrated to give a yellow oil to which was added methanol (30 ml). The reaction mixture was cooled on icebath followed by portionwise addition of sodium borohydride (2.00 g, 52.83 mmol). After complete addition, the reaction mixture was stirred 2 hours at room temperature, and then water (70 ml) was added. The crude product was isolated by extraction with dichloromethane and the combined organic phases were dried over sodium sulfate, filtered, and finally evaporated under reduced pressure.

Purification by silica gel flash chromatography (pentane/ethyl acetate: 95/5) gave the desired compound (6.48 g, 96%) as a pale yellow oil.

$^1$H NMR (300 MHz, CDCl$_3$), δ 7.42 (d, J=8.7, 1H), 6.95 (d, J=3.1, 1H), 6.68 (dd, J=3.1, 8.7, 1H), 3.88 (s, 2H), 3.79 (s, 3H), 2.12 (m, 1H), 0.45 (m, 4H).

MS (ES+): [M+H]$^+$=256.0.

5-cyclopropyl-8-methoxy-2,3,5,6-tetrahydrobenzo[b][1,5]diazocin-4(1H)-one

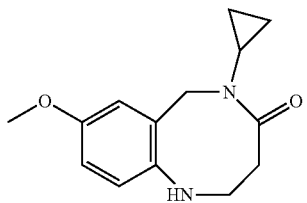 [SMILES: COc1ccc2c(c1)CN(C1CC1)C(=O)CCN2]

The method of Buchwald et al. (*J. Am. Chem. Soc.* 2004, 126, 3529-3533) was used with minor modifications.

To a mixture of copper(I) iodide (481 mg, 2.53 mmol), 2-azetidinone (3.60 g, 50.60 mmol) and potassium carbonate (6.99 g, 50.60 mmol) in dry and degassed toluene (21 ml) was added a solution of N-(2-bromo-5-methoxybenzyl)cyclopropanamine (6.48 g, 25.30 mmol) prepared as above and N,N'-dimethyletylenediamine (223.0 mg, 2.53 mmol) in dry and degassed toluene (31 ml). The resulting mixture was stirred at 110° C. for 16 hours. After cooling to room, temperature, aqueous ammonia (10%, 180 ml) was added and the resulting mixture was extracted with dichloromethane. The organic phases were washed with water and brine, dried over sodium sulfate and concentrated. Purification by silica gel flash chromatography (dichloromethane/methanol (saturated with ammonia): 95/5) gave the desired compound (2.64 g, 42%).

$^1$H NMR (300 MHz, CDCl$_3$), δ 6.98 (m, 1H), 6.86 (d, J=2.9, 1H), 6.74 (dd, J=2.9, 8.6, 1H), 4.50 (s, 2H), 3.78 (s, 3H), 3.29 (m, 2H), 2.87 (m, 2H), 2.44 (m, 1H), 0.92 (m, 2H), 0.71 (m, 2H).

MS (ES+): [M+H]$^+$=247.4.

Example 2

Preparation of 5-cyclopropyl-1-(2-hydroxy-3-phenoxypropyl)-8-methoxy-2,3,5,6-tetrahydrobenzo[b][1,5]diazocin-4(1H)-one 5-cyclopropyl-1-(2-hydroxy-3-phenoxypropyl)-8-methoxy-2,3,5,6-tetrahydrobenzo[b][1,5]diazocin-4(1H)-one

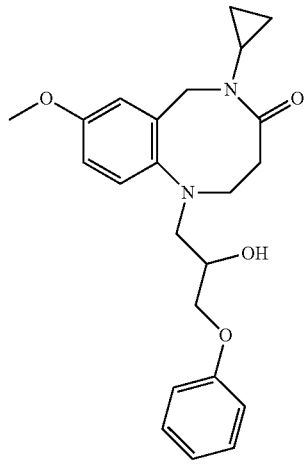 [SMILES: COc1ccc2c(c1)CN(C1CC1)C(=O)CCN2CC(O)COc1ccccc1]

To a mixture of 5-cyclopropyl-8-methoxy-2,3,5,6-tetrahydrobenzo[b][1,5]diazocin-4(1H)-one (50.0 mg, 0.203 mmol) from Example 1 and magnesium trifluoromethanesulfonate (32.7 mg, 0.102 mmol) in acetonitrile (1.5 ml) was added 2-(phenoxymethyl)oxirane (30.5 mg, 0.203 mmol) and the resulting mixture was stirred at 75° C. for 100 hours. After cooling to room temperature was added sodium bicarbonate (saturated aqueous) and the mixture was extracted with dichloromethane. The organic phases were filtered through a pad of sodium sulfate and the filtrate evaporated. Preparative thin layer chromatography (EtOAc/MeOH: 95/5) of the obtained residue, gave the desired compound as a brown oil (52 mg, 65%).

$^1$H NMR (300 MHz, Tetrachloroethane-d$_2$, 125° C.), δ 7.31 (dd, J=7.9, 2H), 7.10 (d, J=8.3, 1H), 6.93 (m, 5H), 4.54 (s, 2H), 4.06 (m, 3H), 3.83 (s, 3H), 3.56 (dd, J=3.7, 13.5, 1H), 3.35 (m, 3H), 2.87 (dd, J=5.8, 2H), 2.54 (m, 1H), 0.87 (m, 2H), 0.71 (m, 2H).

MS (ES+): [M+H]$^+$=397.6

Example 3

Preparation of 1-(4-chlorophenethyl)-5-cyclopropyl-8-methoxy-2,3,5,6-tetrahydrobenzo[b][1,5]diazocin-4(1H)-one 2-(4-chlorophenyl)acetaldehyde

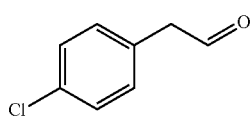

To a solution of 2-(4-chlorophenyl)ethanol (2.00 g, 12.77 mmol) in dichloromethane (100 ml) was added Dess-Martin periodinane (8.12 g, 19.16 mmol) and the mixture was stirred at room temperature over weekend. Then was added diethylether (150 ml) and the resulting mixture was washed with a 1:1 solution (150 ml) of sodium carbonate (aqueous saturated) and sodium thiosulfate (aqueous saturated) and then with sodium bicarbonate (aqueous saturated) and finally with brine. The organic phase was then dried over sodium sulfate and evaporated. Silica gel flash chromatography (pentan/ethylacetate:9/1) afforded the desired compound (0.834 g, 42%) as a white solid.

$^1$H NMR (300 MHz, CDCl$_3$), δ 9.74 (t, J=2.0, 1H), 7.34 (d, J=8.3, 2H), 7.15 (d, J=8.3, 2H), 3.68 (d, J=2.0, 2H).

1-(4-chlorophenethyl)-5-cyclopropyl-8-methoxy-2,3,5,6-tetrahydrobenzo[b][1,5]diazocin-4(1H)-one

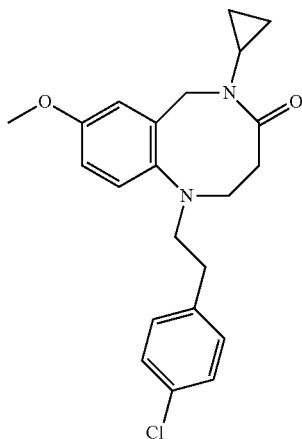 [SMILES: COc1ccc2c(c1)CN(C1CC1)C(=O)CCN2CCc1ccc(Cl)cc1]

To a solution of 5-cyclopropyl-8-methoxy-2,3,5,6-tetrahydrobenzo[b][1,5]diazocin-4(1H)-one (50.0 mg, 0.203 mmol) from Example 1 in dichloroethane (2 ml) at 0° C. was added acetic acid (0.035 ml, 0.609 mmol), 2-(4-chlorophenyl)acetaldehyde (47.0 mg, 0.304 mmol) prepared as above and sodium triacetoxyborohydride (129.0 mg, 0.609 mmol). The mixture was stirred overnight at room temperature and then sodium bicarbonate was added followed by extraction with dichloromethane. The organic phases were dried over sodium sulfate, filtered and concentrated. Preparative thin layer chromatography (pentane/ethyl acetate: 1/1) of the obtained residue gave the desired compound as a yellow oil (59 mg, 76%).

MS (ES+): [M+H]$^+$=385.4.

Example 4

Preparation of 5-cyclopropyl-8-methoxy-1-(5-methylisoxazole-3-carbonyl)-2,3,5,6-tetrahydrobenzo[b][1,5]diazocin-4(1H)-one 5-cyclopropyl-8-methoxy-1-(5-methylisoxazole-3-carbonyl)-2,3,5,6-tetrahydrobenzo[b][1,5]diazocin-4(1H)-one

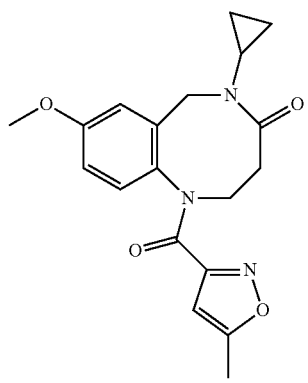 [SMILES: COc1ccc2c(c1)CN(C1CC1)C(=O)CCN2C(=O)c1cc(C)on1]

To a solution of 5-cyclopropyl-8-methoxy-2,3,5,6-tetrahydrobenzo[b][1,5]diazocin-4(1H)-one (50.0 mg, 0.203 mmol) from Example 1 in dichloroethane (2.0 ml) was added triethylamine (0.057 ml, 0.406 mmol) and 5-methylisoxazole-3-carbonyl chloride (32.5 mg, 0.223 mmol). The reaction mixture was stirred at room temperature overnight and then quenched with saturated aqueous sodium bicarbonate, followed by extraction with dichloromethane. The combined organic phases were dried over sodium sulfate, filtered and concentrated. Preparative thin layer chromatography (ethyl acetate/methanol:98/2) of the crude residue gave the desired compound (53 mg, 74%).

$^1$H NMR (300 MHz, CDCl$_3$), δ 6.99 (d, J=8.6, 1H), 6.93 (d, J=2.8, 1H), 6.72 (dd, J=2.8, 8.6, 1H), 6.02 (s, 1H), 5.07 (dd, J=6.6, 13.6, 1H), 4.74 (d, J=14.9, 1H), 4.06 (d, J=14.9, 1H), 3.79 (s, 3H), 3.02 (m, 2H), 2.71 (dd, J=6.6, 13.6, 1H), 2.47 (m, 1H), 2.31 (s, 3H), 1.07 (m, 1H), 0.82 (m, 2H), 0.60 (m, 1H).

MS (ES+): [M+H]$^+$=356.4.

Example 5

Preparation of 5-cyclopropyl-1-(2-(4-fluorophenyl)-2-oxoethyl)-8-methoxy-2,3,5,6-tetrahydrobenzo[b][1,5]diazocin-4(1H)-one 5-cyclopropyl-1-(2-(4-fluorophenyl)-2-oxoethyl)-8-methoxy-2,3,5,6-tetrahydrobenzo[b][1,5]diazocin-4(1H)-one

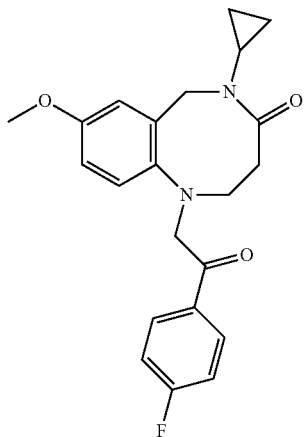 [SMILES: COc1ccc2c(c1)CN(C1CC1)C(=O)CCN2CC(=O)c1ccc(F)cc1]

A solution of 5-cyclopropyl-8-methoxy-2,3,5,6-tetrahydrobenzo[b][1,5]diazocin-4(1H)-one (100.0 mg, 0.406 mmol) from Example 1,2-bromo-1-(4-fluorophenyl)ethanone (105.7 mg, 0.487 mmol), diisopropyl ethylamine (0.106 ml, 0.609 mmol) in dioxane (1.5 ml) was stirred at 50° C. over weekend. The reaction mixture was cooled to RT, diluted with dichloromethane and washed with sodium bicarbonate. The organic phases were dried over sodium sulfate, filtered and concentrated. Preparative thin layer chromatography (ethyl acetate/methanol: 98/2) of the crude residue gave the desired compound (16 mg, 75%).

$^1$H NMR (300 MHz, Tetrachloroethane-d$_2$, 125° C.), δ 8.15 (m, 1H), 7.98 (m, 1H), 7.16 (m, 2H), 7.01 (d, J=8.9, 1H), 6.89 (m, 2H), 4.57 (d, J=14.7, 2H), 4.36 (s, 1H), 3.90 (s, 1H), 3.83 (s, 3H), 3.35 (dd, J=5.8, 1H), 2.84 (m, 2H), 2.53 (m, 1H), 0.91 (m, 2H), 0.73 (m, 2H).

MS (ES+): [M+H]$^+$=383.4.

Example 6

Preparation of 5-cyclopropyl-1-(2-(4-fluorophenyl)-2-hydroxyethyl)-8-methoxy-2,3,5,6-tetrahydrobenzo[b][1,5]diazocin-4(1H)-one 5-cyclopropyl-1-(2-(4-fluorophenyl)-2-hydroxyethyl)-8-methoxy-2,3,5,6-tetrahydrobenzo[b][1,5]diazocin-4(1H)-one

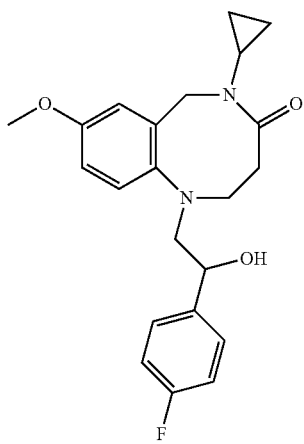 [SMILES: COc1ccc2c(c1)CN(C1CC1)C(=O)CCN2CC(O)c1ccc(F)cc1]

To a solution of 5-cyclopropyl-1-(2-(4-fluorophenyl)-2-oxoethyl)-8-methoxy-2,3,5,6-tetrahydrobenzo[b][1,5]diazocin-4(1H)-one (65.0 mg, 0.170 mmol) from Example 5 in ethanol (1 ml) was added sodium borohydride (6.4 mg, 0.170 mmol) and the reaction mixture was stirred at room temperature over weekend. Then was added acetone (0.062 ml) followed by dilution with dichloromethane. The resulting solution was washed with water and the organic phase was dried over sodium sulfate and filtered. Evaporation gave the desired product (30 mg, 46%).

MS (ES+): [M+H]$^+$=385.5.

Example 7

Preparation of 8-bromo-5-cyclopropyl-2,3,5,6-tetrahydrobenzo[b][1,5]diazocin-4(1H)-one 8-bromo-5-cyclopropyl-2,3,5,6-tetrahydrobenzo[b][1,5]diazocin-4(1H)-one

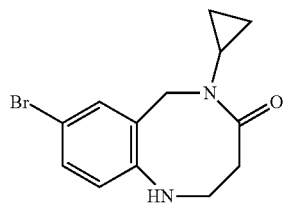 [SMILES: O=C1CCNc2ccc(Br)cc2CN1C1CC1]

Sodium perborate tetrahydrate (1.07 g, 6.94 mmol) was added in one portion to a suspension of KBr (0.770 g, 6.47 mmol), 5-cyclopropyl-2,3,5,6-tetrahydrobenzo[b][1,5]diazocin-4(1H)-one (1.00 g, 4.62 mmol) and ammonium molybdate tetrahydrate (0.114 mg, 0.092 mmol) in acetic acid (10 ml). The mixture was stirred at room temperature for 24 hours, then quenched with sodium carbonate (aqueous saturated) and a few drops of NaOH (10% aqueous). The mixture was extracted with ethyl acetate and the combined organic phases were washed with sodium carbonate, dried over sodium sulfate filtered and concentrated. Purification of the crude mixture by silica gel flash chromatography (0-20% methanol in ethyl acetate) gave the desired product as a brown solid (0.619 g, 45%).

$^1$H NMR (300 MHz, CDCl$_3$), δ 7.35 (d, J=2.3, 1H), 7.25 (dd, J=2.3, 8.3, 1H), 6.72 (d, J=8.3, 1H), 4.46 (s, 2H), 3.37 (t, J=6.0, 2H), 2.88 (t, J=6.0, 2H), 2.40 (m, 1H), 0.90 (m, 2H), 0.67 (m, 2H).

MS (ES+): [M+H]$^+$=296.2

Example 8

Insulin Secretion Response to Formula I compounds

The secretory responses of beta cell lines to glucose were tested as described in Merglen et al. Endocrinology, (2004) 145(2):667-78.

Briefly, after incubation with compounds from formula I or control vehicle, cells were maintained for 2 hours in glucose-free culture medium. The cells were then washed twice and preincubated for 30 minutes at 37° C. in glucose-free Krebs-Ringer bicarbonate HEPES buffer (KRBH: 135 mM NaCl, 3.6 mM KCl, 5 mM NaHCO$_3$, 0.5 mM NaH$_2$PO$_4$, 0.5 mM MgCl$_2$, 1.5 mM CaCl$_2$, and 10 mM HEPES, pH 7.4). BSA (0.1%) was added as an insulin carrier. Cells were subsequently washed with glucose-free KRBH and then incubated for 30 minutes at 37° C. in KRBH containing different concentrations of glucose. The reaction was stopped by placing the plates on ice; supernatants were collected to determine insulin secretion and cells were used for intracellular insulin content following acid-ethanol extraction. Insulin was measured by ELISA (Linco) according to the manufacturer's instructions.

For each active compound, insulin secretion was ranked (range 1 to 5) according to % increase versus control at most effective dose (i.e. 1: 90-110% of control; 2: 110-120% of control; 3: 120-140% of control; 4: 140-170% of control and 5: >170% of control).

The Table below shows the insulin secretion response to formula I compounds. Such compounds were prepared according to similar methods as disclosed in preceding examples or by well-known techniques by one of ordinary skill in the arts. Their mass spectral data are also reported therein.

| n° | NAME | Analytical data: HPLC-MS (M + H) | Insulin secretion (Min6 cell) Range 1 to 5 |
|---|---|---|---|
| 1 | 5-cyclopropyl-8-methoxy-2,3,5,6-tetrahydrobenzo[b][1,5]diazocin-4(1H)-one | 247.4 | 2 |
| 2 | 5-cyclopropyl-1-(2-hydroxy-3-phenoxypropyl)-8-methoxy-2,3,5,6-tetrahydrobenzo[b][1,5]diazocin-4(1H)-one | 397.6 | 3 |
| 3 | 1-(4-chlorophenethyl)-5-cyclopropyl-8-methoxy-2,3,5,6-tetrahydrobenzo[b][1,5]diazocin-4(1H)-one | 385.4 | 1 |
| 4 | 5-cyclopropyl-8-methoxy-1-(5-methylisoxazole-3-carbonyl)-2,3,5,6-tetrahydrobenzo[b][1,5]diazocin-4(1H)-one | 356.4 | 2 |
| 5 | 5-cyclopropyl-1-(2-(4-fluorophenyl)-2-oxoethyl)-8-methoxy-2,3,5,6-tetrahydrobenzo[b][1,5]diazocin-4(1H)-one | 383.4 | 3 |
| 6 | 5-cyclopropyl-1-(2-(4-fluorophenyl)-2-hydroxyethyl)-8-methoxy-2,3,5,6-tetrahydrobenzo[b][1,5]diazocin-4(1H)-one | 385.4 | 3 |
| 7 | 8-bromo-5-cyclopropyl-2,3,5,6-tetrahydrobenzo[b][1,5]diazocin-4(1H)-one | 296.2 | 1 |
| 8 | 5-cyclopropyl-8-fluoro-2,3,5,6-tetrahydrobenzo[b][1,5]diazocin-4(1H)-one | 235.4 | 3 |
| 9 | 5-cyclopropyl-2,3,5,6-tetrahydropyrido[2,3-b][1,5]diazocin-4(1H)-one | 218.4 | 2 |
| 10 | 8-fluoro-2,3,5,6-tetrahydrobenzo[b][1,5]diazocin-4(1H)-one | 195.3 | 4 |
| 11 | 5-cyclopropyl-8-methoxy-1-(2-oxo-2-phenylethyl)-2,3,5,6-tetrahydrobenzo[b][1,5]diazocin-4(1H)-one | 365.5 | 1 |
| 12 | 5-cyclopropyl-1-(2-(2,5-dimethoxyphenyl)-2-oxoethyl)-8-methoxy-2,3,5,6-tetrahydrobenzo[b][1,5]diazocin-4(1H)-one | 425.6 | 1 |
| 13 | 5-cyclopropyl-8-methoxy-1-(2-(2-methoxyphenyl)-2-oxoethyl)-2,3,5,6-tetrahydrobenzo[b][1,5]diazocin-4(1H)-one | 395.6 | 1 |
| 14 | 1-(2-(4-chlorophenyl)-2-oxoethyl)-5-cyclopropyl-8-methoxy-2,3,5,6-tetrahydrobenzo[b][1,5]diazocin-4(1H)-one | 399.4 | 3 |
| 15 | 5-cyclopropyl-1-(2-(2,3-dihydrobenzo[b][1,4]dioxin-6-yl)-2-oxoethyl)-8-methoxy-2,3,5,6-tetrahydrobenzo[b][1,5]diazocin-4(1H)-one | 423.4 | 3 |
| 16 | 5-cyclopropyl-8-methoxy-1-(2-oxo-2-(4-(pyrrolidin-1-yl)phenyl)ethyl)-2,3,5,6-tetrahydrobenzo[b][1,5]diazocin-4(1H)-one | 434.5 | 4 |
| 17 | 5-cyclopropyl-1-(2-hydroxy-2-phenylethyl)-8-methoxy-2,3,5,6-tetrahydrobenzo[b][1,5]diazocin-4(1H)-one | 367.5 | 2 |
| 18 | (R)-1-(3-(benzyloxy)-2-hydroxypropyl)-5-cyclopropyl-8-methoxy-2,3,5,6-tetrahydrobenzo[b][1,5]diazocin-4(1H)-one | 411.5 | 2 |
| 19 | (R)-1-(3-(benzyloxy)-2-hydroxypropyl)-5-cyclopropyl-8-fluoro-2,3,5,6-tetrahydrobenzo[b][1,5]diazocin-4(1H)-one | 399.5 | 1 |
| 20 | 5-cyclopropyl-8-methoxy-1-(2-(3-methoxyphenyl)-2-oxoethyl)-2,3,5,6-tetrahydrobenzo[b][1,5]diazocin-4(1H)-one | 395.5 | 1 |
| 21 | 5-cyclopropyl-8-methoxy-1-(2-(4-methoxyphenyl)-2-oxoethyl)-2,3,5,6-tetrahydrobenzo[b][1,5]diazocin-4(1H)-one | 395.5 | 2 |
| 22 | 5-cyclopropyl-1-(2-(3-fluorophenyl)-2-oxoethyl)-8-methoxy-2,3,5,6-tetrahydrobenzo[b][1,5]diazocin-4(1H)-one | 383.4 | 2 |
| 23 | 5-cyclopropyl-8-methoxy-1-(2-oxo-2-(4-(trifluoromethoxy)phenyl)ethyl)-2,3,5,6-tetrahydrobenzo[b][1,5]diazocin-4(1H)-one | 449.4 | 1 |
| 24 | 5-cyclopropyl-1-(2-(3,4-difluorophenyl)-2-oxoethyl)-8-methoxy-2,3,5,6-tetrahydrobenzo[b][1,5]diazocin-4(1H)-one | 401.4 | 2 |
| 25 | 5-cyclopropyl-1-(2-(2,5-dimethoxyphenyl)-2-hydroxyethyl)-8-methoxy-2,3,5,6-tetrahydrobenzo[b][1,5]diazocin-4(1H)-one | 427.5 | 2 |
| 26 | 5-cyclopropyl-1-(2-hydroxy-2-(2-methoxyphenyl)ethyl)-8-methoxy-2,3,5,6-tetrahydrobenzo[b][1,5]diazocin-4(1H)-one | 397.5 | 2 |
| 27 | 1-(2-(4-chlorophenyl)-2-hydroxyethyl)-5-cyclopropyl-8-methoxy-2,3,5,6-tetrahydrobenzo[b][1,5]diazocin-4(1H)-one | 401.9 | 4 |

-continued

| n° | NAME | Analytical data: HPLC-MS (M + H) | Insulin secretion (Min6 cell) Range 1 to 5 |
|---|---|---|---|
| 28 | 5-cyclopropyl-1-(2-hydroxy-2-(4-(pyrrolidin-1-yl)phenyl)ethyl)-8-methoxy-2,3,5,6-tetrahydrobenzo[b][1,5]diazocin-4(1H)-one | 436.6 | 3 |
| 29 | 5-cyclopropyl-1-(2-(2,3-dihydrobenzo[b][1,4]dioxin-6-yl)-2-hydroxyethyl)-8-methoxy-2,3,5,6-tetrahydrobenzo[b][1,5]diazocin-4(1H)-one | 425.5 | 2 |
| 30 | 5-cyclopropyl-1-(2-hydroxy-2-(3-methoxyphenyl)ethyl)-8-methoxy-2,3,5,6-tetrahydrobenzo[b][1,5]diazocin-4(1H)-one | 397.5 | 1 |
| 31 | 5-cyclopropyl-1-(2-(3-fluorophenyl)-2-hydroxyethyl)-8-methoxy-2,3,5,6-tetrahydrobenzo[b][1,5]diazocin-4(1H)-one | 385.4 | 1 |
| 32 | 5-cyclopropyl-1-(2-hydroxy-2-(4-methoxyphenyl)ethyl)-8-methoxy-2,3,5,6-tetrahydrobenzo[b][1,5]diazocin-4(1H)-one | 397.5 | 3 |
| 33 | 5-cyclopropyl-1-(2-hydroxy-2-(4-(trifluoromethoxy)phenyl)ethyl)-8-methoxy-2,3,5,6-tetrahydrobenzo[b][1,5]diazocin-4(1H)-one | 451.5 | 2 |
| 34 | 5-cyclopropyl-1-(2-(3,4-difluorophenyl)-2-hydroxyethyl)-8-methoxy-2,3,5,6-tetrahydrobenzo[b][1,5]diazocin-4(1H)-one | 403.4 | 1 |
| 35 | 5-cyclopropyl-8-fluoro-1-(2-oxo-2-phenylethyl)-2,3,5,6-tetrahydrobenzo[b][1,5]diazocin-4(1H)-one | 353.4 | 1 |
| 36 | 5-cyclopropyl-8-fluoro-1-(2-(2-methoxyphenyl)-2-oxoethyl)-2,3,5,6-tetrahydrobenzo[b][1,5]diazocin-4(1H)-one | 383.4 | 2 |
| 37 | 5-cyclopropyl-8-fluoro-1-(2-(3-methoxyphenyl)-2-oxoethyl)-2,3,5,6-tetrahydrobenzo[b][1,5]diazocin-4(1H)-one | 383.4 | 4 |
| 38 | 5-cyclopropyl-8-fluoro-1-(2-(4-methoxyphenyl)-2-oxoethyl)-2,3,5,6-tetrahydrobenzo[b][1,5]diazocin-4(1H)-one | 383.4 | 1 |
| 39 | 5-cyclopropyl-1-(2-(2,5-dimethoxyphenyl)-2-oxoethyl)-8-fluoro-2,3,5,6-tetrahydrobenzo[b][1,5]diazocin-4(1H)-one | 413.5 | 3 |
| 40 | 5-cyclopropyl-8-fluoro-1-(2-(4-fluorophenyl)-2-oxoethyl)-2,3,5,6-tetrahydrobenzo[b][1,5]diazocin-4(1H)-one | 371.4 | 3 |
| 41 | 5-cyclopropyl-8-fluoro-1-(2-(3-fluorophenyl)-2-oxoethyl)-2,3,5,6-tetrahydrobenzo[b][1,5]diazocin-4(1H)-one | 371.4 | 3 |
| 42 | 5-cyclopropyl-8-fluoro-1-(2-oxo-2-(4-(trifluoromethoxy)phenyl)ethyl)-2,3,5,6-tetrahydrobenzo[b][1,5]diazocin-4(1H)-one | 437.4 | 1 |
| 43 | 5-cyclopropyl-1-(2-(3,4-difluorophenyl)-2-oxoethyl)-8-fluoro-2,3,5,6-tetrahydrobenzo[b][1,5]diazocin-4(1H)-one | 389.4 | 2 |
| 44 | 1-(2-(4-chlorophenyl)-2-oxoethyl)-5-cyclopropyl-8-fluoro-2,3,5,6-tetrahydrobenzo[b][1,5]diazocin-4(1H)-one | 387.8 | 1 |
| 45 | 5-cyclopropyl-1-(2-(2,5-dimethoxyphenyl)-2-hydroxyethyl)-8-fluoro-2,3,5,6-tetrahydrobenzo[b][1,5]diazocin-4(1H)-one | 415.5 | 1 |
| 46 | 5-cyclopropyl-8-fluoro-1-(2-(4-fluorophenyl)-2-hydroxyethyl)-2,3,5,6-tetrahydrobenzo[b][1,5]diazocin-4(1H)-one | 373.4 | 2 |
| 47 | 5-cyclopropyl-8-fluoro-1-(2-(3-fluorophenyl)-2-hydroxyethyl)-2,3,5,6-tetrahydrobenzo[b][1,5]diazocin-4(1H)-one | 373.4 | 2 |
| 48 | 5-cyclopropyl-8-fluoro-1-(2-hydroxy-2-(4-(trifluoromethoxy)phenyl)ethyl)-2,3,5,6-tetrahydrobenzo[b][1,5]diazocin-4(1H)-one | 439.4 | 2 |
| 49 | 5-cyclopropyl-1-(2-(3,4-difluorophenyl)-2-hydroxyethyl)-8-fluoro-2,3,5,6-tetrahydrobenzo[b][1,5]diazocin-4(1H)-one | 391.4 | 5 |
| 50 | 1-(2-(4-chlorophenyl)-2-hydroxyethyl)-5-cyclopropyl-8-fluoro-2,3,5,6-tetrahydrobenzo[b][1,5]diazocin-4(1H)-one | 389.9 | 2 |
| 51 | 5-cyclopropyl-1-(2-hydroxy-3-(4-methoxyphenoxy)propyl)-8-methoxy-2,3,5,6-tetrahydrobenzo[b][1,5]diazocin-4(1H)-one | 427.5 | 2 |
| 52 | 5-cyclopropyl-8-fluoro-1-(2-hydroxy-3-phenoxypropyl)-2,3,5,6-tetrahydrobenzo[b][1,5]diazocin-4(1H)-one | 385.4 | 1 |
| 53 | 5-cyclopropyl-8-fluoro-1-(2-hydroxy-3-(4-methoxyphenoxy)propyl)-2,3,5,6-tetrahydrobenzo[b][1,5]diazocin-4(1H)-one | 415.5 | 1 |
| 54 | 8-methoxy-2,3,5,6-tetrahydrobenzo[b][1,5]diazocin-4(1H)-one | 207.2 | 1 |
| 55 | 5-cyclopropyl-1-(2-(2,3-dihydrobenzo[b][1,4]dioxin-6-yl)-2-oxoethyl)-8-fluoro-2,3,5,6-tetrahydrobenzo[b][1,5]diazocin-4(1H)-one | 411.4 | 2 |

-continued

| n° | NAME | Analytical data: HPLC-MS (M + H) | Insulin secretion (Min6 cell) Range 1 to 5 |
|---|---|---|---|
| 56 | 5-cyclopropyl-8-fluoro-1-(2-oxo-2-(4-(pyrrolidin-1-yl)phenyl)ethyl)-2,3,5,6-tetrahydrobenzo[b][1,5]diazocin-4(1H)-one | 422.5 | 2 |
| 57 | 5-cyclopropyl-8-fluoro-1-(2-hydroxy-2-(2-methoxyphenyl)ethyl)-2,3,5,6-tetrahydrobenzo[b][1,5]diazocin-4(1H)-one | 385.4 | 2 |
| 58 | 5-cyclopropyl-8-fluoro-1-(2-hydroxy-2-(3-methoxyphenyl)ethyl)-2,3,5,6-tetrahydrobenzo[b][1,5]diazocin-4(1H)-one | 385.4 | 2 |
| 59 | 5-cyclopropyl-8-fluoro-1-(2-hydroxy-2-(4-methoxyphenyl)ethyl)-2,3,5,6-tetrahydrobenzo[b][1,5]diazocin-4(1H)-one | 385.4 | 2 |
| 60 | 5-cyclopropyl-1-(2-(2,3-dihydrobenzo[b][1,4]dioxin-6-yl)-2-hydroxyethyl)-8-fluoro-2,3,5,6-tetrahydrobenzo[b][1,5]diazocin-4(1H)-one | 413.5 | 2 |
| 61 | 5-cyclopropyl-8-fluoro-1-(2-hydroxy-2-phenylethyl)-2,3,5,6-tetrahydrobenzo[b][1,5]diazocin-4(1H)-one | 355.4 | 3 |
| 62 | 5-cyclopropyl-2,3,5,6-tetrahydropyrido[3,4-b][1,5]diazocin-4(1H)-one | 218.3 | 2 |
| 63 | 2-(7-(allyloxy)-5-cyclopentyl-8-methoxy-4-oxo-3,4,5,6-tetrahydrobenzo[b][1,5]diazocin-1(2H)-yl)acetic acid | 389.5 | 1 |
| 64 | 5-cyclopropyl-8-fluoro-1-(2-hydroxy-2-(4-(pyrrolidin-1-yl)phenyl)ethyl)-2,3,5,6-tetrahydrobenzo[b][1,5]diazocin-4(1H)-one | 424.5 | 5 |
| 65 | 5-cyclopropyl-8-fluoro-1-(3-(4-fluorophenoxy)-2-hydroxypropyl)-2,3,5,6-tetrahydrobenzo[b][1,5]diazocin-4(1H)-one | 403.4 | 3 |
| 66 | (S)-1-(3-(benzyloxy)-2-hydroxypropyl)-5-cyclopropyl-8-fluoro-2,3,5,6-tetrahydrobenzo[b][1,5]diazocin-4(1H)-one | 399.5 | 1 |
| 67 | (S)-1-(3-(benzyloxy)-2-hydroxypropyl)-5-cyclopropyl-8-methoxy-2,3,5,6-tetrahydrobenzo[b][1,5]diazocin-4(1H)-one | 411.5 | 3 |
| 68 | (R)-5-cyclopropyl-1-(2,3-dihydroxypropyl)-8-methoxy-2,3,5,6-tetrahydrobenzo[b][1,5]diazocin-4(1H)-one | 321.4 | 3 |
| 69 | 5-cyclopropyl-8-fluoro-1-(4-fluorobenzoyl)-2,3,5,6-tetrahydrobenzo[b][1,5]diazocin-4(1H)-one | 357.4 | 1 |
| 70 | 5-cyclopropyl-8-fluoro-1-nicotinoyl-2,3,5,6-tetrahydrobenzo[b][1,5]diazocin-4(1H)-one | 340.4 | 1 |
| 71 | 5-cyclopropyl-8-fluoro-1-(2-(4-fluorophenyl)acetyl)-2,3,5,6-tetrahydrobenzo[b][1,5]diazocin-4(1H)-one | 371.4 | 4 |
| 72 | 1-benzyl-5-cyclopropyl-8-fluoro-2,3,5,6-tetrahydrobenzo[b][1,5]diazocin-4(1H)-one | 325.4 | 3 |
| 73 | 5-cyclopropyl-8-fluoro-1-phenethyl-2,3,5,6-tetrahydrobenzo[b][1,5]diazocin-4(1H)-one | 339.4 | 4 |
| 74 | 5-cyclopropyl-8-fluoro-1-(3-phenylpropyl)-2,3,5,6-tetrahydrobenzo[b][1,5]diazocin-4(1H)-one | 353.4 | 4 |
| 75 | 5-cyclopropyl-1-(4-fluorobenzoyl)-2,3,5,6-tetrahydropyrido[2,3-b][1,5]diazocin-4(1H)-one | 340.4 | 4 |
| 76 | 5-cyclopropyl-1-(2-(4-fluorophenyl)acetyl)-2,3,5,6-tetrahydropyrido[2,3-b][1,5]diazocin-4(1H)-one | 354.5 | 5 |
| 77 | 5-cyclopropyl-1-nicotinoyl-2,3,5,6-tetrahydropyrido[2,3-b][1,5]diazocin-4(1H)-one | 323.4 | 5 |
| 78 | 8-chloro-5-cyclopropyl-2,3,5,6-tetrahydrobenzo[b][1,5]diazocin-4(1H)-one | 251.7 | 3 |
| 79 | (R)-1-(3-(benzyloxy)-2-hydroxypropyl)-8-chloro-5-cyclopropyl-2,3,5,6-tetrahydrobenzo[b][1,5]diazocin-4(1H)-one | 415.9 | 1 |
| 80 | 11-cyclopropyl-2,3,8,9,11,12-hexahydro[1,4]dioxino[2,3-h][1,5]benzodiazocin-10(7H)-one | 275.3 | 3 |
| 81 | 8-chloro-5-cyclopropyl-1-(2-hydroxy-3-phenoxypropyl)-2,3,5,6-tetrahydrobenzo[b][1,5]diazocin-4(1H)-one | 401.9 | 1 |
| 82 | 8-chloro-1-(2-(4-chlorophenyl)-2-oxoethyl)-5-cyclopropyl-2,3,5,6-tetrahydrobenzo[b][1,5]diazocin-4(1H)-one | 404.3 | 1 |
| 83 | 8-chloro-5-cyclopropyl-1-(2-(3-fluorophenyl)-2-oxoethyl)-2,3,5,6-tetrahydrobenzo[b][1,5]diazocin-4(1H)-one | 387.8 | 1 |
| 84 | 5-cyclopropyl-1-(isoxazole-5-carbonyl)-8-methoxy-2,3,5,6-tetrahydrobenzo[b][1,5]diazocin-4(1H)-one | 342.4 | 1 |
| 85 | 8-chloro-1-(2-(4-chlorophenyl)-2-hydroxyethyl)-5-cyclopropyl-2,3,5,6-tetrahydrobenzo[b][1,5]diazocin-4(1H)-one | 406.3 | 1 |
| 86 | 8-chloro-5-cyclopropyl-1-(2-(3-fluorophenyl)-2-hydroxyethyl)-2,3,5,6-tetrahydrobenzo[b][1,5]diazocin-4(1H)-one | 389.9 | 2 |

-continued

| n° | NAME | Analytical data: HPLC-MS (M + H) | Insulin secretion (Min6 cell) Range 1 to 5 |
|---|---|---|---|
| 87 | 8-bromo-5-cyclopropyl-2,3,5,6-tetrahydrobenzo[b][1,5]diazocin-4(1H)-one | 296.2 | 1 |
| 88 | 7-[(2R)-3-(benzyloxy)-2-hydroxypropyl]-11-cyclopropyl-2,3,8,9,11,12-hexahydro[1,4]dioxino[2,3-h][1,5]benzodiazocin-10(7H)-one | 439.5 | 1 |
| 89 | (R)-1-(3-(4-chlorophenoxy)-2-hydroxypropyl)-5-cyclopropyl-8-methoxy-2,3,5,6-tetrahydrobenzo[b][1,5]diazocin-4(1H)-one | 431.9 | 1 |
| 90 | (S)-1-(3-(4-chlorophenoxy)-2-hydroxypropyl)-5-cyclopropyl-8-methoxy-2,3,5,6-tetrahydrobenzo[b][1,5]diazocin-4(1H)-one | 431.9 | 1 |
| 91 | 11-cyclopropyl-7-(isoxazol-5-ylcarbonyl)-2,3,8,9,11,12-hexahydro[1,4]dioxino[2,3-h][1,5]benzodiazocin-10(7H)-one | 370.4 | 1 |
| 92 | 11-cyclopropyl-7-[(5-phenyl-1,3-oxazol-4-yl)carbonyl]-2,3,8,9,11,12-hexahydro[1,4]dioxino[2,3-h][1,5]benzodiazocin-10(7H)-one | 446.5 | 1 |
| 93 | 11-cyclopropyl-7-[2-(3-fluorophenyl)-2-oxoethyl]-2,3,8,9,11,12-hexahydro[1,4]dioxino[2,3-h][1,5]benzodiazocin-10(7H)-one | 411.4 | 1 |
| 94 | 7-[2-(4-chlorophenyl)-2-oxoethyl]-11-cyclopropyl-2,3,8,9,11,12-hexahydro[1,4]dioxino[2,3-h][1,5]benzodiazocin-10(7H)-one | 427.9 | 1 |
| 95 | 11-cyclopropyl-7-(2-hydroxy-3-phenoxypropyl)-2,3,8,9,11,12-hexahydro[1,4]dioxino[2,3-h][1,5]benzodiazocin-10(7H)-one | 425.5 | 1 |
| 96 | 11-cyclopropyl-7-[2-(3-fluorophenyl)-2-hydroxyethyl]-2,3,8,9,11,12-hexahydro[1,4]dioxino[2,3-h][1,5]benzodiazocin-10(7H)-one | 413.5 | 3 |
| 97 | 7-[2-(4-chlorophenyl)-2-hydroxyethyl]-11-cyclopropyl-2,3,8,9,11,12-hexahydro[1,4]dioxino[2,3-h][1,5]benzodiazocin-10(7H)-one | 429.9 | 2 |
| 98 | 5-cyclopropyl-8-methoxy-1-(5-phenyloxazole-4-carbonyl)-2,3,5,6-tetrahydrobenzo[b][1,5]diazocin-4(1H)-one | 418.5 | 2 |
| 99 | 5-cyclopropyl-1-(1,3-dimethyl-1H-pyrazole-5-carbonyl)-8-methoxy-2,3,5,6-tetrahydrobenzo[b][1,5]diazocin-4(1H)-one | 369.4 | 1 |
| 100 | 5-cyclopropyl-1-(3,5-dimethylisoxazole-4-carbonyl)-8-methoxy-2,3,5,6-tetrahydrobenzo[b][1,5]diazocin-4(1H)-one | 370.4 | 1 |
| 101 | 5-cyclopropyl-8-methoxy-1-(pyrazine-2-carbonyl)-2,3,5,6-tetrahydrobenzo[b][1,5]diazocin-4(1H)-one | 353.4 | 2 |
| 102 | 5-cyclopropyl-1-(isoxazole-5-carbonyl)-2,3,5,6-tetrahydropyrido[2,3-b][1,5]diazocin-4(1H)-one | 313.3 | |
| 103 | 5-cyclopropyl-1-(5-phenyloxazole-4-carbonyl)-2,3,5,6-tetrahydropyrido[2,3-b][1,5]diazocin-4(1H)-one | 389.4 | 2 |
| 104 | 5-cyclopropyl-1-(5-methylisoxazole-3-carbonyl)-2,3,5,6-tetrahydropyrido[2,3-b][1,5]diazocin-4(1H)-one | 327.3 | 4 |
| 105 | 5-cyclopropyl-1-(1,3-dimethyl-1H-pyrazole-5-carbonyl)-2,3,5,6-tetrahydropyrido[2,3-b][1,5]diazocin-4(1H)-one | 340.4 | 3 |
| 106 | 5-cyclopropyl-1-(3,5-dimethylisoxazole-4-carbonyl)-2,3,5,6-tetrahydropyrido[2,3-b][1,5]diazocin-4(1H)-one | 341.4 | 1 |
| 107 | 5-cyclopropyl-1-(pyrazine-2-carbonyl)-2,3,5,6-tetrahydropyrido[2,3-b][1,5]diazocin-4(1H)-one | 324.3 | 2 |
| 108 | 5-cyclopropyl-8-(difluoromethoxy)-2,3,5,6-tetrahydrobenzo[b][1,5]diazocin-4(1H)-one | 283.3 | 2 |
| 109 | (R)-5-cyclopropyl-1-(3-(3-fluorophenoxy)-2-hydroxypropyl)-8-methoxy-2,3,5,6-tetrahydrobenzo[b][1,5]diazocin-4(1H)-one | 415.5 | 3 |
| 110 | (S)-5-cyclopropyl-1-(3-(3-fluorophenoxy)-2-hydroxypropyl)-8-methoxy-2,3,5,6-tetrahydrobenzo[b][1,5]diazocin-4(1H)-one | 415.5 | 1 |
| 111 | 5-cyclopropyl-8-(difluoromethoxy)-1-(isoxazole-5-carbonyl)-2,3,5,6-tetrahydrobenzo[b][1,5]diazocin-4(1H)-one | 378.3 | 1 |
| 112 | 5-cyclopropyl-8-(difluoromethoxy)-1-(5-phenyloxazole-4-carbonyl)-2,3,5,6-tetrahydrobenzo[b][1,5]diazocin-4(1H)-one | 454.4 | 1 |
| 113 | 5-cyclopropyl-8-(difluoromethoxy)-1-(5-methylisoxazole-3-carbonyl)-2,3,5,6-tetrahydrobenzo[b][1,5]diazocin-4(1H)-one | 392.4 | 1 |
| 114 | 5-cyclopropyl-8-(difluoromethoxy)-1-(1,3-dimethyl-1H-pyrazole-5-carbonyl)-2,3,5,6-tetrahydrobenzo[b][1,5]diazocin-4(1H)-one | 405.4 | 1 |

| n° | NAME | Analytical data: HPLC-MS (M + H) | Insulin secretion (Min6 cell) Range 1 to 5 |
|---|---|---|---|
| 115 | 5-cyclopropyl-8-(difluoromethoxy)-1-(3,5-dimethylisoxazole-4-carbonyl)-2,3,5,6-tetrahydrobenzo[b][1,5]diazocin-4(1H)-one | 406.4 | 1 |
| 116 | 5-cyclopropyl-8-(difluoromethoxy)-1-(pyrazine-2-carbonyl)-2,3,5,6-tetrahydrobenzo[b][1,5]diazocin-4(1H)-one | 389.4 | 2 |
| 117 | (R)-5-cyclopropyl-8-(difluoromethoxy)-1-(3-(3-fluorophenoxy)-2-hydroxypropyl)-2,3,5,6-tetrahydrobenzo[b][1,5]diazocin-4(1H)-one | 451.5 | 1 |
| 118 | (S)-5-cyclopropyl-8-(difluoromethoxy)-1-(3-(3-fluorophenoxy)-2-hydroxypropyl)-2,3,5,6-tetrahydrobenzo[b][1,5]diazocin-4(1H)-one | 451.5 | 2 |
| 119 | (R)-1-(3-(4-chlorophenoxy)-2-hydroxypropyl)-5-cyclopropyl-8-(difluoromethoxy)-2,3,5,6-tetrahydrobenzo[b][1,5]diazocin-4(1H)-one | 467.6 | 3 |
| 120 | (S)-1-(3-(4-chlorophenoxy)-2-hydroxypropyl)-5-cyclopropyl-8-(difluoromethoxy)-2,3,5,6-tetrahydrobenzo[b][1,5]diazocin-4(1H)-one | 467.9 | 1 |
| 121 | 5-cyclopropyl-8-fluoro-1-(2-methoxyacetyl)-2,3,5,6-tetrahydrobenzo[b][1,5]diazocin-4(1H)-one | 307.3 | 1 |
| 122 | 5-cyclopropyl-8-fluoro-1-(2-phenoxyacetyl)-2,3,5,6-tetrahydrobenzo[b][1,5]diazocin-4(1H)-one | 369.4 | 1 |
| 123 | 5-cyclopropyl-8-fluoro-1-(furan-2-carbonyl)-2,3,5,6-tetrahydrobenzo[b][1,5]diazocin-4(1H)-one | 329.3 | 1 |
| 124 | 5-cyclopropyl-8-(difluoromethoxy)-2,3,5,6-tetrahydrobenzo[b][1,5]diazocin-4(1H)-one | 283.3 | 1 |
| 125 | 11-cyclopropyl-7-((1-methyl-1H-imidazol-4-yl)sulfonyl)-2,3,8,9,11,12-hexahydro-[1,4]dioxino[2',3':3,4]benzo[1,2-b][1,5]diazocin-10(7H)-one | 419.5 | 1 |
| 126 | (R)-7-(3-(4-chlorophenoxy)-2-hydroxypropyl)-11-cyclopropyl-2,3,8,9,11,12-hexahydro-[1,4]dioxino[2',3':3,4]benzo[1,2-b][1,5]diazocin-10(7H)-one | 459.9 | 2 |
| 127 | 5-cyclopropyl-7-(difluoromethoxy)-8-methoxy-2,3,5,6-tetrahydrobenzo[b][1,5]diazocin-4(1H)-one | 313.3 | 1 |
| 128 | 11-cyclopropyl-7-(pyrazine-2-carbonyl)-2,3,8,9,11,12-hexahydro-[1,4]dioxino[2',3':3,4]benzo[1,2-b][1,5]diazocin-10(7H)-one | 381.4 | 1 |
| 129 | 5-cyclopropyl-7-(difluoromethoxy)-8-methoxy-1-(pyrazine-2-carbonyl)-2,3,5,6-tetrahydrobenzo[b][1,5]diazocin-4(1H)-one | 419.4 | 2 |
| 130 | 5-cyclopropyl-8-fluoro-1-(pyrazine-2-carbonyl)-2,3,5,6-tetrahydrobenzo[b][1,5]diazocin-4(1H)-one | 341.4 | 1 |
| 131 | 8-chloro-5-cyclopropyl-1-picolinoyl-2,3,5,6-tetrahydrobenzo[b][1,5]diazocin-4(1H)-one | 356.8 | 1 |
| 132 | 11-cyclopropyl-7-picolinoyl-2,3,8,9,11,12-hexahydro-[1,4]dioxino[2',3':3,4]benzo[1,2-b][1,5]diazocin-10(7H)-one | 380.4 | 1 |
| 133 | 8-chloro-5-cyclopropyl-1-(pyrazine-2-carbonyl)-2,3,5,6-tetrahydrobenzo[b][1,5]diazocin-4(1H)-one | 357.8 | 2 |
| 134 | (R)-1-(3-(4-chlorophenoxy)-2-hydroxypropyl)-5-cyclopropyl-7-(difluoromethoxy)-8-methoxy-2,3,5,6-tetrahydrobenzo[b][1,5]diazocin-4(1H)-one | 497.9 | 1 |
| 135 | (R)-8-chloro-1-(3-(4-chlorophenoxy)-2-hydroxypropyl)-5-cyclopropyl-2,3,5,6-tetrahydrobenzo[b][1,5]diazocin-4(1H)-one | 436.3 | 1 |
| 136 | (R)-5-cyclopropyl-8-fluoro-1-(2-hydroxy-3-(4-(methylsulfonyl)phenoxy)propyl)-2,3,5,6-tetrahydrobenzo[b][1,5]diazocin-4(1H)-one | 463.5 | 1 |
| 137 | (R)-8-chloro-5-cyclopropyl-1-(2-hydroxy-3-(4-(methylsulfonyl)phenoxy)propyl)-2,3,5,6-tetrahydrobenzo[b][1,5]diazocin-4(1H)-one | 480.0 | 2 |
| 138 | 11-cyclopropyl-7-(3-methylisoxazole-5-carbonyl)-2,3,8,9,11,12-hexahydro-[1,4]dioxino[2',3':3,4]benzo[1,2-b][1,5]diazocin-10(7H)-one | 384.4 | 1 |
| 139 | 8-chloro-5-cyclopropyl-1-(3-methylisoxazole-5-carbonyl)-2,3,5,6-tetrahydrobenzo[b][1,5]diazocin-4(1H)-one | 360.8 | 1 |
| 140 | 5-cyclopropyl-7-(difluoromethoxy)-8-methoxy-1-(3-methylisoxazole-5-carbonyl)-2,3,5,6-tetrahydrobenzo[b][1,5]diazocin-4(1H)-one | 422.4 | 3 |
| 141 | 5-cyclopropyl-8-methoxy-1-(3-methylisoxazole-5-carbonyl)-2,3,5,6-tetrahydrobenzo[b][1,5]diazocin-4(1H)-one | 356.4 | 4 |

-continued

| n° | NAME | Analytical data: HPLC-MS (M + H) | Insulin secretion (Min6 cell) Range 1 to 5 |
|---|---|---|---|
| 142 | 5-cyclopropyl-8-(difluoromethoxy)-1-(3-methylisoxazole-5-carbonyl)-2,3,5,6-tetrahydrobenzo[b][1,5]diazocin-4(1H)-one | 392.4 | 4 |
| 143 | 8-chloro-5-cyclopropyl-1-(2-(4-(difluoromethoxy)phenyl)-2-oxoethyl)-2,3,5,6-tetrahydrobenzo[b][1,5]diazocin-4(1H)-one | 435.9 | 2 |
| 144 | 11-cyclopropyl-7-(2-(4-(difluoromethoxy)phenyl)-2-oxoethyl)-2,3,8,9,11,12-hexahydro-[1,4]dioxino[2',3':3,4]benzo[1,2-b][1,5]diazocin-10(7H)-one | 459.5 | 1 |
| 145 | 1-(4-chlorophenyl)-2-(5-cyclopropyl-8-fluoro-3,4,5,6-tetrahydrobenzo[b][1,5]diazocin-1(2H)-yl)ethanol | 375.9 | 3 |
| 146 | (S)-11-cyclopropyl-7-(2-hydroxypropyl)-2,3,8,9,11,12-hexahydro-[1,4]dioxino[2',3':3,4]benzo[1,2-b][1,5]diazocin-10(7H)-one | 333.4 | 5 |
| 147 | (S)-8-chloro-5-cyclopropyl-1-(2-hydroxypropyl)-2,3,5,6-tetrahydrobenzo[b][1,5]diazocin-4(1H)-one | 309.8 | 2 |
| 148 | 8-chloro-5-cyclopropyl-1-(2-(4-(difluoromethoxy)phenyl)-2-hydroxyethyl)-2,3,5,6-tetrahydrobenzo[b][1,5]diazocin-4(1H)-one | 437.9 | 1 |
| 149 | 11-cyclopropyl-7-(2-(4-(difluoromethoxy)phenyl)-2-hydroxyethyl)-2,3,8,9,11,12-hexahydro-[1,4]dioxino[2',3':3,4]benzo[1,2-b][1,5]diazocin-10(7H)-one | 461.5 | 3 |
| 150 | 5-(cyclopropylmethyl)-1-(2-(4-fluorophenyl)acetyl)-2,3,5,6-tetrahydropyrido[2,3-b][1,5]diazocin-4(1H)-one | 368.4 | 4 |
| 151 | 5-(cyclopropylmethyl)-1-(3-methylisoxazole-5-carbonyl)-2,3,5,6-tetrahydropyrido[2,3-b][1,5]diazocin-4(1H)-one | 341.4 | 1 |
| 152 | 5-(cyclopropylmethyl)-1-(pyrazine-2-carbonyl)-2,3,5,6-tetrahydropyrido[2,3-b][1,5]diazocin-4(1H)-one | 338.4 | 3 |
| 153 | 5-(cyclopropylmethyl)-1-nicotinoyl-2,3,5,6-tetrahydropyrido[2,3-b][1,5]diazocin-4(1H)-one | 337.4 | 3 |
| 154 | 5-cyclopentyl-8-fluoro-1-(2-hydroxy-3,3-dimethylbutyl)-2,3,5,6-tetrahydrobenzo[b][1,5]diazocin-4(1H)-one | 364.5 | 1 |
| 155 | ethyl 2-(4-oxo-1,2,3,4-tetrahydrobenzo[b][1,5]diazocin-5(6H)-yl)acetate | 264.3 | 1 |
| 156 | 1-(isoxazole-5-carbonyl)-8-methoxy-5-(3-methylbut-2-enyl)-2,3,5,6-tetrahydrobenzo[b][1,5]diazocin-4(1H)-one | 371.4 | 1 |
| 157 | 5-benzyl-1-(isoxazole-5-carbonyl)-2,3,5,6-tetrahydrobenzo[b][1,5]diazocin-4(1H)-one | 363.4 | 1 |
| 158 | 1-(isoxazole-5-carbonyl)-5-(pent-2-ynyl)-2,3,5,6-tetrahydrobenzo[b][1,5]diazocin-4(1H)-one | 339.4 | 1 |
| 159 | 9-(cyclopropylmethyl)-5-(isoxazol-5-ylcarbonyl)-6,7,9,10-tetrahydro[1,3]dioxolo[4,5-i][1,5]benzodiazocin-8(5H)-one | 371.4 | 1 |
| 160 | 1-(cyclobutanecarbonyl)-5-cyclopropyl-8-methoxy-2,3,5,6-tetrahydrobenzo[b][1,5]diazocin-4(1H)-one | 330.4 | 1 |
| 161 | 9-cyclopentyl-6,7,9,10-tetrahydro[1,3]dioxolo[4,5-i][1,5]benzodiazocin-8(5H)-one | 290.3 | 1 |
| 162 | 5-(3-tert-butoxy-2-hydroxypropyl)-9-cyclopropyl-6,7,9,10-tetrahydro[1,3]dioxolo[4,5-i][1,5]benzodiazocin-8(5H)-one | 392.5 | 1 |
| 163 | 5-ethyl-1-(2-hydroxypropyl)-2,3,5,6-tetrahydrobenzo[b][1,5]diazocin-4(1H)-one | 264.3 | 1 |
| 164 | 5-[3-(allyloxy)-2-hydroxypropyl]-9-ethyl-6,7,9,10-tetrahydro[1,3]dioxolo[4,5-i][1,5]benzodiazocin-8(5H)-one | 364.4 | 1 |
| 165 | 9-ethyl-5-(2-hydroxy-3-phenylpropyl)-6,7,9,10-tetrahydro[1,3]dioxolo[4,5-i][1,5]benzodiazocin-8(5H)-one | 384.5 | 1 |
| 166 | 5-ethyl-8-fluoro-1-(2-hydroxy-3,3-dimethylbutyl)-2,3,5,6-tetrahydrobenzo[b][1,5]diazocin-4(1H)-one | 324.4 | 1 |
| 167 | 7-(allyloxy)-5-ethyl-1-(2-hydroxy-3-phenoxypropyl)-8-methoxy-2,3,5,6-tetrahydrobenzo[b][1,5]diazocin-4(1H)-one | 442.5 | 2 |
| 168 | (R)-1-(3-(benzyloxy)-2-hydroxypropyl)-5-cyclopentyl-8-fluoro-2,3,5,6-tetrahydrobenzo[b][1,5]diazocin-4(1H)-one | 427.5 | 4 |
| 169 | 7-(allyloxy)-5-(cyclopropylmethyl)-1-(isoxazole-5-carbonyl)-8-methoxy-2,3,5,6-tetrahydrobenzo[b][1,5]diazocin-4(1H)-one | 412.5 | 4 |

Example 9

Pharmaceutical Composition

As a specific embodiment of an oral composition of a compound of the present composition, 50 mg of any of the compounds listed in the Table above is formulated with finely divided lactose to provide a total amount of 500 mg to fill a size O hard gelatin capsule.

The invention claimed is:
1. A compound of formula (I):

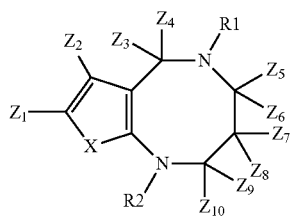

formula I wherein:
$R^1$ represents:
- a cyclopropylmethyl;
- a saturated or unsaturated carbocycle, said carbocycle being a monocyclic or bicyclic hydrocarbon ring system containing from 3 to 10 ring carbon atoms;
- a saturated or unsaturated heterocycle, said heterocycle being heteroaryl or heterocycloalkyl, said heteroaryl being an aromatic group containing 5 to 10 ring carbon atoms in which one or more ring atoms carbons are replaced by oxygen, nitrogen or sulfur and said heterocycloalkyl being a non-aromatic saturated monocyclic or bicyclic ring system containing 3 to 14 carbon atoms in which one or more ring atoms carbons are replaced by oxygen, nitrogen or sulfur;
a substituted saturated or unsaturated carbocycle, said carbocycle being a monocyclic or bicyclic hydrocarbon ring system containing from 3 to 10 ring carbon atoms, wherein the substituent is selected from the group consisting of halogen, hydroxyl, alkoxy, alkoxycarbonyl and amino group;
- a substituted saturated or unsaturated heterocycle, said heterocycle being heteroaryl or heterocycloalkyl, said heteroaryl being an aromatic group containing 5 to 10 ring carbon atoms in which one or more ring atoms carbons are replaced by oxygen, nitrogen or sulfur and said heterocycloalkyl being a non-aromatic saturated monocyclic or bicyclic ring system containing 3 to 14 carbon atoms in which one or more ring atoms carbons are replaced by oxygen, nitrogen or sulfur, wherein the substituent is selected from the group consisting of halogen, hydroxyl, alkoxy, alkoxycarbonyl, and amino group;
$R^2$ represents
- an alkyl;
- an alkenyl;
- an alkynyl;
- a saturated or unsaturated carbocycle, said carbocycle being a monocyclic or bicyclic hydrocarbon ring system containing from 3 to 10 ring carbon atoms;
- a saturated or unsaturated heterocycle, said heterocycle being heteroaryl or heterocycloalkyl, said heteroaryl being an aromatic group containing 5 to 10 ring carbon atoms in which one or more ring atoms carbons are replaced by oxygen, nitrogen or sulfur and said heterocycloalkyl being non-aromatic saturated monocyclic or bicyclic ring system containing 3 to 14 carbon atoms in which one or more ring atoms carbons are replaced by oxygen, nitrogen or sulfur as defined above;
—CO-alkyl, —CO-alkynyl, —CO-carbocycle or heterocycle, wherein the carbocycle or heterocycle is as previously defined;
—$SO_2$-alkyl, —$SO_2$-alkynyl, —$SO_2$-carbocycle or heterocycle, wherein the carbocycle or heterocycle is as previously defined;
a substituted carbocycle or heterocycle, wherein the carbocycle or heterocycle is as previously defined;
a substituted alkyl, alkenyl, alkynyl, saturated or unsaturated carbocycle, a saturated or unsaturated heterocycle, wherein the carbocycle or heterocycle is as previously defined —CO-alkyl, —CO-alkynyl, —CO -carbocycle or heterocycle, wherein the carbocycle or heterocycle is as previously defined, —$SO_2$-alkyl, —$SO_2$-alkynyl, —$SO_2$-carbocycle or heterocycle, wherein the carbocycle or heterocycle is as previously defined, wherein the substituent is selected from the group consisting of halogen, hydroxyl, alkoxy, alkoxycarbonyl, and amino group;
X represents —$C(Z^{11})$=$C(Z^{12})$—,
$Z^1$ and $Z^2$ represent independently H, halogen atom, alkyl, alkoxy, alkenyl, alkynyl, a saturated or unsaturated carbocycle, said carbocycle being a monocyclic or bicyclic hydrocarbon ring system containing from 3 to 10 ring carbon atoms or a saturated or unsaturated heterocycle, said heterocycle being heteroaryl or heterocycloalkyl, said heteroaryl being an aromatic group containing 5 to 10 ring carbon atoms in which one or more ring atoms carbons are replaced by oxygen, nitrogen or sulfur and said heterocycloalkyl being non-aromatic saturated monocyclic or bicyclic ring system containing 3 to 14 carbon atoms in which one or more ring atoms carbons are replaced by oxygen, nitrogen or sulfur, a substituted alkyl, alkoxy, alkenyl, alkynyl, carbocycle or heterocycle, a substituted carbocycle or heterocycle wherein the carbocycle or heterocycle is as previously defined and wherein the substituent is selected from the group consisting of halogen, hydroxyl, alkoxy, alkoxycarbonyl, and amino group;
$Z^3$, $Z^4$, $Z^7$, $Z^8$, $Z^9$, $Z^{10}$, $Z^{11}$ and $Z^{12}$ represent independently H, halogen atom, alkyl, alkenyl, cycloalkene, alkynyl, aryl, alkylaryl, arylalkyl, a substituted alkyl, alkenyl, alkynyl, cycloalkenyl, aryl, alkylaryl, arylalkyl wherein the substituent is selected from the group consisting of halogen, hydroxyl, alkoxy, alkoxycarbonyl, and amino group or
$Z^2$ and $Z^1$, $Z^1$ and $Z^{11}$, and/or $Z^{11}$ and $Z^{12}$ form together a saturated or unsaturated carbocycle, said carbocycle being a monocyclic or bicyclic hydrocarbon ring system containing from 3 to 10 ring carbon atoms or a saturated or unsaturated heterocycle, said heteroaryl or heterocycloalkyl, said heteroaryl being an aromatic group containing 5 to 10 ring carbon atoms in which one or more ring atoms carbons are replaced by oxygen, nitrogen or sulfur and said heterocycloalkyl being non-aromatic saturated monocyclic or bicyclic ring system containing 3 to 14 carbon atoms in which one or more ring atoms carbons are replaced by oxygen, nitrogen or sulfur, a substituted carbocycle or heterocycle, a substituted carbocycle or heterocycle wherein the carbocycle or heterocycle is as previously defined and the substituent is selected from the group consisting of halogen, hydroxyl, alkoxy, alkoxycarbonyl, and amino group;

$Z^5$ and $Z^6$ together represent =O, and wherein:

when X represents —CH=CCl—, $Z^1$, $Z^2$, $Z^5$, $Z^6$, $Z^7$, $Z^8$, $Z^9$, $Z^{10}$ each represent H; $Z^3$ and $Z^4$ represent H for one and phenyl for the other, then $R^1$ and $R^2$ does not represent respectively phenyl and methyl;

or a stereoisomer, mixture of stereoisomer or a pharmaceutically acceptable salt thereof.

2. A compound according to claim 1, characterized in that $R^1$ represents cycloalkyl, cycloalkenyl or aryl.

3. A compound according to claim 1, characterized in that $R^2$ represents alkyl, alkenyl, alkynyl, cycloalkyl, cycloalkenyl, or aryl.

4. A compound according to claim 1, characterized in that $R^2$ represents an alkyl, a —CO-alkyl, a —CO-alkynyl, a —CO-carbocycle or a —CO-heterocycle.

5. A compound according to claim 1, characterized in that $Z^3$, $Z^4$, $Z^7$, $Z^8$, $Z^9$ and $Z^{10}$ represent H.

6. A compound according to claim 1, characterized in that $Z^1$ and $Z^2$ represent independently H, halogen atom, alkoxy and alkenyloxy, optionally substituted by one or more halogen atom, or $Z^1$ and $Z^2$ form together a heterocycloalkyl.

7. A compound according to claim 1, characterized in that it corresponds to formula II:

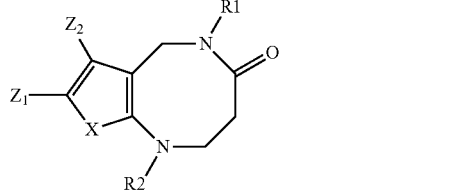

formula II wherein:

X is —CH=CH—, $Z^2$ is H or alkoxy, $R^1$ is cycloalkyl, $Z^1$ is halogen, alkyl or alkoxy, and $R^2$ is an alkyl substituted with a hydroxyl group, a heterocyclecarbonyl or a carbocyclecarbonyl.

8. A compound according to claim 1, characterized in that it corresponds to formula II:

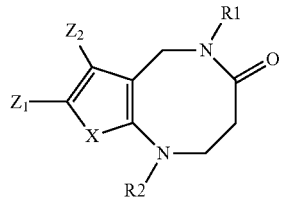

formula II wherein:

X is —CH=CH—, $R^1$ is cyclopropylmethyl or a cycloalkyl, $Z^1$ and $Z^2$ form together a carbocycle or an heterocycle, and $R^2$ is a heterocyclecarbonyl or an unsubstituted or substituted hydroxyalkyl.

9. A compound according to claim 1, characterized in that it corresponds to formula II:

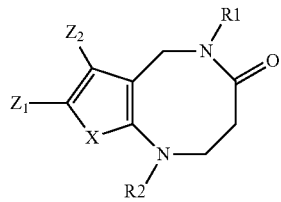

formula II wherein:

X is —CH=CH—, $Z^2$ is H, $R^1$ is a cycloalkyl, $Z^1$ is halogen, or methoxy, and $R^2$ is an alkyl substituted with a hydroxyl group.

10. A compound according to claim 1, characterized in that it corresponds to formula II:

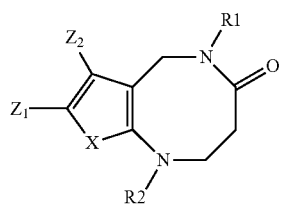

formula II wherein:

X is —CH=CH—, $Z^2$ is alkoxy, $R^1$ is cyclopropylmethyl, $Z^1$ is halogen or methoxy, and $R^2$ is an alkyl substituted with a hydroxyl group or a heterocyclecarbonyl.

11. A compound according to claim 1, characterized in that it corresponds to formula II:

formula II wherein:

X is —CH=CH—, $Z^2$ is H, $R^1$ is cycloalkyl, $Z^1$ is difluoromethoxy, $R^2$ is a heterocyclecarbonyl.

12. A compound according to claim 1, characterized in that it corresponds to formula II:

*formula II* wherein:
X is —CH=CH—,
$Z^2$ is difluoromethoxy,
$R^1$ is cycloalkyl, $Z^1$ is methoxy, and
$R^2$ is a heterocyclecarbonyl.

13. A compound to according to claim 1, characterized in that it corresponds to formula II:

*formula II* wherein:
X is —CH=CH—,
$Z^2$ is H,
$R^1$ is an aryl or an arylalkyl
$Z^1$ is H or alkoxy and
$R^2$ is a heterocyclecarbonyl.

14. A compound according to claim 1, characterized in that it corresponds to formula II:

*formula II* wherein:
X is —CH=CH—,
$Z^2$ is H,
$R^1$ is cycloalkyl,
$Z^1$ is halogen and
$R^2$ is a heterocyclecarbonyl.

15. A compound according to claim 1, characterized in that it corresponds to formula II:

*formula II* wherein:
X is —CH=CH—,
$R^1$ is a cycloalkyl,
$Z^1$ and $Z^2$ represent H, and
$R^2$ represents unsubstituted or substituted 2-hydroxyalkyl.

16. A compound according to claim 1, characterized in that it corresponds to formula II:

*formula II* wherein:
X is —CH=CH—,
$R^1$ is cycloalkyl,
$Z^1$ and $Z^2$ form together a carbocycle or an heterocycle, and
$R^2$ is a heterocyclecarbonyl.

17. A compound according to claim 1, characterized in that it corresponds to formula II:

*formula II* wherein:
X is —CH=CH—,
$R^1$ is cycloalkyl, $Z^1$ and $Z^2$ form together a carbocycle or an heterocycle, and
$R^2$ is H.

18. A compound according to claim 1, characterized in that it corresponds to formula II:

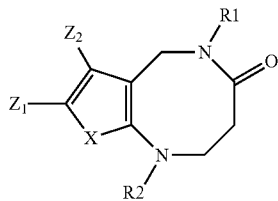

formula II wherein:
X is —CH=CH—,
$R^1$ is cycloalkyl, $Z^1$ and $Z^2$ form together a carbocycle or an heterocycle, and
$R^2$ is an unsubstituted or substituted 2-hydroxypropyl.

19. A compound according to claim 1, characterized in that it is chosen from:
- 5-cyclopropyl-1-(2-hydroxy-3-phenoxypropyl)-8-methoxy-2,3,5,6-tetrahydrobenzo[b][1,5]diazocin-4(1H)-one,
- 1-(4-chlorophenethyl)-5-cyclopropyl-8-methoxy-2,3,5,6-tetrahydrobenzo[b][1,5]diazocin-4(1H)-one,
- 5-cyclopropyl-8-methoxy-1-(5-methylisoxazole-3-carbonyl)-2,3,5,6-tetrahydrobenzo[b][1,5]diazocin-4(1H)-one,
- 5-cyclopropyl-1-(2-(4-fluorophenyl)-2-oxoethyl)-8-methoxy-2,3,5,6-tetrahydrobenzo[b][1,5]diazocin-4(1H)-one,
- 5-cyclopropyl-1-(2-(4-fluorophenyl)-2-hydroxyethyl)-8-methoxy-2,3,5,6-tetrahydrobenzo[b][1,5]diazocin-4(1H)-one,
- 5-cyclopropyl-8-methoxy-1-(2-oxo-2-phenylethyl)-2,3,5,6-tetrahydrobenzo[b][1,5]diazocin-4(1H)-one,
- 5-cyclopropyl-1-(2-(2,5-dimethoxyphenyl)-2-oxoethyl)-8-methoxy-2,3,5,6-tetrahydrobenzo[b][1,5]diazocin-4(1H)-one,
- 5-cyclopropyl-8-methoxy-1-(2-(2-methoxyphenyl)-2-oxoethyl)-2,3,5,6-tetrahydrobenzo[b][1,5]diazocin-4(1H)-one,
- 1-(2-(4-chlorophenyl)-2-oxoethyl)-5-cyclopropyl-8-methoxy-2,3,5,6-tetrahydrobenzo[b][1,5]diazocin-4(1H)-one,
- 5-cyclopropyl-1-(2-(2,3-dihydrobenzo[b][1,4]dioxin-6-yl)-2-oxoethyl)-8-methoxy-2,3,5,6-tetrahydrobenzo[b][1,5]diazocin-4(1H)-one,
- 5-cyclopropyl-8-methoxy-1-(2-oxo-2-(4-(pyrrolidin-1-yl)phenyl)ethyl)-2,3,5,6-tetrahydrobenzo[b][1,5]diazocin-4(1H)-one,
- 5-cyclopropyl-1-(2-hydroxy-2-phenylethyl)-8-methoxy-2,3,5,6-tetrahydrobenzo[b][1,5]diazocin-4(1H)-one,
- (R)-1-(3-(benzyloxy)-2-hydroxypropyl)-5-cyclopropyl-8-methoxy-2,3,5,6-tetrahydrobenzo[b][1,5]diazocin-4(1H)-one,
- (R)-1-(3-(benzyloxy)-2-hydroxypropyl)-5-cyclopropyl-8-fluoro-2,3,5,6-tetrahydrobenzo[b][1,5]diazocin-4(1H)-one,
- 5-cyclopropyl-8-methoxy-1-(2-(3-methoxyphenyl)-2-oxoethyl)-2,3,5,6-tetrahydrobenzo[b][1,5]diazocin-4(1H)-one,
- 5-cyclopropyl-8-methoxy-1-(2-(4-methoxyphenyl)-2-oxoethyl)-2,3,5,6-tetrahydrobenzo[b][1,5]diazocin-4(1H)-one,
- 5-cyclopropyl-1-(2-(3-fluorophenyl)-2-oxoethyl)-8-methoxy-2,3,5,6-tetrahydrobenzo[b][1,5]diazocin-4(1H)-one,
- 5-cyclopropyl-8-methoxy-1-(2-oxo-2-(4-(trifluoromethoxy)phenyl)ethyl)-2,3,5,6-tetrahydrobenzo[b][1,5]diazocin-4(1H)-one,
- 5-cyclopropyl-1-(2-(3,4-difluorophenyl)-2-oxoethyl)-8-methoxy-2,3,5,6-tetrahydrobenzo[b][1,5]diazocin-4(1H)-one,
- 5-cyclopropyl-1-(2-(2,5-dimethoxyphenyl)-2-hydroxyethyl)-8-methoxy-2,3,5,6-tetrahydrobenzo[b][1,5]diazocin-4(1H)-one,
- 5-cyclopropyl-1-(2-hydroxy-2-(2-methoxyphenyl)ethyl)-8-methoxy-2,3,5,6-tetrahydrobenzo[b][1,5]diazocin-4(1H)-one,
- 1-(2-(4-chlorophenyl)-2-hydroxyethyl)-5-cyclopropyl-8-methoxy-2,3,5,6-tetrahydrobenzo[b][1,5]diazocin-4(1H)-one,
- 5-cyclopropyl-1-(2-hydroxy-2-(4-(pyrrolidin-1-yl)phenyl)ethyl)-8-methoxy-2,3,5,6-tetrahydrobenzo[b][1,5]diazocin-4(1H)-one,
- 5-cyclopropyl-1-(2-(2,3-dihydrobenzo[b][1,4]dioxin-6-yl)-2-hydroxyethyl)-8-methoxy-2,3,5,6-tetrahydrobenzo[b][1,5]diazocin-4(1H)-one
- 5-cyclopropyl-1-(2-hydroxy-2-(3-methoxyphenyl)ethyl)-8-methoxy-2,3,5,6-tetrahydrobenzo[b][1,5]diazocin-4(1H)-one,
- 5-cyclopropyl-1-(2-(3-fluorophenyl)-2-hydroxyethyl)-8-methoxy-2,3,5,6-tetrahydrobenzo[b][1,5]diazocin-4(1H)-one,
- 5-cyclopropyl-1-(2-hydroxy-2-(4-methoxyphenyl)ethyl)-8-methoxy-2,3,5,6-tetrahydrobenzo[b][1,5]diazocin-4(1H)-one,
- 5-cyclopropyl-1-(2-hydroxy-2-(4-trifluoromethoxy)phenyl)ethyl)-8-methoxy-2,3,5,6-tetrahydrobenzo[b][1,5]diazocin-4(1H)-one,
- 5-cyclopropyl-1-(2-(3,4-difluorophenyl)-2-hydroxyethyl)-8-methoxy-2,3,5,6-tetrahydrobenzo[b][1,5]diazocin-4(1H)-one,
- 5-cyclopropyl-8-fluoro-1-(2-oxo-2-phenylethyl)-2,3,5,6-tetrahydrobenzo[b][1,5]diazocin-4(1H)-one,
- 5-cyclopropyl-8-fluoro-1-(2-(2-methoxyphenyl)-2-oxoethyl)-2,3,5,6-tetrahydrobenzo[b][1,5]diazocin-4(1H)-one,
- 5-cyclopropyl-8-fluoro-1-(2-(3-methoxyphenyl)-2-oxoethyl)-2,3,5,6-tetrahydrobenzo[b][1,5]diazocin-4(1H)-one,
- 5-cyclopropyl-8-fluoro-1-(2-(4-methoxyphenyl)-2-oxoethyl)-2,3,5,6-tetrahydrobenzo[b][1,5]diazocin-4(1H)-one,
- 5-cyclopropyl-1-(2-(2,5-dimethoxyphenyl)-2-oxoethyl)-8-fluoro-2,3,5,6-tetrahydrobenzo[b][1,5]diazocin-4(1H)-one,
- 5-cyclopropyl-8-fluoro-1-(2-(4-fluorophenyl)-2-oxoethyl)-2,3,5,6-tetrahydrobenzo[b][1,5]diazocin-4(1H)-one,
- 5-cyclopropyl-8-fluoro-1-(2-(3-fluorophenyl)-2-oxoethyl)-2,3,5,6-tetrahydrobenzo[b][1,5]diazocin-4(1H)-one,
- 5-cyclopropyl-8-fluoro-1-(2-oxo-2-(4-(trifluoromethoxy)phenyl)ethyl)-2,3,5,6-tetrahydrobenzo[b][1,5]diazocin-4(1H)-one,
- 5-cyclopropyl-1-(2-(3,4-difluorophenyl)-2-oxoethyl)-8-fluoro-2,3,5,6-tetrahydrobenzo[b][1,5]diazocin-4(1H)-one, 1-(2-(4-chlorophenyl)-2-oxoethyl)-5-cyclopropyl-8-fluoro-2,3,5,6-tetrahydrobenzo[b][1,5]diazocin-4(1H)-one, 5-cyclopropyl-1-(2-(2,5-dimethoxyphenyl)-2-hydroxyethyl)-8-fluoro-2,3,5,6-tetrahydrobenzo[b][1,5]diazocin-4(1H)-one, 5-cyclopropyl-8-fluoro-1-(2-(4-fluorophenyl)-2-hydroxyethyl)-2,3,5,6-tetrahydrobenzo[b][1,5]diazocin-4(1H)-one, 5-cyclopropyl-8-fluoro-1-(2-(3-fluorophenyl)-2-hydroxyethyl)-2,3,5,6-tetrahydrobenzo[b][1,5]diazocin-4(1H)-one, 5-cyclopropyl-8-fluoro-1-(2-hydroxy-2-(4-(trifluoromethoxy)phenyl)ethyl)-2,3,5,6-tetrahydrobenzo[b][1,5]diazocin-4(1H)-one, 5-cyclopropyl-1-(2-(3,4-difluorophenyl)-2-hydroxyethyl)-8-fluoro-2,3,5,6-tetrahydrobenzo[b][1,5]diazocin-4(1H)-one, 1-(2-(4-chlorophenyl)-2-hydroxyethyl)-5-cyclopropyl-8-fluoro-2,3,5,6-tetrahydrobenzo[b][1,5]diazocin-4(1H)-one, 5-cyclopropyl-1-(2-hydroxy-3-(4-methoxyphenoxy)propyl)-8-methoxy-2,3,5,6-tetrahydrobenzo[b][1,5]diazocin-4(1H)-one, 5-cyclopropyl-8-fluoro-1-(2-hydroxy-3-phenoxypropyl)-2,3,5,6-tetrahydrobenzo[b][1,5]diazocin-4(1H)-one, 5-cyclopropyl-8-fluoro-1-(2-hydroxy-3-(4-methoxyphenoxy)propyl)-2,3,5,6-tetrahydrobenzo[b][1,5]diazocin-4(1H)-one, 5-cyclopropyl-1-(2-(2,3-dihydrobenzo[b][1,4]dioxin-6-yl)-2-oxoethyl)-8-fluoro-2,3,5,6-tetrahydrobenzo[b][1,5]diazocin-4(1H)-one, 5-cyclopropyl-8-fluoro-1-(2-oxo-2-(4-(pyrrolidin-1-yl)phenyl)ethyl)-2,3,5,6-tetrahydrobenzo[b][1,5]diazocin-4(1H)-one, 5-cyclopropyl-8-fluoro-1-(2-hydroxy-2-(2-methoxyphenyl)ethyl)-2,3,5,6-tetrahydrobenzo[b][1,5]diazocin-4(1H)-one, 5-cyclopropyl-8-fluoro-1-(2-hydroxy-2-(3-methoxyphenyl)ethyl)-2,3,5,6-tetrahydrobenzo[b][1,5]diazocin-4(1H)-one, 5-cyclopropyl-8-fluoro-1-(2-hydroxy-2-(4-methoxyphenyl)ethyl)-2,3,5,6-tetrahydrobenzo[b][1,5]diazocin-4(1H)-one, 5-cyclopropyl-1-(2-(2,3-dihydrobenzo[b][1,4]dioxin-6-yl)-2-hydroxyethyl)-8-fluoro-2,3,5,6-tetrahydrobenzo[b][1,5]diazocin-4(1H)-one, 5-cyclopropyl-8-fluoro-1-(2-hydroxy-2-phenylethyl)-2,3,5,6-tetrahydrobenzo[b][1,5]diazocin-4(1H)-one, 2-(7-(allyloxy)-5-cyclopentyl-8-methoxy-4-oxo-3,4,5,6-tetrahydrobenzo[b][1,5]diazocin-1(2H)-yl)acetic acid, 5-cyclopropyl-8-fluoro-1-(2-hydroxy-2-(4-(pyrrolidin-1-yl)phenyl)ethyl)-2,3,5,6-tetrahydrobenzo[b][1,5]diazocin-4(1H)-one, 5-cyclopropyl-8-fluoro-1-(3-(4-fluorophenoxy)-2-hydroxypropyl)-2,3,5,6-tetrahydrobenzo[b][1,5]diazocin-4(1H)-one, (S)-1-(3-(benzyloxy)-2-hydroxypropyl)-5-cyclopropyl-8-fluoro-2,3,5,6-tetrahydrobenzo[b][1,5]diazocin-4(1H)-one, (S)-1-(3-(benzyloxy)-2-hydroxypropyl)-5-cyclopropyl-8-methoxy-2,3,5,6-tetrahydrobenzo[b][1,5]diazocin-4(1H)-one, (R)-5-cyclopropyl-1-(2,3-dihydroxypropyl)-8-methoxy-2,3,5,6-tetrahydrobenzo[b][1,5]diazocin-4(1H)-one, 5-cyclopropyl-8-fluoro-1-(4-fluorobenzoyl)-2,3,5,6-tetrahydrobenzo[b][1,5]diazocin-4(1H)-one, 5-cyclopropyl-8-fluoro-1-nicotinoyl-2,3,5,6-tetrahydrobenzo[b][1,5]diazocin-4(1H)-one, 5-cyclopropyl-8-fluoro-1-(2-(4-fluorophenyl)acetyl)-2,3,5,6-tetrahydrobenzo[b][1,5]diazocin-4(1H)-one, 1-benzyl-5-cyclopropyl-8-fluoro-2,3,5,6-tetrahydrobenzo[b][1,5]diazocin-4(1H)-one, 5-cyclopropyl-8-fluoro-1-phenethyl-2,3,5,6-tetrahydrobenzo[b][1,5]diazocin-4(1H)-one, 5-cyclopropyl-8-fluoro-1-(3-phenylpropyl)-2,3,5,6-tetrahydrobenzo[b][1,5]diazocin-4(1H)-one, 5-cyclopropyl-1-(4-fluorobenzoyl)-2,3,5,6-tetrahydropyrido[2,3-b][1,5]diazocin-4(1H)-one, 5-cyclopropyl-1-(2-(4-fluorophenyl)acetyl)-2,3,5,6-tetrahydropyrido[2,3-b][1,5]diazocin-4(1H)-one, 5-cyclopropyl-1-nicotinoyl-2,3,5,6-tetrahydropyrido[2,3-b][1,5]diazocin-4(1H)-one (R)-1-(3-(benzyloxy)-2-hydroxypropyl)-8-chloro-5-cyclopropyl-2,3,5,6-tetrahydrobenzo[b][1,5]diazocin-4(1H)-one, 8-chloro-5-cyclopropyl-1-(2-hydroxy-3-phenoxypropyl)-2,3,5,6-tetrahydrobenzo[b][1,5]diazocin-4(1H)-one, 8-chloro-1-(2-(4-chlorophenyl)-2-oxoethyl)-5-cyclopropyl-2,3,5,6-tetrahydrobenzo[b][1,5]diazocin-4(1H)-one, 8-chloro-5-cyclopropyl-1-(2-(3-fluorophenyl)-2-oxoethyl)-2,3,5,6-tetrahydrobenzo[b][1,5]diazocin-4(1H)-one, 5-cyclopropyl-1-(isoxazole-5-carbonyl)-8-methoxy-2,3,5,6-tetrahydrobenzo[b][1,5]diazocin-4(1H)-one, 8-chloro-1-(2-(4-chlorophenyl)-2-hydroxyethyl)-5-cyclopropyl-2,3,5,6-tetrahydrobenzo[b][1,5]diazocin-4(1H)-one, 8-chloro-5-cyclopropyl-1-(2-(3-fluorophenyl)-2-hydroxyethyl)-2,3,5,6-tetrahydrobenzo[b][1,5]diazocin-4(1H)-one, 7-[(2R)-3-(benzyloxy)-2-hydroxypropyl]-11-cyclopropyl-2,3,8,9,11,12-hexahydro[1,4]dioxino[2,3-h][1,5]benzodiazocin-10(7H)-one, (R)-1-(3-(4-chlorophenoxy)-2-hydroxypropyl)-5-cyclopropyl-8-methoxy-2,3,5,6-tetrahydrobenzo[b][1,5]diazocin-4(1H)-one, (S)-1-(3-(4-chlorophenoxy)-2-hydroxypropyl)-5-cyclopropyl-8-methoxy-2,3,5,6-tetrahydrobenzo[b][1,5]diazocin-4(1H)-one, 11-cyclopropyl-7-(isoxazol-5-ylcarbonyl)-2,3,8,9,11,12-hexahydro[1,4]dioxino[2,3-h][1,5]benzodiazocin-10(7H)-one, 11-cyclopropyl-7-[(5-phenyl-1,3-oxazol-4-yl)carbonyl]-2,3,8,9,11,12-hexahydro[1,4]dioxino[2,3-h][1,5]benzodiazocin-10(7H)-one, 11-cyclopropyl-7-[2-(3-fluorophenyl)-2-oxoethyl]-2,3,8,9,11,12-hexahydro[1,4]dioxino[2,3-h][1,5]benzodiazocin-10(7H)-one, 7-[2-(4-chlorophenyl)-2-oxoethyl]-11-cyclopropyl-2,3,8,9,11,12-hexahydro[1,4]dioxino[2,3-h][1,5]benzodiazocin-10(7H)-one, 11-cyclopropyl-7-(2-hydroxy-3-phenoxypropyl)-2,3,8,9,11,12-hexahydro[1,4]dioxino[2,3-h][1,5]benzodiazocin-10(7H)-one, 11-cyclopropyl-7-[2-(3-fluorophenyl)-2-hydroxyethyl]-2,3,8,9,11,12-hexahydro[1,4]dioxino[2,3-h][1,5]benzodiazocin-10(7H)-one, 7-[2-(4-chlorophenyl)-2-hydroxyethyl]-11-cyclopropyl-2,3,8,9,11,12-hexahydro[1,4]dioxino[2,3-h][1,5]benzodiazocin-10(7H)-one, 5-cyclopropyl-8-methoxy-1-(5-phenyloxazole-4-carbonyl)-2,3,5,6-tetrahydrobenzo[b][1,5]diazocin-4(1H)-one,
5-cyclopropyl-1-(1,3-dimethyl-1H-pyrazole-5-carbonyl)-8-methoxy-2,3,5,6-tetrahydrobenzo[b][1,5]diazocin-4(1H)-one,
5-cyclopropyl-1-(3,5-dimethylisoxazole-4-carbonyl)-8-methoxy-2,3,5,6-tetrahydrobenzo[b][1,5]diazocin-4(1H)-one,
5-cyclopropyl-8-methoxy-1-(pyrazine-2-carbonyl)-2,3,5,6-tetrahydrobenzo[b][1,5]diazocin-4(1H)-one,
5-cyclopropyl-1-(isoxazole-5-carbonyl)-2,3,5,6-tetrahydropyrido[2,3-b][1,5]diazocin-4(1H)-one,
5-cyclopropyl-1-(5-phenyloxazole-4-carbonyl)-2,3,5,6-tetrahydropyrido[2,3-b][1,5]diazocin-4(1H)-one,
5-cyclopropyl-1-(5-methylisoxazole-3-carbonyl)-2,3,5,6-tetrahydropyrido[2,3-b][1,5]diazocin-4(1H)-one,
5-cyclopropyl-1-(1,3-dimethyl-1H-pyrazole-5-carbonyl)-2,3,5,6-tetrahydropyrido[2,3-b][1,5]diazocin-4(1H)-one,
5-cyclopropyl-1-(3,5-dimethylisoxazole-4-carbonyl)-2,3,5,6-tetrahydropyrido[2,3-b][1,5]diazocin-4(1H)-one,
5-cyclopropyl-1-(pyrazine-2-carbonyl)-2,3,5,6-tetrahydropyrido[2,3-b][1,5]diazocin-4(1H)-one,
(R)-5-cyclopropyl-1-(3-(3-fluorophenoxy)-2-hydroxypropyl)-8-methoxy-2,3,5,6-tetrahydrobenzo[b][1,5]diazocin-4(1H)-one,
(S)-5-cyclopropyl-1-(3-(3-fluorophenoxy)-2-hydroxypropyl)-8-methoxy-2,3,5,6-tetrahydrobenzo[b][1,5]diazocin-4(1H)-one,
5-cyclopropyl-8-(difluoromethoxy)-1-(isoxazole-5-carbonyl)-2,3,5,6-tetrahydrobenzo[b][1,5]diazocin-4(1H)-one,
5-cyclopropyl-8-(difluoromethoxy)-1-(5-phenyloxazole-4-carbonyl)-2,3,5,6-tetrahydrobenzo[b][1,5]diazocin-4(1H)-one,
5-cyclopropyl-8-(difluoromethoxy)-1-(5-methylisoxazole-3-carbonyl)-2,3,5,6-tetrahydrobenzo[b][1,5]diazocin-4(1H)-one,
5-cyclopropyl-8-(difluoromethoxy)-1-(1,3-dimethyl-1H-pyrazole-5-carbonyl)-2,3,5,6-tetrahydrobenzo[b][1,5]diazocin-4(1H)-one,
5-cyclopropyl-8-(difluoromethoxy)-1-(3,5-dimethylisoxazole-4-carbonyl)-2,3,5,6-tetrahydrobenzo[b][1,5]diazocin-4(1H)-one,
5-cyclopropyl-8-(difluoromethoxy)-1-(pyrazine-2-carbonyl)-2,3,5,6-tetrahydrobenzo[b][1,5]diazocin-4(1H)-one,
(R)-5-cyclopropyl-8-(difluoromethoxy)-1-(3-(3-fluorophenoxy)-2-hydroxypropyl)-2,3,5,6-tetrahydrobenzo[b][1,5]diazocin-4(1H)-one,
(S)-5-cyclopropyl-8-(difluoromethoxy)-1-(3-(3-fluorophenoxy)-2-hydroxypropyl)-2,3,5,6-tetrahydrobenzo[b][1,5]diazocin-4(1H)-one,
(R)-1-(3-(4-chlorophenoxy)-2-hydroxypropyl)-5-cyclopropyl-8-(difluoromethoxy)-2,3,5,6-tetrahydrobenzo[b][1,5]diazocin-4(1H)-one,
(S)-1-(3-(4-chlorophenoxy)-2-hydroxypropyl)-5-cyclopropyl-8-(difluoromethoxy)-2,3,5,6-tetrahydrobenzo[b][1,5]diazocin-4(1H)-one,
5-cyclopropyl-8-fluoro-1-(2-methoxyacetyl)-2,3,5,6-tetrahydrobenzo[b][1,5]diazocin-4(1H)-one,
5-cyclopropyl-8-fluoro-1-(2-phenoxyacetyl)-2,3,5,6-tetrahydrobenzo[b][1,5]diazocin-4(1H)-one,
5-cyclopropyl-8-fluoro-1-(furan-2-carbonyl)-2,3,5,6-tetrahydrobenzo[b][1,5]diazocin-4(1H)-one,
5-cyclopropyl-8-(difluoromethoxy)-2,3,5,6-tetrahydrobenzo[b][1,5]diazocin-4(1H)-one,
11-cyclopropyl-7-((1-methyl-1H-imidazol-4-yl)sulfonyl)-2,3,8,9,11,12-hexahydro-[1,4]dioxino[2',3':3,4]benzo[1,2-b][1,5]diazocin-10(7H)-one,
(R)-7-(3-(4-chlorophenoxy)-2-hydroxypropyl)-11-cyclopropyl-2,3,8,9,11,12-hexahydro-[1,4]dioxino[2',3':3,4]benzo[1,2-b][1,5]diazocin-10(7H)-one,
5-cyclopropyl-7-(difluoromethoxy)-8-methoxy-2,3,5,6-tetrahydrobenzo[b][1,5]diazocin-4(1H)-one,
11-cyclopropyl-7-(pyrazine-2-carbonyl)-2,3,8,9,11,12-hexahydro-[1,4]dioxino[2',3':3,4]benzo[1,2-b][1,5]diazocin-10(7H)-one,
5-cyclopropyl-7-(difluoromethoxy)-8-methoxy-1-(pyrazine-2-carbonyl)-2,3,5,6-tetrahydrobenzo[b][1,5]diazocin-4(1H)-one,
5-cyclopropyl-8-fluoro-1-(pyrazine-2-carbonyl)-2,3,5,6-tetrahydrobenzo[b][1,5]diazocin-4(1H)-one,
8-chloro-5-cyclopropyl-1-picolinoyl-2,3,5,6-tetrahydrobenzo[b][1,5]diazocin-4(1H)-one,
11-cyclopropyl-7-picolinoyl-2,3,8,9,11,12-hexahydro-[1,4]dioxino[2',3'3,4]benzo[1,2-b][1,5]diazocin-1(7H)-one,
8-chloro-5-cyclopropyl-1-(pyrazine-2-carbonyl)-2,3,5,6-tetrahydrobenzo[b][1,5]diazocin-4(1H)-one,
(R)-1-(3-(4-chlorophenoxy)-2-hydroxypropyl)-5-cyclopropyl-7-(difluoromethoxy)-8-methoxy-2,3,5,6-tetrahydrobenzo[b][1,5]diazocin-4(1H)-one,
(R)-8-chloro-1-(3-(4-chlorophenoxy)-2-hydroxypropyl)-5-cyclopropyl-2,3,5,6-tetrahydrobenzo[b][1,5]diazocin-4(1H)-one,
(R)-5-cyclopropyl-8-fluoro-1-(2-hydroxy-3-(4-(methylsulfonyl)phenoxy)propyl)-2,3,5,6-tetrahydrobenzo[b][1,5]diazocin-4(1H)-one,
(R)-8-chloro-5-cyclopropyl-1-(2-hydroxy-3-(4-(methylsulfonyl)phenoxy)propyl)-2,3,5,6-tetrahydrobenzo[b][1,5]diazocin-4(1H)-one,
11-cyclopropyl-7-(3-methylisoxazole-5-carbonyl)-2,3,8,9,11,12-hexahydro-[1,4]dioxino[2',3':3,4]benzo[1,2-b][1,5]diazocin-10(7H)-one, -8-chloro-5-cyclopropyl-1-(3-methylisoxazole-5-carbonyl)-2,3,5,6-tetrahydrobenzo[b][1,5]diazocin-4(1H)-one,
5-cyclopropyl-7-(difluoromethoxy)-8-methoxy-1-(3-methylisoxazole-5-carbonyl)-2,3,5,6-tetrahydrobenzo[b][1,5]diazocin-4(1H)-one,
5-cyclopropyl-8-methoxy-1-(3-methylisoxazole-5-carbonyl)-2,3,5,6-tetrahydrobenzo[b][1,5]diazocin-4(1H)-one,
5-cyclopropyl-8-(difluoromethoxy)-1-(3-methylisoxazole-5-carbonyl)-2,3,5,6-tetrahydrobenzo[b][1,5]diazocin-4(1H)-one,
8-chloro-5-cyclopropyl-1-(2-(4-(difluoromethoxy)phenyl)-2-oxoethyl)-2,3,5,6-tetrahydrobenzo[b][1,5]diazocin-4(1H)-one,
11-cyclopropyl-7-(2-(4-(difluoromethoxy)phenyl)-2-oxoethyl)-2,3,8,9,11,12-hexahydro-[1,4]dioxino[2',3'3,4]benzo[1,2-b][1,5]diazocin-10(7H)-one,
(S)-11-cyclopropyl-7-(2-hydroxypropyl)-2,3,8,9,11,12-hexahydro-[1,4]dioxino[2',3'3,4]benzo[1,2-b][1,5]diazocin-10(7H)-one,
(S)-8-chloro-5-cyclopropyl-1-(2-hydroxypropyl)-2,3,5,6-tetrahydrobenzo[b][1,5]diazocin-4(1H)-one,
8-chloro-5-cyclopropyl-1-(2-(4-(difluoromethoxy)phenyl)-2-hydroxyethyl)-2,3,5,6-tetrahydrobenzo[b][1,5]diazocin-4(1H)-one, 11-cyclopropyl-7-(2-(4-(difluoromethoxy)phenyl)-2-hydroxyethyl)-2,3,8,9,11,12-hexahydro-[1,4]dioxino [2',3'3,4]benzo [1,2-b][1,5] diazocin-10(7H)-one, 5-(cyclopropylmethyl)-1-(2-(4-fluorophenyl)acetyl)-2,3,5,6-tetrahydropyrido [2,3-b][1,5]diazocin-4(1H)-one, 5-(cyclopropylmethyl)-1-(3-methylisoxazole-5-carbonyl)-2,3,5,6-tetrahydropyrido [2,3-b][1,5 ]diazo cin-4 (1H)-one, 5-(cyclopropylmethyl)-1-(pyrazine-2-carbonyl)-2,3,5,6-tetrahydropyrido [2,3-b] [1,5]diazocin-4(1H)-one, 5-(cyclopropylmethyl)-1-nicotinoyl-2,3,5,6-tetrahydropyrido [2,3-b][1,5 ]diazo cin -4(1H)-one, 1-(3-tert-butoxy-2-hydroxypropyl)-5-(cyclopropylmethyl)-2,3,5,6-tetrahydrobenzo[b][1,5]diazocin-4(1H)-one, 5-(cyclopropylmethyl)-1-(2-hydroxypropyl)-2,3,5,6-tetrahydrobenzo[b][1,5]diazocin-4(1H)-one, 5-(cyclopropylmethyl)-1-(2-hydroxy-3-phenoxypropyl)-2,3,5,6-tetrahydrobenzo[b][1,5]diazocin-4(1H)-one, 5-(cyclopropylmethyl)-1-(2-hydroxypentyl)-2,3,5,6-tetrahydrobenzo[b][1,5]diazocin-4(1H)-one, 5-(cyclopropylmethyl)-1-(2-hydroxy-3-(4-methoxyphenoxy)propyl)-2,3,5,6-tetrahydrobenzo[b][1,5]diazocin-4(1H)-one, 5-(cyclopropylmethyl)-1-(2-hydroxy-3-methoxypropyl)-2,3,5,6-tetrahydrobenzo[b][1,5]diazocin-4(1H)-one, 5-(cyclopropylmethyl)-1-(2-hydroxy-3-phenylpropyl)-2,3,5,6-tetrahydrobenzo[b][1,5]diazocin-4(1H)-one, 5-(cyclopropylmethyl)-1-(3,3,3-trifluoro-2-hydroxypropyl)-2,3,5,6-tetrahydrobenzo[b][1,5]diazocin-4(1H)-one, 5-cyclopentyl-8-fluoro-1-(2-hydroxy-3,3-dimethylbutyl)-2,3,5,6-tetrahydrobenzo[b][1,5]diazocin-4(1H)-one, 9-(cyclopropylmethyl)-5-(isoxazol-5-ylcarbonyl)-6,7,9,10-tetrahydro[1,3]dioxolo[4,5-i][1,5]benzodiazocin-8(5H)-one, 1-(cyclobutanecarbonyl)-5-cyclopropyl-8-methoxy-2,3,5,6-tetrahydrobenzo[b][1,5]diazocin-4(1H)-one, 5-(3-tert-butoxy-2-hydroxypropyl)-9-cyclopropyl-6,7,9,10-tetrahydro[1,3]dioxolo[4,5-i][1,5]benzodiazocin-8(5H)-one, 5-cyclopentyl-8-fluoro-1-(2-hydroxy-3,3-dimethylbutyl)-2,3,5,6-tetrahydrobenzo[b][1,5]diazocin-4(1H)-one, ethyl 2-(4-oxo-1,2,3,4-tetrahydrobenzo[b][1,5]diazocin-5(6H)-yl)acetate, 1-(isoxazole-5-carbonyl)-8-methoxy-5-(3-methylbut-2-enyl)-2,3,5,6-tetrahydrobenzo[b][1,5]diazocin-4(1H)-one, 5-benzyl-1-(isoxazole-5-carbonyl)-2,3,5,6-tetrahydrobenzo[b][1,5]diazocin-4(1H)-one, 1-(isoxazole-5-carbonyl)-5-(pent-2-ynyl)-2,3,5,6-tetrahydrobenzo[b][1,5]diazocin -4(1H)-one, 9-(cyclopropylmethyl)-5-(isoxazol-5-ylcarbonyl)-6,7,9,10-tetrahydro[1,3]dioxolo[4,5-i][1,5]benzodiazocin-8 (5H)-one, 1-(cyclobutanecarbonyl)-5-cyclopropyl-8-methoxy-2,3,5,6-tetrahydrobenzo[b][1,5]diazocin-4(1H)-one, 9-cyclopentyl-6,7,9,10-tetrahydro[1,3]dioxolo[4,5-i][1,5]benzodiazocin-8(5H)-one, 5-(3-tert-butoxy-2-hydroxypropyl)-9-cyclopropyl-6,7,9,10-tetrahydro[1,3]dioxolo[4,5-i][1,5]benzodiazocin-8 (5H)-one, 5-ethyl-1-(2-hydroxypropyl)-2,3,5,6-tetrahydrobenzo [b][1,5]diazocin-4(1H)-one, 5-[3-(allyloxy)-2-hydroxypropyl]-9-ethyl-6,7,9,10-tetrahydro[1,3]dioxolo[4,5-i][1,5]benzodiazocin-8(5H)-one, 9-ethyl-5-(2-hydroxy-3-phenylpropyl)-6,7,9,10-tetrahydro[1,3]dioxolo[4,5-i][1,5]benzodiazocin-8(5H)-one, 5-ethyl-8-fluoro-1-(2-hydroxy-3,3-dimethylbutyl)-2,3,5,6-tetrahydrobenzo[b][1,5]diazocin-4(1H)-one, 7-(allyloxy)-5-ethyl-1-(2-hydroxy-3-phenoxypropyl)-8-methoxy-2,3,5,6-tetrahydrobenzo[b][1,5]diazocin-4 (1H)-one, (R)-1-(3-(benzyloxy)-2-hydroxypropyl)-5-cyclopentyl-8-fluoro-2,3,5,6-tetrahydrobenzo[b][1,5]diazocin-4(1H)-one, and 7-(allyloxy)-5-(cyclopropylmethyl)-1-(isoxazole-5-carbonyl)-8-methoxy-2,3,5,6-tetrahydrobenzo[b][1,5]diazocin-4(1H)-one.

20. A pharmaceutical composition comprising a compound according to claim 1 and a pharmaceutically acceptable carrier.

* * * * *